(12) United States Patent
Thon et al.

(10) Patent No.: US 10,590,373 B2
(45) Date of Patent: *Mar. 17, 2020

(54) SYSTEMS AND METHODS FOR BIOMIMETIC FLUID PROCESSING

(71) Applicants: BRIGHAM AND WOMEN'S HOSPITAL, INC., Boston, MA (US); PRESIDENT AND FELLOWS OF HARVARD COLLEGE, Cambridge, MA (US); VILNIUS UNIVERSITY, Vilnius (LT)

(72) Inventors: Jonathan N. Thon, Brookline, MA (US); Joseph E. Italiano, Chestnut Hill, MA (US); Linas Mazutis, Boston, MA (US); David A. Weitz, Boston, MA (US)

(73) Assignees: BRIGHAM AND WOMEN'S HOSPITAL, INC., Boston, MA (US); PRESIDENT AND FELLOWS OF HARVARD COLLEGE, Cambridge, MA (US); VILNIUS UNIVERSITY, Vilnius (LT)

( * ) Notice: Subject to any disclaimer, the term of this patent is extended or adjusted under 35 U.S.C. 154(b) by 232 days.

This patent is subject to a terminal disclaimer.

(21) Appl. No.: 15/300,070

(22) PCT Filed: Mar. 30, 2015

(86) PCT No.: PCT/US2015/023327
§ 371 (c)(1),
(2) Date: Sep. 28, 2016

(87) PCT Pub. No.: WO2015/153451
PCT Pub. Date: Oct. 8, 2015

(65) Prior Publication Data
US 2017/0183616 A1 Jun. 29, 2017

Related U.S. Application Data

(60) Provisional application No. 61/972,520, filed on Mar. 31, 2014.

(51) Int. Cl.
C12M 3/06 (2006.01)
C12M 1/42 (2006.01)
(Continued)

(52) U.S. Cl.
CPC ....... *C12M 23/16* (2013.01); *B01L 3/502715* (2013.01); *B01L 3/502761* (2013.01);
(Continued)

(58) Field of Classification Search
CPC ...... C12M 23/16; C12M 21/08; C12M 35/04; B01L 3/502761; B01L 3/502715;
(Continued)

(56) References Cited

U.S. PATENT DOCUMENTS 5,895,575 A * 4/1999 Kraus ................ B01D 39/1623
210/483
2012/0014933 A1 1/2012 Baruch et al.
(Continued)

FOREIGN PATENT DOCUMENTS

JP 2008301746 A 12/2008
JP 2012235749 A 12/2012
(Continued)

OTHER PUBLICATIONS

The International Search Report and Written Opinion dated Jul. 8, 2015 for International Application No. PCT/US2015/023327.
(Continued)

Primary Examiner — Sally A Merkling
(74) Attorney, Agent, or Firm — Quarles and Brady

(57) ABSTRACT

Systems and methods generating physiologic models that can produce functional biological substances are provided.
(Continued)

In some aspects, a system includes a substrate and a first and second channel formed therein. The channels extend longitudinally and are substantially parallel to each other. A series of apertures extend between the first channel and second channel to create a fluid communication path passing through columns separating the channels that extends further along the longitudinal dimension than other dimensions. The system also includes a first source configured to selectively introduce into the first channel a first biological composition at a first channel flow rate and a second source configured to selectively introduce into the second channel a second biological composition at a second channel flow rate, wherein the first channel flow rate and the second channel flow rate create a differential configured to generate physiological shear rates within a predetermined range in the channels.

25 Claims, 46 Drawing Sheets

(51) Int. Cl.
*B01L 3/00* (2006.01)
*C12M 3/00* (2006.01)
*C12N 5/078* (2010.01)

(52) U.S. Cl.
CPC ............ *C12M 21/08* (2013.01); *C12M 35/04* (2013.01); *C12N 5/0644* (2013.01); *B01L 3/5027* (2013.01); *B01L 2200/0605* (2013.01); *B01L 2200/0647* (2013.01); *B01L 2300/0681* (2013.01); *B01L 2300/0867* (2013.01); *B01L 2300/163* (2013.01); *C12N 2521/00* (2013.01)

(58) Field of Classification Search
CPC ....... B01L 2300/0681; B01L 2300/163; B01L 2200/0605; B01L 2200/0647; B01L 2300/0867; B01L 3/5027; C12N 5/0644; C12N 2521/00
See application file for complete search history.

(56) References Cited

U.S. PATENT DOCUMENTS

| | | | |
|---|---|---|---|
| 2012/0108721 A1* | 5/2012 | Mazutis | ............... B01F 3/0807 524/236 |
| 2012/0238020 A1 | 9/2012 | Mitchell et al. | |
| 2013/0295601 A1* | 11/2013 | Park | .................. G01N 33/5011 435/32 |

FOREIGN PATENT DOCUMENTS

| | | |
|---|---|---|
| JP | 2013031428 A | 2/2013 |
| WO | 2010009307 A2 | 1/2010 |
| WO | 2014107240 A1 | 7/2014 |

OTHER PUBLICATIONS

Tehranirokh, M. et al., Microfluidic Devices for Cell Cultivation and Proliferation, Biomicrofluidics, 2013, vol. 7; abstract.
Nakagawa, et al., Two Differential Flows in a Bioreactor Promoted Platelet Generation from Human Pluripotent Stem Cell-Derived Megakaryocytes, Experimental Hematology, 2013, 41(8):742-748.

* cited by examiner

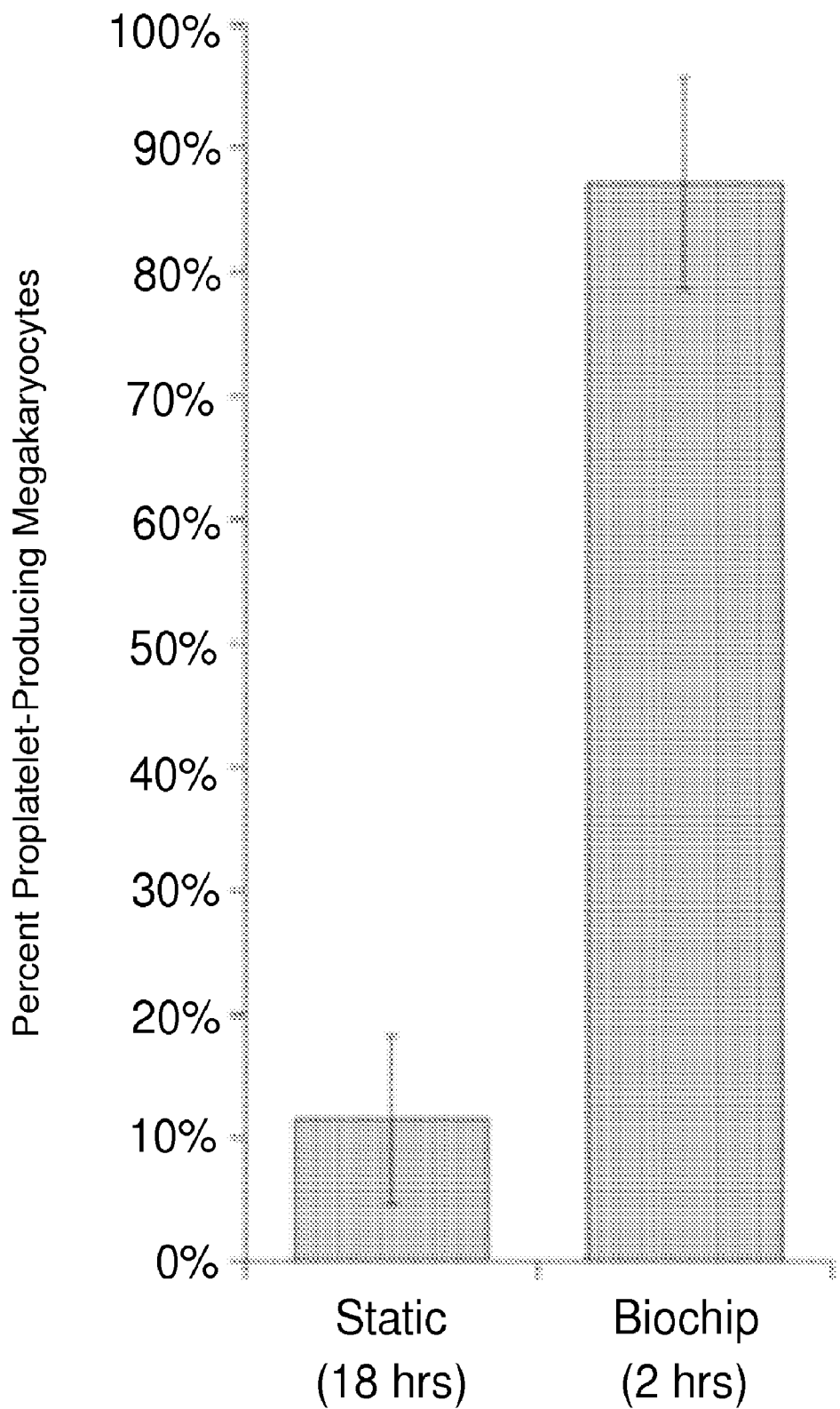

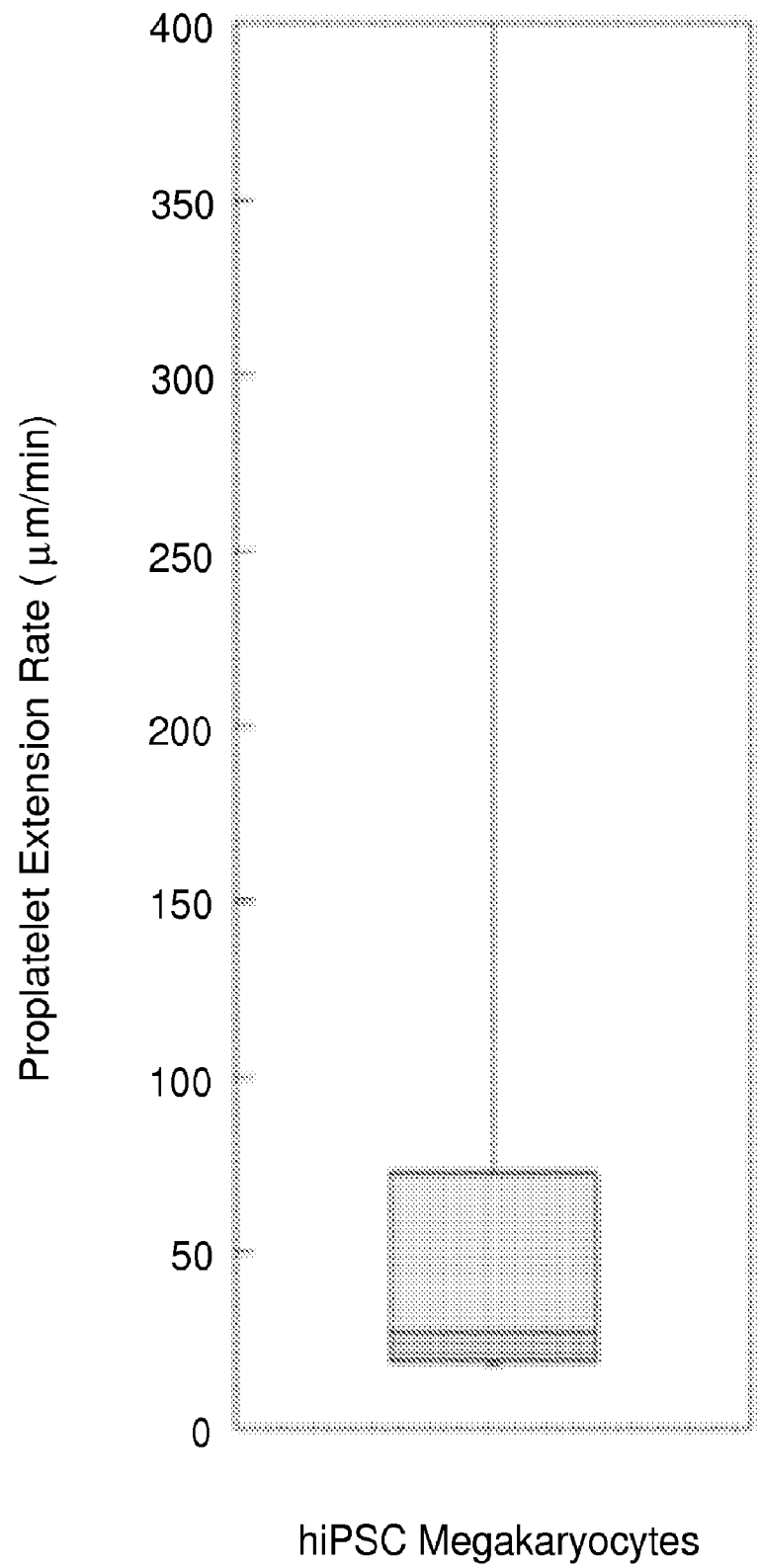

SYSTEMS AND METHODS FOR BIOMIMETIC FLUID PROCESSING

CROSS-REFERENCE TO RELATED APPLICATIONS

This application represents the U.S. National Stage of International Application No. PCT/US2015/023327, filed Mar. 30, 2015 which is based on, claims the benefit of, and incorporates by reference U.S. Provisional Application No. 61/972,520 filed Mar. 31, 2014, and entitled, "SYSTEM AND METHOD FOR BIOMIMETIC FLUID PROCESSING."

STATEMENT REGARDING FEDERALLY SPONSORED RESEARCH

This disclosure was made with government support under 1K99HL114719-01A1 and HL68130 awarded by the National Institutes of Health. The government has certain rights in the disclosure.

BACKGROUND OF THE DISCLOSURE

The present disclosure generally relates to fluid systems, including microfluidic devices, systems that include such devices, and methods that use such devices and systems. More particularly, the present disclosure relates to devices, systems, and methods for producing functional biological material, substances, or agents based on biomimetic platforms.

Blood platelets (PLTs) are essential for hemostasis, angiogenesis, and innate immunity, and when numbers dip to low levels, a condition known as thrombocytopenia, a patient is at serious risk of death from hemorrhage. Some causes for low platelet count include surgery, cancer, cancer treatments, aplastic anemia, toxic chemicals, alcohol, viruses, infection, pregnancy, and idiopathic immune thrombocytopenia.

Replacement PLTs to treat such conditions are generally derived entirely from human donors, despite serious clinical concerns owing to their immunogenicity and associated risk of sepsis. However, the shortages created by increased demand for PLT transfusions, coupled with near-static pool of donors and short shelf-life on account of bacterial testing and deterioration, are making it harder for health care professionals to provide adequate care for their patients. Moreover, alternatives such as artificial platelet substitutes, have thus far failed to replace physiological platelet products.

In vivo, PLTs are produced by progenitor cells, known as megakaryocytes (MKs), in a process illustrated in FIG. 8. Located outside blood vessels in the bone marrow (BM), MKs extend long, branching cellular structures (proPLTs) into sinusoidal blood vessels, where they experience shear rates and release PLTs into the circulation. While functional human PLTs have been grown in vitro, cell culture approaches to-date have yielded only about 10 percent proPLT production and 10-100 PLTs per human MK. By contrast, nearly all adult MKs in humans must produce roughly 1,000-10,000 PLTs each to account for the number of circulating PLTs. This constitutes a significant bottleneck in the ex vivo production of platelet transfusion units.

In addition, although second generation cell culture approaches have provided further insight into the physiological drivers of PLT release, they have been unable to recreate the entire BM microenvironment, exhibiting limited individual control of extracellular matrix (ECM) composition, BM stiffness, endothelial cell contacts, or vascular shear rates; and have been unsuccessful in synchronizing proPLT production, resulting in non-uniform PLT release over a period of 6-8 days. Moreover, the inability to resolve proPLT extension and release under physiologically relevant conditions by high-resolution live-cell microscopy has significantly hampered efforts to identify the cytoskeletal mechanics of PLT production to enable drug development and establish new treatments for thrombocytopenia. Therefore, an efficient, donor-independent PLT system capable of generating clinically significant numbers of functional human PLTs is necessary to avoid risks associated with PLT procurement and storage, and help meet growing transfusion needs.

Considering the above, there continues to be a clear need for devices, systems, and methods employing platforms that can reproduce vascular physiology in order to accurately reflect the processes, mechanisms, and conditions influencing the efficient production of functional human blood platelets. Such platforms would prove highly useful for the purposes of efficiently generating human platelets for infusion, as well as for establishing drug effects and interactions in the preclinical stages of development.

SUMMARY OF THE DISCLOSURE

The present disclosure overcomes the drawbacks of aforementioned technologies by providing systems and methods capable of producing physiologically accurate models, which replicate conditions, environments, structures, and dynamic flows found in vivo. As will be described, such physiological models may be utilized to generate functional human blood platelets, and other biological materials, that would be amenable for infusive treatment of certain medical conditions, such as platelet-deficient conditions like thrombocytopenia. Other applications for physiological models, produced in accordance with the present disclosure, may also include drug development, as well as drug and treatment assessment.

In accordance with one aspect of the present disclosure, a biomimetic microfluidic system is provided. The system includes a substrate, a first channel formed in the substrate, the first channel extending from a first input to a first output along a longitudinal dimension and extending along a first transverse dimension, and a second channel formed in the substrate, the second channel extending from a second input to a second output along the longitudinal dimension and extending along the first transverse dimension, wherein the first and second channels extend substantially parallel along the longitudinal dimension and are separated by columns extending along a second transverse dimension. The system also includes a series of apertures formed in the columns separating the first channel and second channel, wherein each of the series of apertures extend along the longitudinal dimension further than in the first transverse direction and the second transverse direction and are positioned proximal to a first portion of the substrate and extend from the first channel to the second channel to create a fluid communication path passing between the first channel and second channel. The system further includes a first source connected to the first input, the first source configured to selectively introduce into the first channel at least one first biological composition at a first channel flow rate, and a second source connected to the second input, the second source configured to selectively introduce into the second channel at least one second biological composition at a second channel flow rate, wherein the first channel flow rate and the second channel flow rate create a differential configured to generate physiological shear rates within a predetermined range in the channels.

In another aspect of the present disclosure, a method is disclosed for producing a physiological model of at least one of a bone marrow and blood vessel structure. A method includes providing a biomimetic microfluidic system that includes a substrate, a first channel formed in the substrate, the first channel extending from a first input to a first output along a longitudinal dimension and a first transverse dimension. A second channel is formed in the substrate, the second channel extending from a second input to a second output along the longitudinal dimension and the first transverse dimension. A third channel is formed in the substrate, the third channel extending from the second input to a third output along the longitudinal dimension and the first transverse dimension, wherein the first, second, and third channels extend substantially parallel along the longitudinal dimension and extend along a second transverse dimension. A series of microchannels connect the first channel to the second channel and connecting the third channel to the first channel, wherein the series of microchannels extend further in the longitudinal dimension than the first transverse direction and the second transverse direction and is positioned proximal to a first portion of the substrate to create a fluid communication path passing between the first channel and the second channel and the first channel and the third channel proximate to the first portion of the substrate. The method also includes introducing a first biological composition into the first channel at a first channel flow rate using the first source, and introducing a second biological composition into the second channel and third channel using the second source and at a second channel flow rate and a third channel flow rate, respectively, to create a differential between the first, second and third channel flow rates to generate physiological shear rates within a predetermined range in the channels. The method further includes harvesting a target biological substance produced proximate to the microchannels by the physiological shear rates.

In yet another aspect of the present disclosure, another biomimetic microfluidic system is provided. The system includes at least one substrate, and a first chamber formed in the at least one substrate, the first chamber extending from a first input to a first output substantially along a longitudinal dimension. The system also includes a second chamber formed in the at least one substrate, the second chamber extending from a second input to a second output along the longitudinal dimension, wherein the first and second chambers extend substantially parallel along the longitudinal dimension, and a membrane separating the first and second chamber along a transverse dimension, wherein the membrane creates a fluid communication path passing between the first chamber and second chamber. The system further includes at least one source configured to selectively introduce into the first chamber and the second chamber, using respective inputs, at least one biological composition at flow rates capable of generating physiological shear rates between the chambers that facilitate production of a plurality blood platelets.

The foregoing and other aspects and advantages of the disclosure will appear from the following description. In the description, reference is made to the accompanying drawings which form a part hereof, and in which there is shown by way of illustration a preferred embodiment of the disclosure. Such embodiment does not necessarily represent the full scope of the disclosure, however, and reference is made therefore to the claims and herein for interpreting the scope of the disclosure.

BRIEF DESCRIPTION OF THE DRAWINGS

The present disclosure will hereafter be described with reference to the accompanying drawings, wherein like reference numerals denote like elements.

FIG. 6E is a graphic illustrating that percent proPLT-producing hiPSC-MKs under physiological shear are increased significantly over static cultures.

FIG. 6F is a graph illustrating that proPLT extension rates under physiological shear are about 19 μm/min.

DETAILED DESCRIPTION OF THE DISCLOSURE

Blood platelets (PLTs) play a critical role in stimulating clot formation and repair of vascular injury. Morbidity and mortality from bleeding due to low PLT count is a major clinical problem encountered across a number of conditions including chemotherapy or radiation treatment, trauma, immune thrombocytopenic purpura (ITP), organ transplant surgery, severe burns, sepsis, and genetic disorders. Despite serious clinical concerns owing to their immunogenicity and associated risks, along with inventory shortages due to high demand and short shelf life, PLT transfusions total more than 10 million units per year in the United States.

In recognizing such wide-spread needs and risks, the present disclosure describes herein systems and methods capable of replicating conditions, environments, structures, and dynamic flows present in physiology. Such systems and methods may be used to generate models of human physiology, which can then be used to produce functional human PLTs, for instance.

Figure 8:
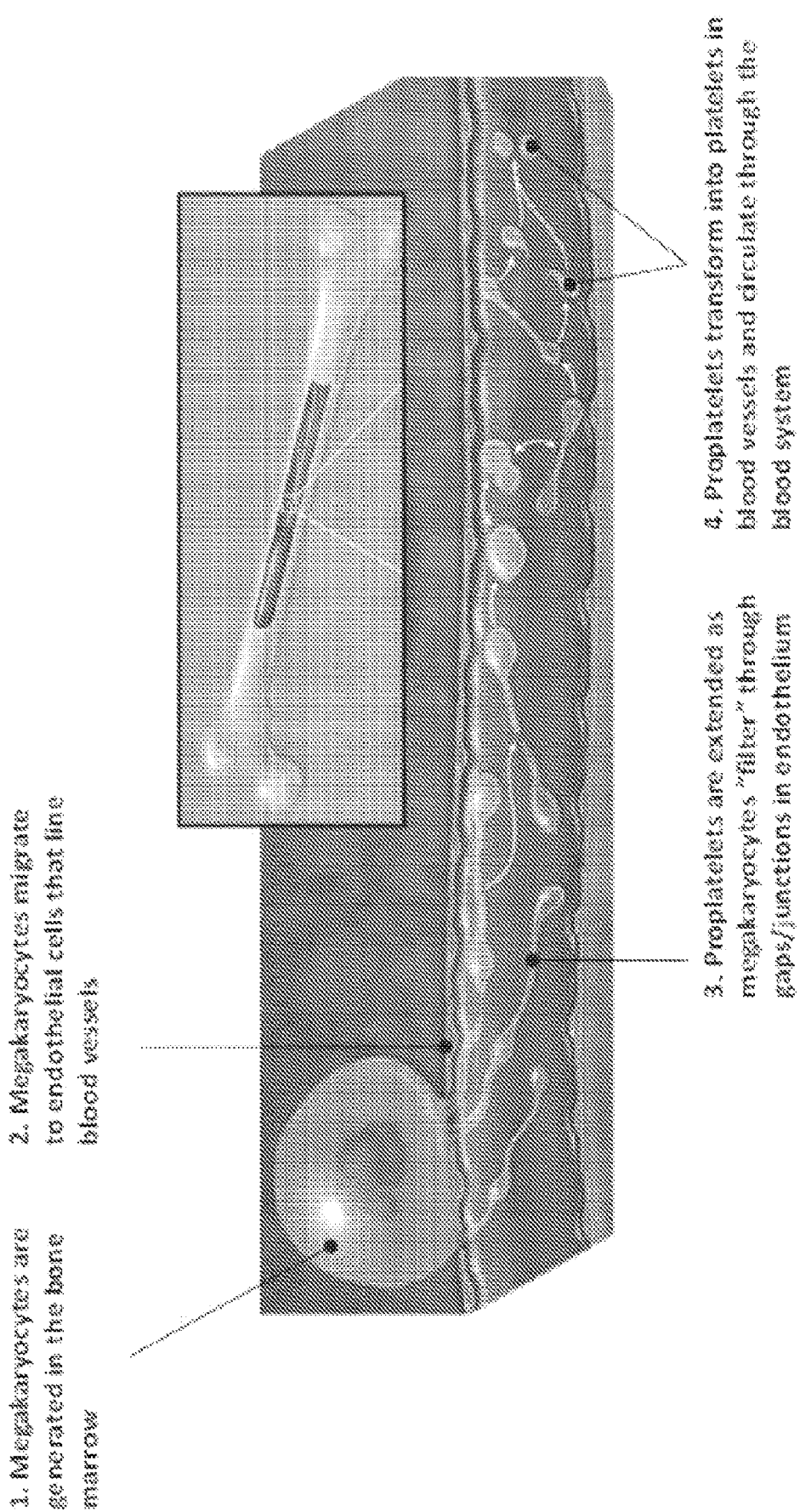
FIG. 8 shows an illustration depicting PLT production in vivo.

PLT production involves the differentiation of megakaryocyte (MKs), which sit outside sinusoidal blood vessels in the bone marrow (BM) and extend long, branching cellular structures (designated proPLTs) into the circulation, as shown in FIG. 8. Specifically, proPLTs include PLT-sized swellings in tandem arrays connected by thin cytoplasmic bridges. In vivo, they experience vascular shear and function as the assembly lines for PLT production. Although detailed characterization of proPLTs remains incomplete, these structures have been identified both in vitro and in vivo.

PLTs are released sequentially from proPLT tips. This mechanism is highly dependent on a complex network of tubulin and actin filaments that function as the molecular struts and girders of a cell. Microtubule (MT) bundles run parallel to proPLT shafts, and proPLT longation is driven by MTs sliding over one another. During proPLT maturation, organelles and secretory granules traffic distally over MT rails to become trapped at proPLT tips. Actin promotes proPLT branching and amplification of PLT ends. Live cell microscopy of murine MKs has been vital to this understanding, however most studies to date have been done in vitro on static MK cultures.

Thrombopoietin (TPO) has been identified as the major regulator of MK differentiation, and it has been used to produce enriched populations of MKs in culture. In one reference, it was demonstrated that human PLTs generated in vitro from proPLT-producing MKs were functional. Since then, MKs have been differentiated from multiple sources, including fetal liver cells (FLCs), cord blood stem cells (CBSCs), embryonic stem cells (ESCs), and induced pluripotent stem cells (iPSCs). However, current 2-D and liquid MK cultures fall orders of magnitude short of the estimated about 2000 PLTs generated per MK in vivo. More recently, modular 3-D knitted polyester scaffolds have been applied under continuous fluid flow to produce up to $6 \times 10^6$ PLTs/day from 1 million CD34+ human cord blood cells in culture. While suggestive that clinically useful PLT numbers may be attained, those 3-D perfusion bioreactors do not accurately reproduce the complex structure and fluid characteristics of the BM microenvironment, and their closed modular design prevents visualization of proPLT production, offering little insight into the mechanism of PLT release. Alternatively, 3-D polydimethylsiloxane (PDMS) biochips adjacent ECM-coated silk-based tubes have been proposed to reproduce BM sinusoids and study MK differentiation and PLT production in vitro. Although such devices recapitulate MK migration during maturation, they are not amenable to high resolution live-cell microscopy, and fail to reproduce endothelial cell contacts necessary to drive MK differentiation.

While MK differentiation has been studied in culture, the conditions that stimulate proPLT production remain poorly understood, particularly in vivo. MKs are found in BM niches, and some evidence suggests that cell-cell, cell-matrix, and soluble factor interactions of the BM stroma contribute to proPLT formation and PLT release. Indeed, the chemokine SDF-1 and growth factor FGF-4 recruit MKs to sinusoid endothelial cells. Extracellular matrix (ECM) proteins are another major constituent of the BM vascular niche, and evidence suggests that signaling through trans-membrane glycoprotein (GP) receptors regulate proPLT formation, PLT number and size, with defects seen for example, in Bernard-Soulier syndrome, Glanzmann's thrombasthenia. Collagen IV and vitronectin promote proPLT production, which can be inhibited by antibodies directed against their conjugate integrin receptor, GPIbα. Likewise, fibrinogen regulates proPLT formation and PLT release through GPI-IbIIIa. While these findings shed light on the environmental determinants of proPLT production, they are limited by a reductionist approach. Therefore, new models that incorporate the defining attributes of BM complexity are necessary to elucidate the physiological regulation of MKs into PLTs.

In the BM, proPLTs experience wall shear rates ranging from, 100 to 10,000 $s^{-1}$ or, more particularly, from 500 to 2500 $s^{-1}$. While the role of continuous blood flow on PLT thrombus formation has been studied, surprisingly little attention has been paid to the mechanism by which shear forces regulate PLT release. Also, when investigated, experiments have not been representative of true physiological conditions. Some preliminary studies have perfused MKs over ECM-coated glass slides, which select for immobilized/adhered MKs without discriminating ECM-contact activation from shear. Alternatively, released proPLTs have been centripetally agitated in an incubator shaker, which does not recapitulate circulatory laminar shear flow, does not provide precise control of vascular shear rates, and is not amenable to high-resolution live-cell microscopy. Despite these major limitations, exposure of MKs to high shear rates appears to accelerate proPLT production and while proPLTs cultured in the absence of shear release fewer PLTs than those maintained at fluid shear stresses.

The present disclosure recognizes that microfluidic devices can provide excellent platforms to generate and precisely tune dynamic fluid flows, and thus mimic blood vessel conditions for delivering chemical cues to cells. Embedding microfluidic networks within cell-laden hydrogels has been shown to support efficient convective transport of soluble factors through 3D scaffolds. Viable 3D tissue contacts have been produced consisting of hepatocytes encapsulated in agarose, calcium alginate hydrogels seeded with primary chondrocytes, and endothelial cells embedded in 3D tubular poly(ethylene glycol) hydrogels. Accordingly, the technology has been applied to the development of organs-on-a-chip, including liver, kidney, intestine, and lung. In addition, recent development of microvasculature-on-a-chip models have been used to study cardiovascular biology and pathophysiology in vitro. These studies emphasize the importance of mimicking the physical microenvironment and natural chemical cues of living organs to study cellular and physiological development. For example, this is particularly important for drug-mediated inhibition of PLT production. Since proPLT-producing MKs sit just outside blood vessels in the BM, interacting with both the semi-solid ECM microenvironment of BM and fluid microenvironment of the circulation, biomimetic microfluidic biochips may achieve a model system to elucidating the relevant physiological mechanisms, such as those responsible for drug-induced thrombocytopenia.

Figure 1:
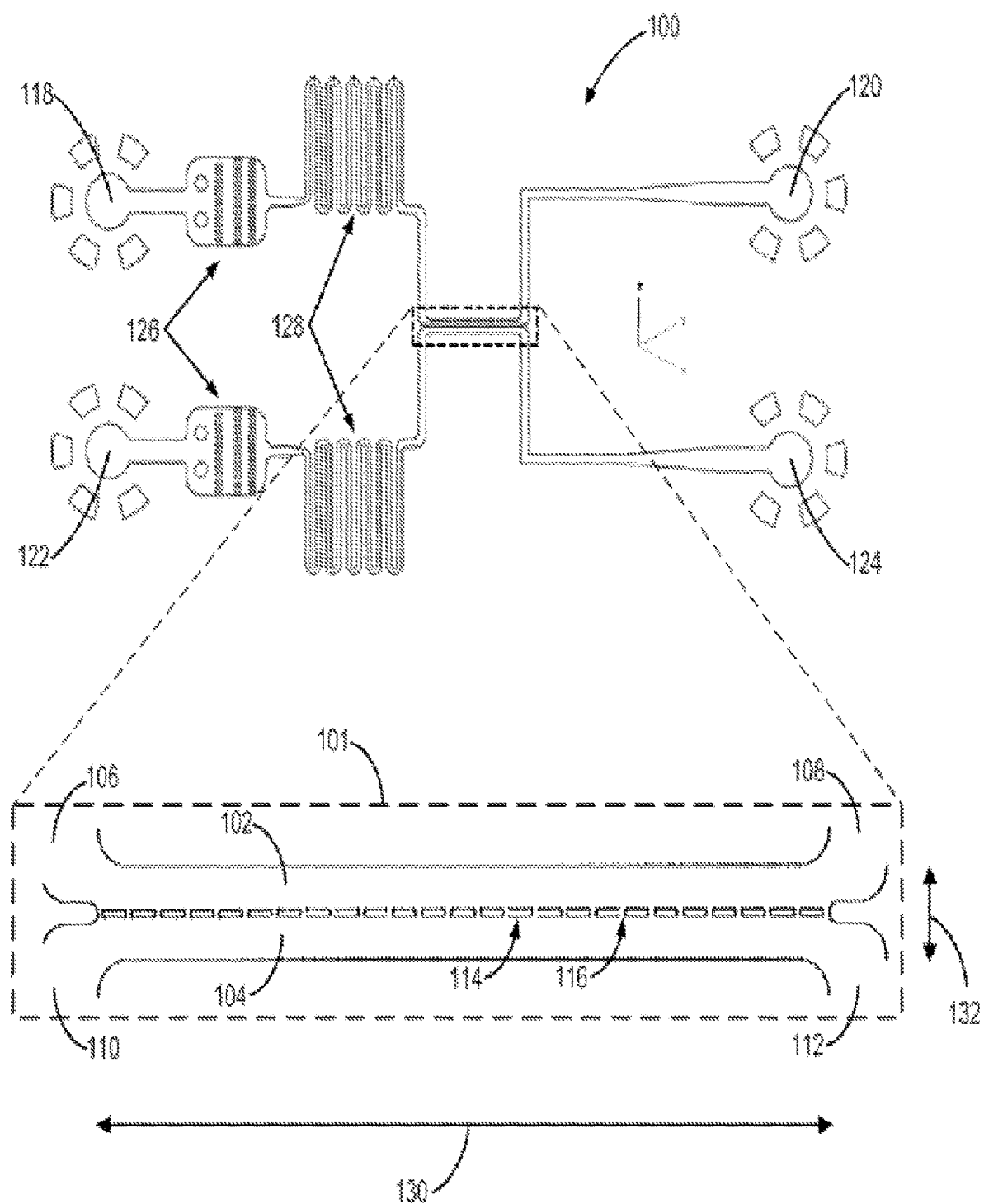
FIG. 1 shows a schematic diagram of an example biomimetic microfluidic system, in accordance with aspects of the present disclosure.

Turning now to FIG. 1, a schematic is shown illustrating a non-limiting example of a biomimetic system 100, in accordance with various embodiments of the present disclosure. The system 100 includes a substrate 101, a first channel 102 and a second channel 104, wherein each channel is configured to carry a flow of any fluid medium transporting or consisting of but not limited to, for example, particles, cells, substances, particulates, materials, compositions and the like. In one embodiment, the system 100 and/or substrate 101 may be constructed using cell-inert silicon-based organic polymers, such as polydimethylsiloxane (PDMS).

The first channel 102 includes a first channel input 106 and first channel output 108. Similarly, the second channel 104 includes a second channel input 110 and second channel output 112. The first channel 102 and second channel 104 extend along a substantially longitudinal direction, and are longitudinally and transversally dimensioned, as will be explained, to achieve desired flow profiles, velocities, or rates, such as those present in a physiological system. In one aspect, the size of the longitudinal 130 and transverse 132 dimensions describing the channels may be in a range consistent with an anatomical or physiological structure, assembly, configuration or arrangement, such as in the case of bone marrow and blood vessels. By way of example, the longitudinal 130 dimension may be in the range of 1000 to 30,000 micrometers or, more particularly, in the range of 1000 to 3000 micrometers, and the transverse 132 dimension may be in the range of 100 to 3,000 micrometers or, more particularly, in the range of 100 to 300 micrometers, although other values are possible. In some aspects, each channel may be prepared, conditioned, or manufactured to receive, localize, trap, or accumulate for example, particles, cells, substances, particulates, materials, compositions, and the like, from a traversing fluid medium.

The system 100 also includes a series of columns 114 that separate the first channel 102 and second channel 104. The long axes of the columns 114 may be arranged substantially parallel to the longitudinal 130 dimension of the channels, the series of columns 114 extending for a distance substantially equal to the longitudinal 130 dimension of the channels. The columns 114 may be separated by a series of gaps, or microchannels 116, that extend from the first channel 102 to the second channel 104 to create a partial fluid communication path passing between the columns 114. However, the term "microchannel" when referring to the gaps does not connote a particular width. For example, the gaps may be substantially greater or smaller than the micrometer range. In some aspects, the columns 114 and microchannels 116 may be dimensioned such that particles, cells, substances, particulates, materials, compositions, and the like, may bind, adhere to or otherwise be confined to an area generally in the vicinity of the columns 114 and microchannels 116. As an example, the longitudinal 130 and transverse 132 dimensions of the columns 114 may be in the range of 1 to 200 micrometers, while the longitudinal 130 dimension of the microchannels 116, defined by the separation distances or gaps between the columns 114, may be in the range of 0.1 to 20 micrometers, although other values are possible.

In some aspects, flow of a first medium in the first channel 102 may be established using a first source coupled to a first inlet 118, wherein the flow of the first medium is extractable via a first outlet 120. Similarly, flow of a second medium in the second channel 102 may be established using a second source coupled to a second inlet 118, wherein the flow of the second medium is extractable via a second outlet 120. However, flow from the first channel 102 or second channel 104 may be extracted through either the first outlet 120 or the second outlet 122 by virtue of the fluid communication between them. In some configurations, either the first outlet 120 or the second outlet 124, or both, may include capabilities for draining or capturing flow established using the first source or the second source, or both. Such capabilities may also include the ability to separate a desired material or substance from captured flow, such as blood platelets or thrombocytes.

The first and second source (not shown in FIG. 1) may include any system configured for delivering a controlled flow or fluid pressure, such a microfluidic pump system, and include any number of elements or components, such as flow regulators, actuators, and so forth. Flow velocities or flow rates, sustainable for any desired or required amount of time, may be controlled using specific configuration of sources, elements and components, as well as by virtue of the geometrical dimensions associated with the first channel 102 and second channel 104. In some aspects, flow rates in the first channel 102 and second channel 104 may be controlled to duplicate physiological conditions, as found, for example, in bone marrow and blood vessels. For instance, flow rates may be controlled to achieve desired vascular shear rates sufficient for generating PLTs.

The system 100 may also include filtration and resistive elements, of any shape or form, and arranged along the paths of each of the first and second fluid mediums in dependence of the direction of flow. Specifically, the filtration elements may be designed to capture or remove from the traversing fluid mediums any kind of debris, dust and other contaminants or undesirable materials, elements, or particulates. In addition, the resistive elements may be desired to control flow forces or damp fluctuations in flow rate. In some configurations, as shown in FIG. 1, filtration elements 126 may be situated in proximity to the first inlet 118 and second inlet 122 in order to immediately capture undesired contaminants. The flow resistive elements 128 may then be situated downstream from the filtration elements 126, as shown in FIG. 1.

In some implementations, recreating human bone marrow (BM) vascular niche ex vivo may be achieved by selectively filling the first channel 102 with any combination of bone powder, peptides, or proteins that regulate platelet producing, including but not limited to CI, CIV, FG, FN, VN, LN, VWF Poly-L-lysine, fibrinogen, collagen type IV, fibronectin, vitronectin, laminin, CCL5 (RANTES), S1PR1, SDF-1, and FGF-4, gels, such as agarose, alginate, and matrigel or solutions such as PBS, HBS, DMEM EGM or other media. Alternatively, ECM proteins may be patterned directly onto glass surfaces or porous membranes prior to adhesion of biochips to surface slides using protein micro/nano-stamping, or following microfluidic device assembly using parallel microfluidic streams. Local component concentration may be adjusted by regulating the microfluidic stream flow rate during infusion, with focus on alignment and 3-D arrangement.

In other implementations, recapitulating human BM vasculature may be achieved by selectively coating the second channel 104 by culturing with endothelial cells at 37 degrees Celsius and 5 percent $CO_2$. Endothelial cells may be fixed with 4% formaldehyde, and probed for cellular biomarkers to resolve cellular localization and architecture. The second channel 104 of endothelialized BM biochips may be perfused with a fluorescent or colorimetric medium such as FITC-dextran or with beads, and visualized by live-cell microscopy to assess sample/cell/molecule diffusion and determine vascular permeability.

Figure 9:
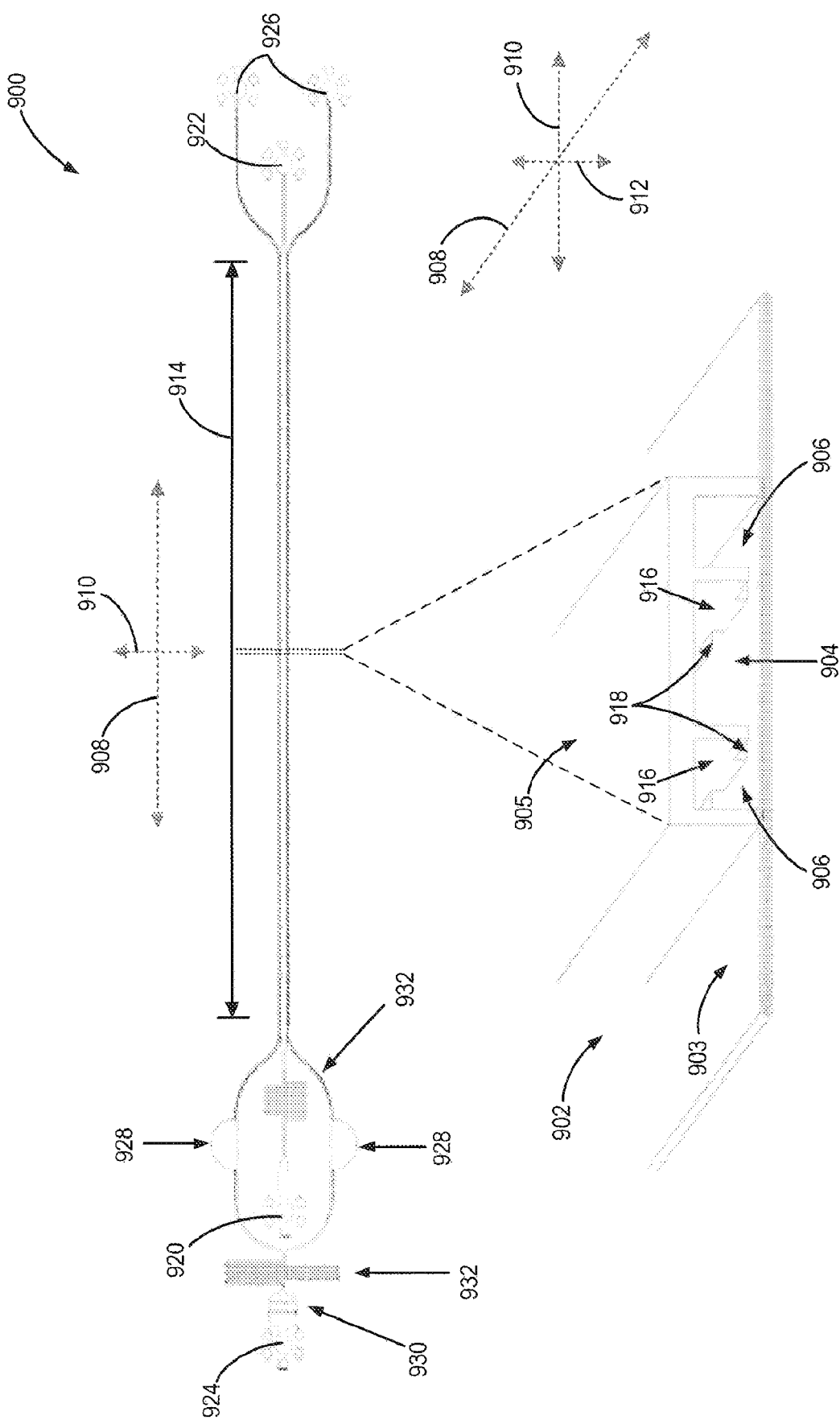
FIG. 9 shows a schematic diagram of another example biomimetic microfluidic system, in accordance with aspects of the present disclosure.

Turning now to FIG. 9, another non-limiting example of a biomimetic system 900 is shown, in accordance with various embodiments of the present disclosure. The system 900 includes a substrate 902, wherein a first, or central channel 904, along with a second and third channel, or side channels 906, lateral or adjacent to the central channel 904, are formed. Each channel of system 900 may be configured to carry a flow of any fluid medium transporting or consisting of but not limited to, for example, particles, cells, substances, particulates, materials, compositions, agents and the like. In some aspects, system 900 and/or the substrate 902 may be constructed using cell-inert silicon-based organic polymers, such as polydimethylsiloxane (PDMS), COP, COC, PC, PS, PMMA, glass, and/or any other suitable materials or combinations thereof. In certain configurations, the substrate 902 may include, or be assembled from, separable, re-sealable, or bondable components, such as a first portion 903 and second portion 905 of the substrate, fashioned and/or combined using appropriate techniques and methods.

The central channel 904 and side channels 906 extend substantially parallel along a longitudinal direction 908. In some preferred aspects, the dimensions defining the channels along the longitudinal direction 908 and the transverse directions, 910 and 912, may be in a range consistent with physiological structures. Moreover, certain dimensions may also be desirable to facilitate deposition of cells, substances, compositions or other materials within the channels, or to sustain, regulate or reproduce desired fluid flow profiles, velocities, pressures, or rates, such as those associated with physiological systems. In some designs, dimensions of the central channel 904 and side channels 906 along transverse directions 910 and 912 need not be equal, as illustrated in FIG. 9. By way of example, a longitudinal dimension 914 of all channels may be in the range of 1000 to 30,000 micrometers, while transverse dimensions for each channel may be in the range of 10 to 3,000 micrometers or, more particularly, in the range of 10 to 150 micrometers. Other values for the longitudinal and transverse dimensions are also possible.

The channels are separated by columns 916, generally arranged parallel to the longitudinal direction 908, and extending for a distance substantially equal to the longitudinal dimension 914 of the channels. The columns 916 may include any number of apertures 918, that create a partial fluid communication path between the channels, the apertures 918 being shaped, dimensioned and arranged, as desired. The apertures 918 may be, for example, openings, slits, pores, gaps, microchannels, and the like, that extend between the central channel 904 and each of first and/or second side channels 906. As an example, the longitudinal and transverse dimensions of the apertures 918 may be in the range of 0.1 to 20 micrometers, although other values are possible. As illustrated in FIG. 9, the apertures 918 may have a greater longitudinal dimension than transverse dimensions. In some preferred designs, the apertures 918 are generally located proximal to the first portion 903 of the substrate, as illustrated in FIG. 9. To this end, the apertures 918 may extend against the first portion 903 of the substrate. This may allow trapped MKs and/or proPLTs, for example, to be pressed against the surface of the first portion 903 of the substrate by way of fluid pressure or pressure differential generated by traversing fluid medium(s). In the case that the first portion 903 of the substrate is transparent, improved resolution may be achieved with respect to imaging proPLT and PLT production processes. In this manner, the apertures 918 may be arranged, shaped and dimensioned to optimally produce, or maximize yield of desirable biological substances, such as PLTs.

As shown in FIG. 9, the central channel 904 includes a first channel input, or central channel input 920, and a first channel output, or central channel output 922. The side channels 906 may share a second channel input, or side channel input 924, and include separate second and third channel outputs, or side channel outputs 926. Proximal to the side channel input 924, each side channel 906 of system 900 includes an expansion portion, or port 928. In certain modes of operation, the expansion portions, or ports 928 may function as additional fluid inputs or outputs for each of the respective side channel 906, providing increased flexibility for system 900, as will be described.

The system 900 may also include filtration capabilities, which can take any shape or form, and are configured to capture or absorb any kind of debris, dust and any other contaminants from traversing fluids, while allowing flow of cells, agents or other desired materials contained therein, such as MKs. In the non-limiting configuration shown in FIG. 9, filtration elements 930 may be situated in proximity to the side channel input 924. In addition, the system 900 may also include flow control capabilities, which may take a variety of shapes or forms, and designed to control flow forces or damp fluctuations in flow rates. In the non-limiting configuration shown in FIG. 9, flow resistive elements 932 may be situated proximal to channel inputs 920 and 924.

As described with reference to FIG. 1, the channels, columns 916 and apertures 918 may be prepared such that particles, cells, substances, particulates, materials, compositions, and the like, may bind, adhere to or otherwise be confined to any area generally within the channels or in the vicinity of the columns 916 and apertures 918, and, thereby, allowing harvest of any desired or target biological substance from an area proximate to the apertures 918. Non-limiting examples of compositions, materials or agents, for pre-coating the channels and/or columns 916 or and apertures 918 can include, but are not limited to, bovine serum albumin, fibrinogen, fibrinectin, laminin, collagen type IV, collagen type I, Poly-L-lysine, vitronectin, CCL5, S1PR1, SDF-1, FGF-4, and other extracellular matrix proteins or proteins that regulate platelet production. In some aspects, such coatings may be performed during system 900 fabrication steps, or by subsequent perfusion via fluid medium flow through the channels. In addition, the channels may be seeded with cells or other biological compositions and materials, that include, but are not limited to, human or non-human endothelial cells, mesenchymal cells, osteoblasts and fibroblasts. In particular, to replicate or mimic three-dimensional extracellular matrix organization and physiological bone marrow stiffness, cells may be infused in a hydrogel solution, which may subsequently be polymerized. The hydrogel solution may include, but is not limited to, alginate, matrigel, and agarose, which may then be selectively embedded in any channels, as desired.

Figure 10:
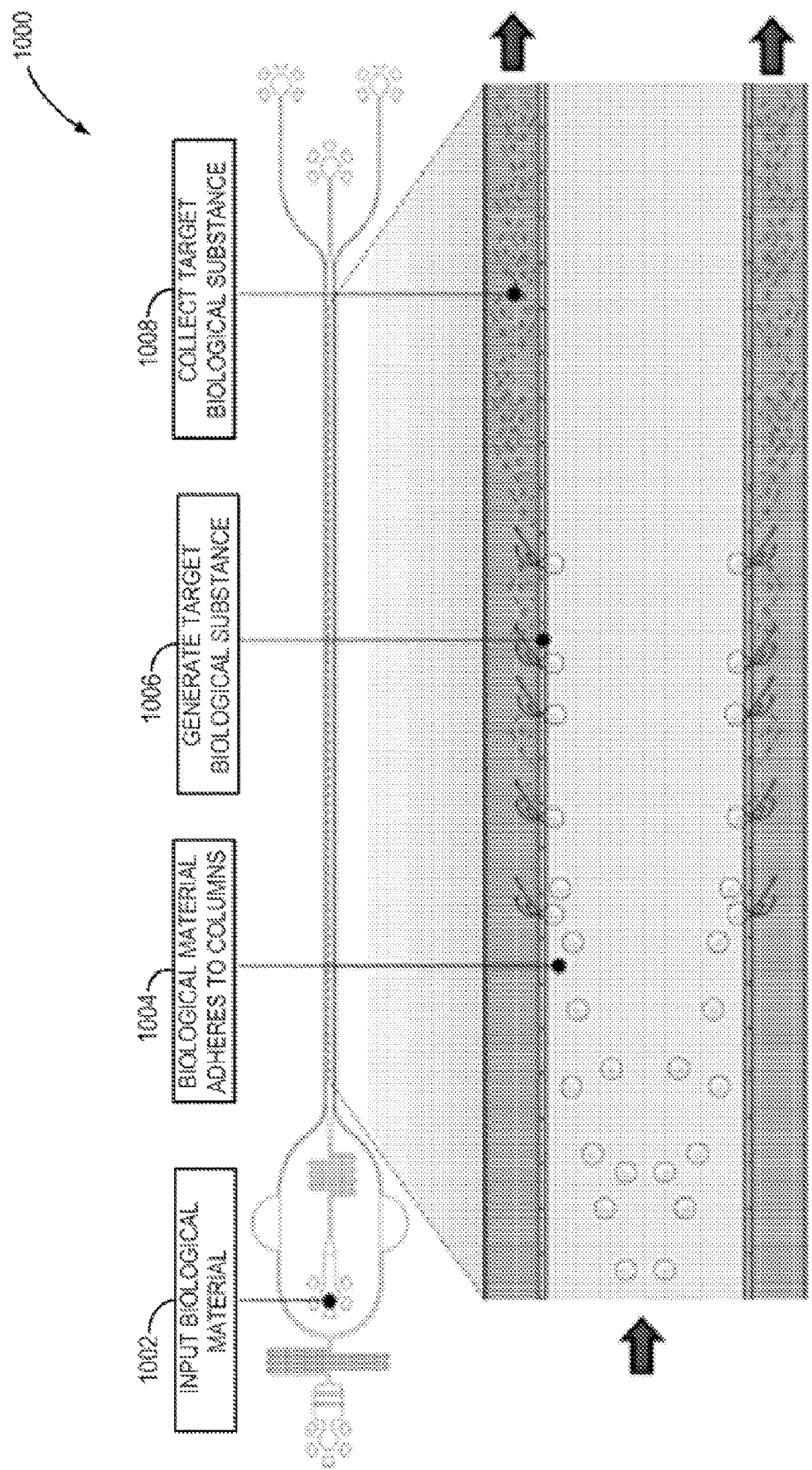
FIG. 10 shows an illustration depicting PLT production using the system of FIG. 9.

Turning to FIG. 10, an example mode of operation for system 900 is shown, depicting an example process 1000 of generating desired or target biological substances, such as blood PLTs. Specifically, a first biological material or composition is provided via the central channel input 920 at step 1002. Such biological material may include cells contained therein for generating PLTs, such as MKs. Then, at step 1004, at least some portions of the biological material may adhere to regions generally about the columns 916 and apertures 918, as described. For example, MKs may become trapped in proximity to the apertures 918. At step 1006 a target biological substance may be generated by virtue of flow rates, velocities, shear rates, or pressure differentials in the channels. For example, proPLTs extended as MK's traverse, are trapped about, or filter through the apertures 918, and subsequently transform into PLTs. At step 1008 the target biological substance produced is carried by the fluid medium and may be collected and separated from the effluent for subsequent use. At step 1010, post-collection processing may be performed. For example, step 1010 may include a process to dialyze the bioreactor-derived platelets in an FDA-approved storage media, such as platelet additive solution, such as produced by Haemonetics, COBE Spectra, Trima Accel, and the like. For example, a dynamic dialysis system may be used, for example, one that uses continuous flow at low shear through 0.75 mm, 0.65µ mPES lumen, such as is made by Spectrum Labs. Furthermore, the post-collection processing at step 1010 may include a process to irradiate the platelet product before human infusion, as required by the FDA. Thus, the culture media may be replaced with a media that can be infused into human patients.

Figure 11A:
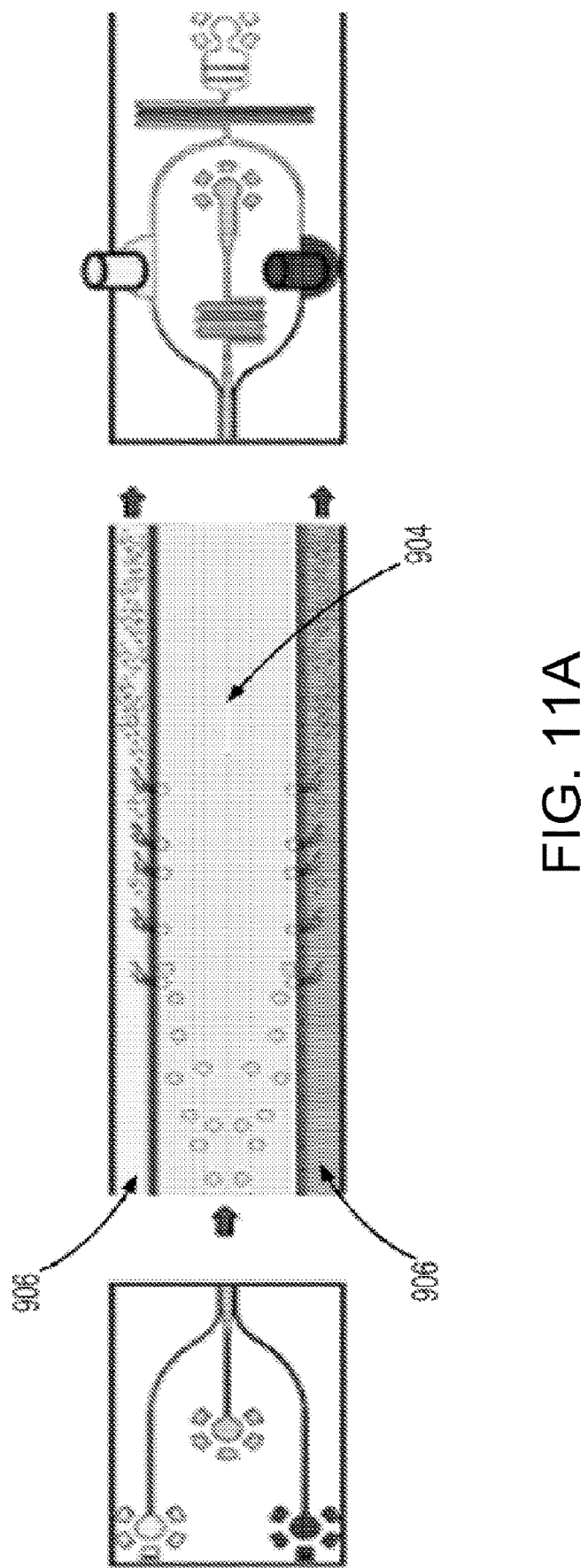
FIG. 11A shows an illustration comparing PLT production using one fluid flow implementation in the system of FIG. 9.
Figure 11B:
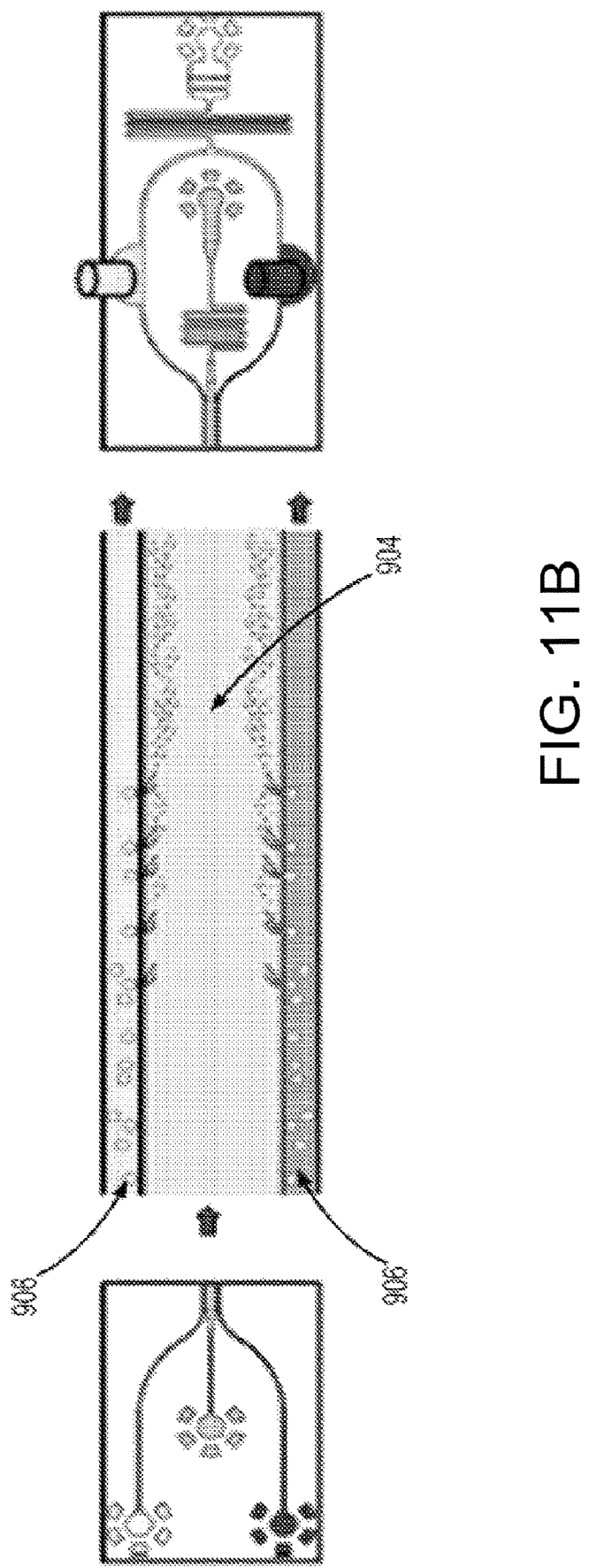
FIG. 11B shows an illustration comparing PLT production using another fluid flow implementation in the system of FIG. 9.

A unique design feature of system 900 is that media may be selectively infused, and in a bi-directional manner, by virtue of the described inputs, outputs, and expansion portions, or ports 928 functioning as additional fluid inputs or outputs. That is, media, cells, or any materials, compositions or substances may be separately or concurrently introduced into any or all the channels by both forward or reverse fluid flow. Therefore, in addition to increased harvest efficiency of PLTs, for example, on account of the two side channels 906, the system 900 also allows for controlling each channel independently, facilitating a head-to-head comparison of different operational conditions, such as, media, cells, coating agents, materials, shear rates, fluid flow directions and so forth. FIGS. 11A and 11B illustrate example fluid flow implementations for producing PLT's, whereby MK's can be introduced into either the central channel 904 (FIG. 11A), or each, or both, of the side channels 906 (FIG. 11B).

Figure 12:
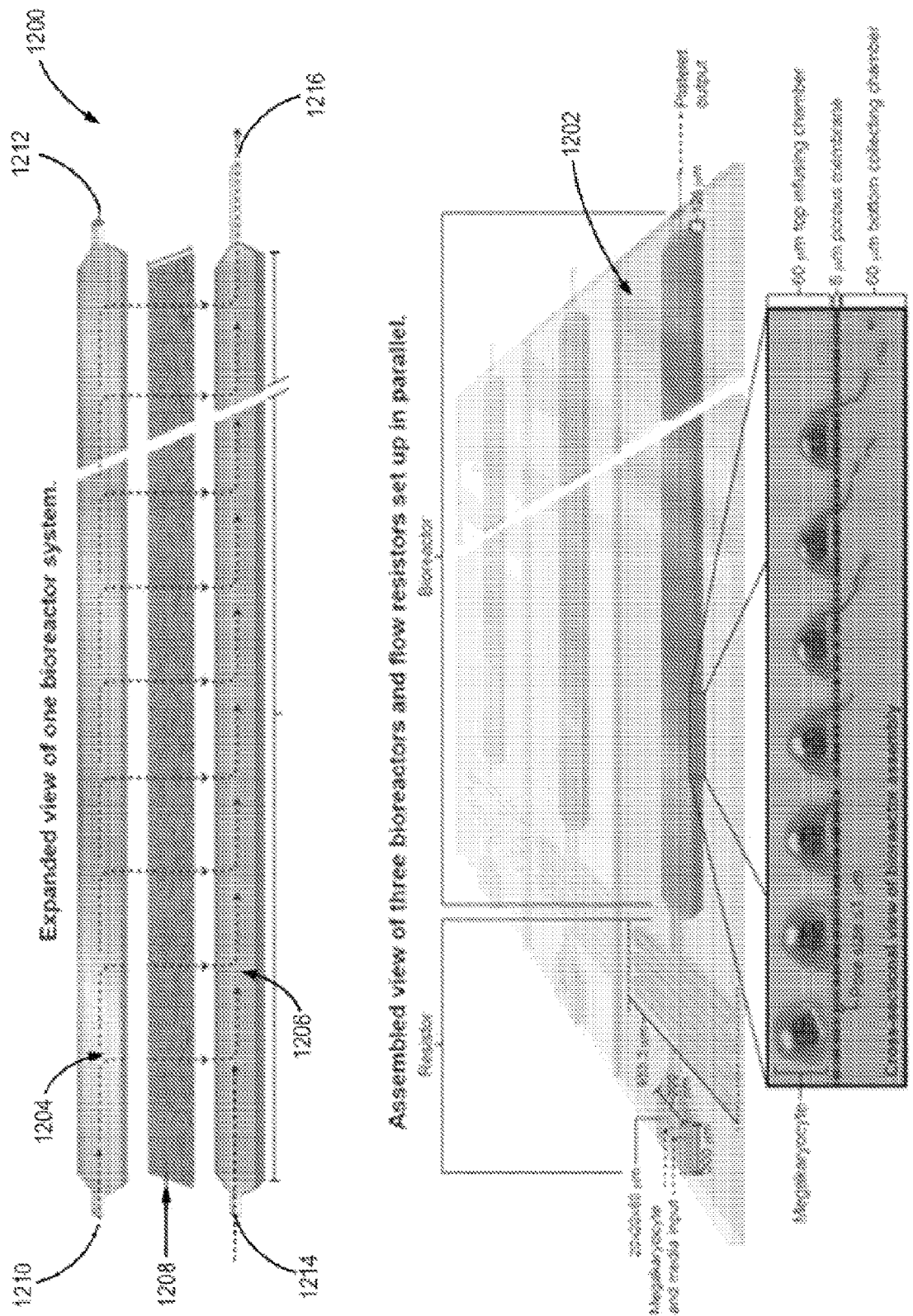
FIG. 12 shows an illustration of yet another biomimetic microfluidic system, in accordance with aspects of the present disclosure.

Turning now to FIG. 12, another non-limiting example of a biomimetic system 1200 in accordance with various embodiments of the present disclosure is shown. The system 1200 includes a substrate 1202. By way of example, the substrate 1202 may be constructed using cell-inert silicon-based organic polymers, such as polydimethylsiloxane (PDMS), COP, COC, PC, PS, PMMA, glass, and/or any other suitable materials or combinations thereof. As shown in FIG. 12, the substrate 1202 includes a first chamber 1204 and a second chamber 1206 formed therein, where chambers are separated by a porous membrane 1208.

In some applications, system 1200 may require assembly or disassembly, for example, for individually preparing the first chamber 1204, the second chamber 1206, or the porous membrane 1208. As such, system 1200 may include a second substrate (not shown in FIG. 12), where the first chamber 1204 is formed in the first substrate 1202, and the second chamber 1206 is formed in the second substrate. As such, system 1200 may include additional features that allow the first chamber 1204 and the second 1206 to be removably coupled. For example, system 1200 may include components or elements that facilitate breaking or restoring a fluid seal between the first chamber 1204, the second chamber 1206, and the porous membrane 1208.

The first chamber 1204 and the second chamber 1206 and may be shaped and dimensioned in any desired manner, with longitudinal, and transverse dimensions selected in dependence of a desired application. For instance, in order to produce a target biological substance with a desired yield, such as PLTs, the dimensions of the chambers may be optimized to control flow rates, velocity profiles, shear rates, shear stresses or pressure differentials between the chambers. As shown in the example of FIG. 12, the first chamber 1204 and second chamber 1206 may extend substantially parallel along a longitudinal direction. By way of example, the chambers may include longitudinal dimensions in a range between 1000 and 30,000 micrometers, and transverse dimensions in a range between 10 and 300 micrometers, although other values may be possible.

In some configurations, openings may also be incorporated into a top surface of first chamber 1204 to permit gas transfer into and out of the system 1200. As such, a hydrophobic gas-permeable membrane may be layered proximate to the first chamber 1204 to prevent materials from escaping through the openings. In such implementation, the system 1200 then includes the hydrophobic gas-permeable membrane, the first chamber 1204, the porous membrane 1208, and the second chamber 1206, optionally clamped together using, for example, a re-sealable chip holder, with each chamber formed in separate substrates, as described.

The porous membrane 1208 may be any element that can create a partial fluid communication path between the first chamber 1204 and second chamber 1206. For instance, the porous membrane 1208 may be a mesh or film having pores, apertures or microchannels configured therein. The porous membrane 1208 may be fashioned, shaped and dimensioned in accordance with a particular application. By way of example, the porous membrane 1208 may be constructed using materials, such as polycarbonate materials, PDMS, COP, COC, PC, PS, or PMMA. In addition, the porous membrane 1208 may include lateral and transverse, dimensions in a range between 1 and 100 millimeters, and have a thickness in a range between 0.1 to 30 micrometers, and more specifically between 8 and 12 micrometers, although other dimensions may be possible. In some designs, the porous membrane 1208 may extend beyond the dimensions of the individual chambers of system 1200. Specifically, the porous membrane 1208 may be configured with a large surface area for trapping desired biological materials, cells, and so forth, with capabilities of supporting multiple simultaneous proPLT production processes, as described below, hence contributing to increased PLT yield.

Selection of appropriate pore diameter for the porous membrane 1208 may be such that maximal trapping of cells, such as MKs, may be achieved. For instance, the porous membrane 1208 can have pores in the range between 0.1 to 20 micrometers, and more specifically between 5 and 8 micrometers, in diameter. In some aspects, the porous membrane 1208 may be prepared to include particular materials, chemicals or agents. For example, the porous membrane 1208 may include peptides or proteins that regulate platelet production, such as Poly-L-lysine, fribrinogen, collagen type IV, fibronectin, vitronectin, laminin, CCL5 (RANTES), S1PR1, SDF-1, FGF-4, and so forth.

As shown in FIG. 12, the first chamber 1204 includes an inlet 1210 and outlet 1212, and similarly the second chamber 1206 includes an inlet 1214 and an outlet 1216. In some aspects, the chambers can be individually prepared using various chemicals, agents or materials by infusion through respective chamber inlets, using one or more sources, or by incubating the individual layers in the relevant substrate(s). In other aspects, preparation by infusion of the first chamber 1204 and the second chamber 1206 may be performed in parallel. That is, fluid containing chemicals, agents or materials may be introduced through both inlets and collected from both outlets, so that laminar flow streams do not mix.

Non-limiting examples of chemicals, agents, or materials for use with system 1200 can include bovine serum albumin (for example, 1-10%), fibrinogen, fibronectin, laminin, collagen type IV, collagen type I, and other extracellular matrix proteins or proteins that regulate platelet production. In addition, one or both chambers can be seeded with cells to recapitulate bone marrow and blood vessel composition by perfusing them through or incubating the individual layers in the relevant cell culture. These include, but are not limited to, human or mouse endothelial cells, mesenchymal cells, osteoblasts and fibroblasts, and so on. Furthermore, to model three-dimensional extracellular matrix organization and physiological bone marrow stiffness, cells can be infused in a hydrogel solution that includes, but is not limited to, alginate, and agarose, that may be polymerized within the system 1200.

System 1200 may also include filtration capabilities, which can take any shape or form, and be configured to capture or absorb any kind of debris, dust and any other contaminants from traversing fluids. In some aspects, filters allow flow of cells, agents or other desired materials, such as MKs, therethrough In addition, the system 1200 may also include flow control capabilities, which may take a variety of shapes or forms, and be designed to control flow forces or damp fluctuations in flow rates. Furthermore, system 1200 may also include any system, device, source or apparatus configured to establish, sustain, or drain flow of any medium flowing through system 1200. As described, this can include one or more sources capable of duplicating physiological conditions by introducing in the chambers of system 1200 biological compositions at flow rates capable of generating physiological shears between the chambers in a predetermined range, wherein the predetermined range can be between 100 $s^{-1}$ and 10,000 $s^{-1}$.

As shown in FIG. 12, in some designs, multiple copies of system 1200 may be assembled in an array to produce a biomimetic device or system, with each copy of system 1200 operating either independently or linked to other copies. Such approach may provide a convenient and efficient way to parallelize the PLT production process. For instance, an inlet and/or outlet of one system 1200 may be connected to an inlet and/or outlet of a second system 1200, and so on. In some designs, inlets may be designed in such a way that biological materials, such as MKs, may be introduced and distributed randomly, or concurrently, into each system 1200 using one or more sources. In addition, outlets from each system 1200 may be connected into a single major channel that allows the collection into a single container of effluent containing a target biological substance, such as proPLTs and PLT's, from every system 1200 in the array.

By way of example, for a porous membrane 1208 of dimensions 50 millimeters by 75 millimeters, over 160 systems 1200 may be combined onto a single biomimetic device. Considering the number of pores for each system 1200 to be around of $1.2 \times 10^8$, this implies that each device may be capable of capturing roughly $2 \times 10^{10}$ cells, which represents a value high enough to produce sufficient numbers of PLTs for in vivo (animal and human) testing and infusion.

System 1200 includes several advantages, included the capability for specifically coating a first surface of pores located on the porous membrane 1208 with defined ECM proteins and a second surface of the pores without these proteins, or with other ECM proteins, ensuring that MKs may come to rest on the first surface contact their proteins of interest, while the proPLTs extended and the PLTs they release contact another. In addition, the design of system 1200, as described, facilitates cleaning, or swapping of various porous membranes 1208 configured from different materials and having different pore sizes, as needed for a particular applications.

Systems 100, 900, and 1200, in accordance with aspects of the present disclosure, provide platforms that replicate or reproduce physiological conditions found in human physiology by duplicating dimensions, environments and conditions therein. For instance, microfluidic channels separated by columns spaced closely apart, experiencing controlled environments and flow conditions, as described with reference to FIG. 1, provide a realistic physiological model that replicates human BM. By controlling MK trapping, BM stiffness, ECM composition, micro-channel size, hemodynamic vascular shear, and endothelial cell contacts, using systems 100, 900, and 1200, functional PLTs may be produced.

Figure 13:
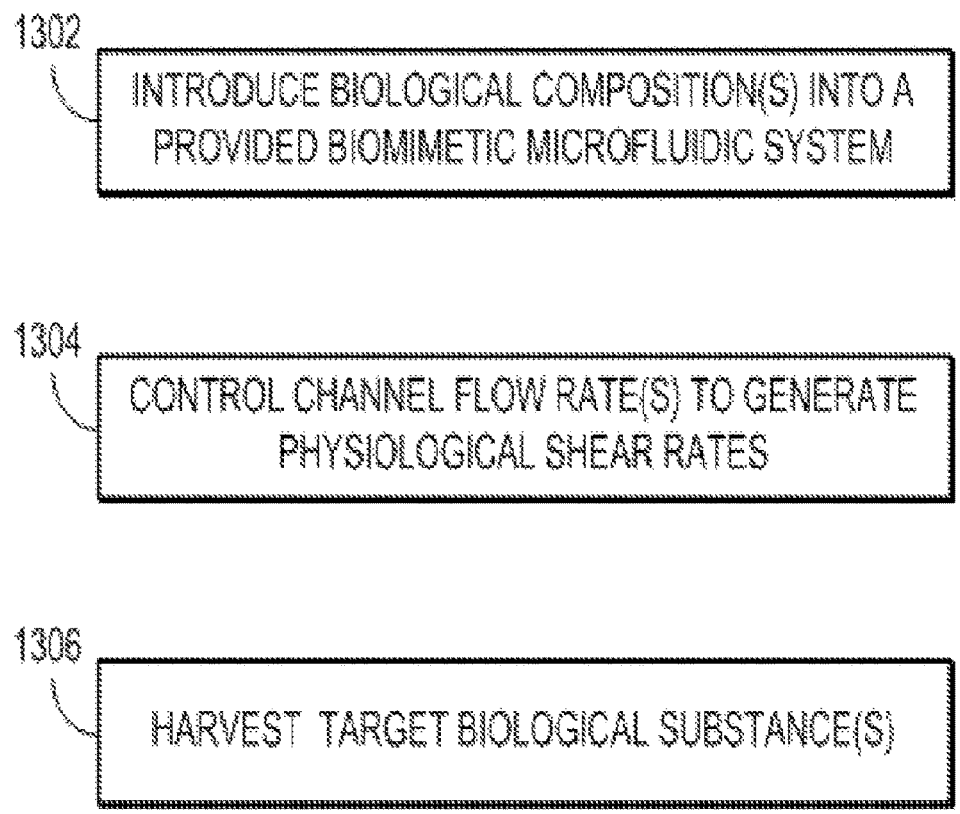
FIG. 13 is a flowchart setting forth steps of a process for producing a physiological model, in accordance with aspects of the present disclosure.

Turning to FIG. 13, steps of a process 1300 for producing a physiological model are shown, where the model may include at least one of a bone marrow and blood vessel structure. At process block 1302, any number of biological compositions may be introduced into a provided biomimetic microfluidic system as described, for example, with reference to FIGS. 1, 9 and 12. In some implementations, process block 1302 may include introducing a first biological composition into a first channel or chamber of the provided system at a first flow rate using a first source, and introducing a second biological composition into a second channel or chamber of the provided system at a second flow rate using a second source. In other implementations, the second or a third biological composition may be introduced into a third channel or chamber of the system, using the second or a third source at a third flow rate. As described, each channel or chamber may be prepared, processed and/or infused with biological compositions using any combination of sources and flows, where each biological composition can include semi-solids, solids, liquids, cells, and so forth, or a combination thereof.

At process block 1304, flow rates may be controlled in order to create desired differentials between channels or chambers. In some aspects, controlling such flow rates may generate physiological shear rates within a predetermined range that would facilitate production blood platelets. For example, such predetermined range may be between 100 s$^{-1}$ and 10,000 s$^{-1}$, and more specifically between 500 s$^{-1}$ and 2500 s$^{-1}$. In some aspects, respective directions of flow rates may be reversed, as described with reference to FIG. 11. Then, at process block 1306, target biological substances produced, for example, proximate to the microchannels configured in the provided biomimetic microfluidic system, may be harvested from the effluent. As described, such target biological substances can include blood platelets. In some aspects, the effluent may undergo a number of processing steps at process block 1306 in order to extract the target biological substances from the effluent.

Further examples of materials and methods utilized in these approaches are detailed below. It will be appreciated that the examples are offered for illustrative purposes only, and are not intended to limit the scope of the present disclosure in any way. Indeed, various modifications in addition to those shown and described herein, such as applicability to the blood brain barrier or molecular diffusion across separate mediums, may be possible. For example, specific implementations, including dimensions, configurations, materials, cell types, particulates, flow medium and flow rates, fabrication methods and recipes, as well as imaging, processing and analysis methods, and so on, are described. However, it will be appreciated that implementations may also be used, and still fall within the scope of the appended claims.

EXAMPLES

Microfluidic Device Design and Fabrication

Microfluidic devices were fabricated using soft lithography. As shown in the example of FIG. 1, the devices included two channels containing passive filters, for trapping air bubbles and dust, followed by fluid resistors, used to damp fluctuations in flow rate arising during operation. The channels merged to a rectangular area 1300 micrometers long, 130 micrometers wide, and 30 micrometers deep, separated by a series of columns (10 micrometers wide and 90 micrometers long) spaced 3 micrometers apart. To ensure efficient gas exchange and support high-resolution live-cell microscopy during cell culture, the microfluidic devices were constructed from a cell-inert silicon-based organic polymer bonded to glass slides.

AutoDesk software in AutoCAD was used to design the desired 2D pattern and printed on a photolithography chrome mask. Silicon wafers (University Wafers, Boston, Mass.) were spin coated with SU-8 3025 photoresist (Michrochem, Newton, Mass.) to a 30 micrometers film thickness (Laurel) Technologies, North Wales, Pa.), baked at 65 degrees C. for 1 minute and 95 degrees C. for 5 minutes, and exposed to UV light (~10 mJ cm$^{-2}$) through the chrome mask for 30 seconds. The unbound SU-8 photoresist was removed by submerging the substrate into propylene glycol monomethyl ether acetate for 7 minutes. Polydimethylsiloxane (PDMS) was poured onto the patterned side of the silicon wafer, degassed, and cross-linked at 65 degrees C. for ~12 hours. After curing, the PDMS layer was peeled off the mold and the inlet and outlet holes were punched with a 0.75 mm diameter biopsy punch. The channels were sealed by bonding the PDMS slab to a glass cover slide (#1.5, 0.17× 22×50 mm, Dow Corning, Seneffe, Belgium) following treatment with oxygen plasma (PlasmaPrep 2, GaLa Instrumente GmbH, Bad Schwalbach, Germany). Samples were infused into the microfluidic device via PE/2 tubing (Scientific Commodities, Lake Havasu City, Ariz.) using 1 mL syringes equipped with 27-gauge needles (Beckton Dickinson, Franklin Lakes, N.J.). Flow rates of liquids were controlled by syringe pumps (PHD 2000, Harvard Apparatus, Holliston, Mass.).

Microfluidic Device Operation

Devices were coated with a 0.22 μm filtered 10% BSA solution (Millipore, Billerica, Mass.) for 30 minutes to prevent direct cell contact with glass. Referring to FIG. 1, primary MKs and media were infused in the first inlet 118 and second inlet 122, respectively, at a rate of 12.5 μL/hour using a two-syringe microfluidic pump (Harvard Apparatus, Holliston, Mass.). When the first outlet 120 was closed, both input solutions were redirected toward the second outlet 124 causing primary MKs to trap.

Extracellular Matrix Composition Modeling (2D)

Microfluidic devices were selectively coated with extracellular matrix proteins by perfusing the channels with rhodamine-conjugated fibrinogen (1 mg/mL) or fibronectin (50 μg/mL, Cytoskeleon Inc., Denver, Colo.) for 30 minutes. Samples were perfused in parallel through both inlets and collected through both outlets so that laminar flow streams did not mix. Devices were washed with 1×PBS and coated with 0.22 μm filtered (Millipore, Billerica, Mass.) 10% BSA solution (Roche, South San Francisco, Calif.) for 30 minutes to coat any remaining exposed glass.

BM Stiffness Modeling (3D)

Primary MKs were re-suspended in 1% sterile alginate with an average molecular weight of 150-250 kD (Pronova SLG100, FMC biopolymer, Norway) in culture media and perfused across the microfluidic device (first inlet 118, second outlet 124 in FIG. 1) until MKs became trapped. The second channel was then selectively perfused with 1×PBS to remove alginate from this channel. To make a homogenous alginate gel, 30 mM nanoparticle calcium carbonate (mkNANO, Canada) was used as a calcium source and dissolved in 60 mM slowly hydrolyzing D-Glucono-δ-lactone (Sigma-Aldrich, St. Louis, Mo.), which releases the calcium in the solution (in review Khavari et al NJP 2013). The calcium carbonate suspension was perfused along the second channel until the alginate solution retained in the first channel became polymerized (~20 minutes). The second channel was then selectively washed with 1×PBS and replaced with culture media. To determine the alginate gel's mechanical properties 0.25 percent, 0.5 percent, 1.0 percent, and 2.0 percent alginate gels were prepared and their frequency-dependent shear moduli were measured by rheology at 37° C. (Ares G2 TA instruments, New Castle, Del.).

Sinusoidal Blood Vessel Contact Modeling (3D)

Microfluidic devices were selectively coated with 50 μg/mL fibronectin (Cytoskeleon Inc., Denver Colo.) and 10 percent BSA (Roche, South San Francisco, Calif.), as described above, and transferred to a 37 degrees C., 5 percent CO2 incubator. 10,000,000 HUVECs/mL in EBM media (Lonza, Basel, Switzerland) were seeded over the fibronectin-coated channel at 12.5 uL/hour and permitted to adhere to this surface over a period of 3 hours. The inlet sample was replaced with cell-free EBM media and perfused through the channel until HUVECs reached confluency (2-8 days). Cells were stained with 5 μM CellTracker Red and 1 μg/mL Hoescht 33342 (Invitrogen, Carlsbad, Calif.) for 45 minutes, washed in fresh media or fixed in 4% formaldehyde and visualized by confocal-fluorescence microscopy.

Vascular Shear Rate Modeling (3D)

The shear stresses imparted on the MKs were estimated with a computational model of the fluid dynamics within the microfluidic device. A commercial finite element method software (COMSOL) was used to solve the Navier-Stokes equation. The steady-state Navier Stokes flow equation for incompressible flow is:

$$\rho(\vec{v}\cdot\vec{\nabla}\vec{v}) = -\vec{\nabla}p + \mu\vec{\nabla}^2\vec{v} + f \qquad (1)$$

where $\rho$ is the fluid density, $\vec{v}$ is the flow velocity, p is the pressure, $\mu$ is the fluid viscosity and f is the body forces action on a fluid. Equation (1) was solved in a three dimensional computational domain replicating the exact dimensions of the microfluidic device. It was assumed that the fluid within the device had a viscosity and density of water (0.001 Pa s and 1000 kg/m3, respectively). No slip boundary conditions were assumed at the walls of the channels. The infusion flow rates ranged from 12.5-200 μL/hr. A triangular mesh, which was made finer at the slits, was used to discretize the domain. The model contained 315,317 degrees of freedom. Mesh independence, as was confirmed by obtaining less than a 10 percent difference between shear rates, was found between 251,101 and 415,309 degrees of freedom. The steady state solutions were obtained using the UMFPACK linear system solver.

Primary Mouse Megakaryocyte Culture

Mouse FLCs were collected from WT CD1 mice (Charles River Laboratories, Wilmington, Mass.) and MKs were cultured.

Electron Microscopy

Megakaryocyte input and bioreactor effluent were fixed with 1.25 percent paraformaldehyde, 0.03 percent picric acid, 2.5 percent glutaraldehyde in 0.1-M cacodylate buffer (pH 7.4) for 1 h, post-fixed with 1% osmium tetroxide, dehydrated through a series of alcohols, infiltrated with propylene oxide, and embedded in epoxy resin. Ultrathin sections were stained and examined with a Tecnai G2 Spirit BioTwin electron microscope (Hillsboro, Oreg.) at an accelerating voltage of 80 kV. Images were recorded with an Advanced Microscopy Techniques (AMT) 2-K charged coupled device camera, using AMT digital acquisition and analysis software (Advanced Microscopy Techniques, Danvers, Mass.).

Immunofluorescence Microscopy

Megakaryocytes, released proPLTs, or bioreactor effluent were purified and probed. Samples were either incubated with 5 μM CellTracker Green (Invitrogen, Carlsbad, Calif.) for 45 minutes, washed in fresh media and visualized by live-cell fluorescence microscopy, or fixed in 4% formaldehyde and centrifuged onto poly-L-lysine (1 μg/mL)-coated coverslides. For analysis of cytoskeletal components, samples were permeabilized with 0.5 percent Triton-X-100, and blocked in immunofluorescence blocking buffer (0.5 g BSA, 0.25 ml 10% sodium azide, 5 ml FCS, in 50 ml 1×PBS) overnight before antibody labeling (55). To delineate the microtubule cytoskeleton, samples were incubated with a rabbit polyclonal primary antibody for mouse or human β1-tubulin. To delineate the actin cytoskeleton, samples were incubated with Alexa 568 phalloidin (Invitrogen, Carlsbad, Calif.). Cell nuclei were labeled with 1 μg/mL Hoescht 33342 (Invitrogen, Carlsbad, Calif.). To correct for background fluorescence and nonspecific antibody labeling, slides were incubated with the secondary antibody alone, and all images were adjusted accordingly. Samples were examined with a Zeiss Axiovert 200 (Carl Zeiss, Thornwood, N.Y.) equipped with 10× (numerical aperature, 0.30) Plan-Neofluar air and 63× (numerical aperature, 1.4) Plan-ApoChromat oil immersion objectives, and images were obtained using a CCD camera (Hamamatsu Photonics, Boston, Mass.). Images were analysed using the Metamorph version 7.7.2.0 image analysis software (Molecular Devices, Sunnyvale, Calif., USA) and ImageJ version 1.47p software (NIH, http://rsb.info.nih.gov.ezp-prod1.hul.harvard.edu/ij/).

Cell Size and Morphology Determination

Cells were individually thresholded and high-content cytoplasmic area and perimeter measurements were performed in ImageJ using investigator-coded software, outlined below. Analysis was confirmed by manual inspection of all samples, and improperly thresholded cells were excluded from the analysis. MK diameters were calculated from area measurements to account for non-circular cells. More than 2000 cells were counted for each condition, and analysis of MK area and effluent composition was performed for at least three independent samples. Statistical significance was established using a 2-tailed Student t test for paired samples. Error bars represent one standard deviation about the mean.

Live Cell Microscopy

For shear cultures, MKs were loaded onto 'naked' microfluidic devices (only BSA-coated), and the infusion rate was doubled incrementally from 12.5 µL/hr to 200 µL/hr over a 2 hour period. For static cultures, isolated MKs were pipetted into chambers formed by mounting a glass coverslide coated with 3% BSA onto a 10 mm petri dish with a 1 cm hole and cultured for 24 hours. Both static and shear cultures were maintained at 37 degrees C. and 5 percent CO2 and examined on a Zeiss Axiovert 200 (Carl Zeiss, Thornwood, N.Y.) equipped with 10× (numerical aperature, 0.30) Plan-Neofluar air objective. Differential interference contrast (DIC) images were obtained using CCD camera (Hamamatsu Photonics, Boston, Mass.) at either 2 second (shear cultures) or 20 minute (static cultures) intervals. Images were analyzed using the Metamorph version 7.7.2.0 image analysis software (Molecular Devices, Sunnyvale, Calif., USA) and ImageJ software version 1.47p. ProPLT extension rates were determined manually for over 200 MKs from at least three independent samples. For PLT spreading experiments, effluent was collected from microfluidic devices after 2 hours and pipetted into uncoated static culture chambers, described above. PLTs were permitted to contact glass by gravity sedimentation and spreading was captured at 5 second intervals over a 5 minute period.

GFP-β1 Tubulin Retro Viral Transfection

Dendra2-fused β1 tubulin was cloned into pMSCV plasmids. HEK 293 cells packaging cells were cultured in DMEM supplemented with 10% fetal bovine serum (FBS) to 30-50 percent confluency. Transfection of HEK 293 cells was performed using 2 µg of DNA plasmids encoding gag/pol, vsvG, and the β1 tubulin fused with Dendra2 in the pMSCV vector. After medium exchange the following day, cells were incubated for 72 hours for virus production. The supernatant was filtered through a 0.22 µm filter (Millipore, Billerica, Mass.), and aliquots were stored at −80 degrees C. On the second day of culture, MKs isolated from fetal liver cultures described above were resuspended in DMEM containing 10 percent FBS, 8 µg/mL polybrene (Sigma), and the retroviral supernatant. Samples were transferred to a 6-well plate, centrifuged at 800×g for 90 minutes at 25 degrees C. and then incubated at 37 degrees C. for 90 minutes. Following incubation, MKs were washed by centrifugation and resuspended in fresh DMEM containing 10 percent FBS and TPO. MKs were allowed to mature until day 4 of culture and then isolated by a BSA gradient, as previously described.

Flow Cytometry

Platelets were collected from the released proPLT fraction of static MK cultures or bioreactor effluent and examined under resting conditions. Samples were probed with FITC-conjugated antibodies against CD42a or CD41/61 (Emfret Analytics, Eibelstadt, Germany) and run on a FACSCalibur flow cytometer (Beckton Dickinson). PLTs were gated by their characteristic forward- and side-scattering as they passed through the detector, and their total fluorescence intensity was calculated after subtraction of a FITC-conjugated IgG antibody specificity control (Emfret Analytics). Quantization of PLT yield was determined by dividing net GP IX+PLT production by net GP IX+MK depletion over effluent collection period, and was performed for at least 3 independent samples Results were identical for GP IIbIIIa+ cells.

Image Analysis

The digital images acquired in Metamorph were analyzed using ImageJ and Adobe Photoshop CS3 (Adobe Systems, San Jose, Calif.). Dividing lines explicitly separate different images, or separate regions of the same image. No specific features within an image were enhanced, obscured, moved, removed, or introduced, and adjustments made to the brightness, contrast, and color balance were linearly applied to the whole image.

Microfluidic Device Models Physiological Characteristics of Human BM

Figure 2A:
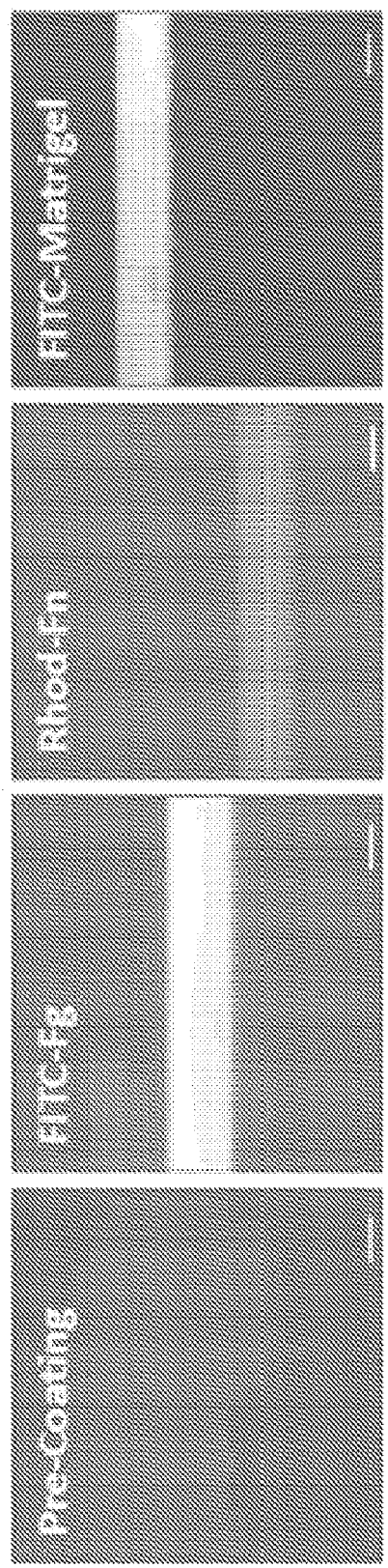
FIG. 2A shows microscopy images depicting microfluidic channels coated with bone marrow and blood vessel proteins for reproducing extra-cellular matrix (ECM) composition.
Figure 2B:
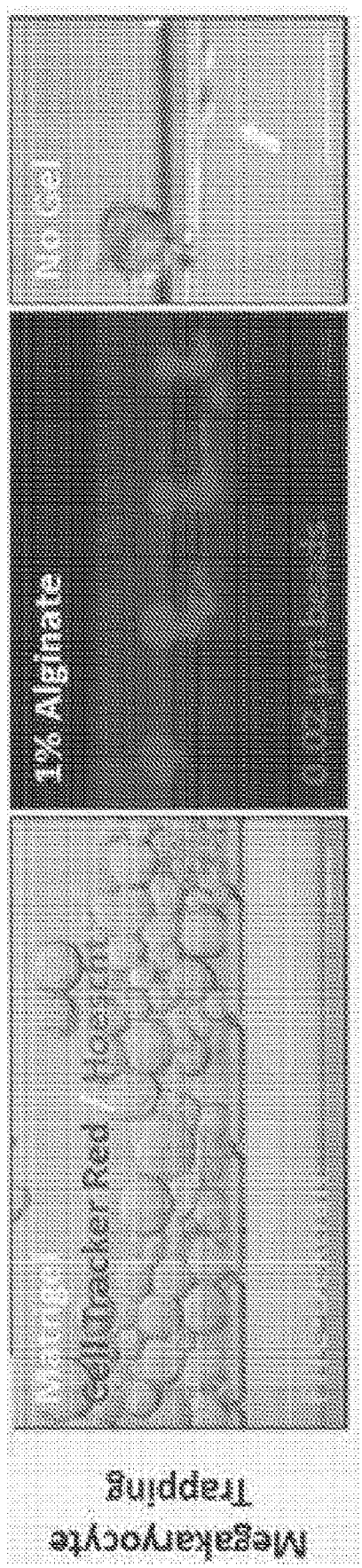
FIG. 2B shows microscopy images depicting megakaryocytes (MKs) trapped in microchannels selectively embedded in alginate gel, modeling 3-dimensional ECM organization and physiological bone marrow (BM) stiffness.

To recapitulate physiological conditions, each of the channels were selectively coated with fibrinogen and fibronectin, respectively to reproduce ECM composition of the BM and blood vessel microenvironments (shown in FIG. 2A). By running flow across the microfluidic device, primary MKs infused along a first channel would become sequentially trapped between the columns and extend proPLTs into the second channel (shown in FIG. 2B), recapitulating physiological proPLT extension. To model 3D ECM organization and physiological BM stiffness (250 Pa), MKs were infused in a 1 percent alginate solution that was polymerized within the microfluidic device, selectively embedding the MKs in alginate gel within the first channel while retaining vascular flow in the second channel. Alginate did not inhibit proPLT production, and MK distance from the second channel could be controlled.

Figure 2C:
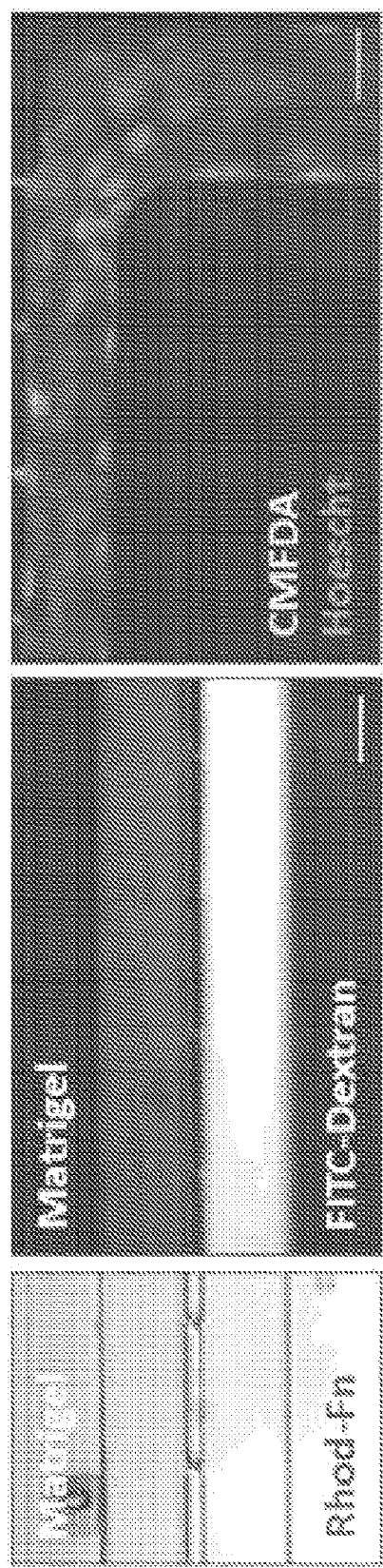
FIG. 2C shows microscopy images of human umbilical vein endothelial cells (HUVECs) selectively cultured in the fibrinogen-coated second channel to produce a functional blood vessel.
Figure 2D:
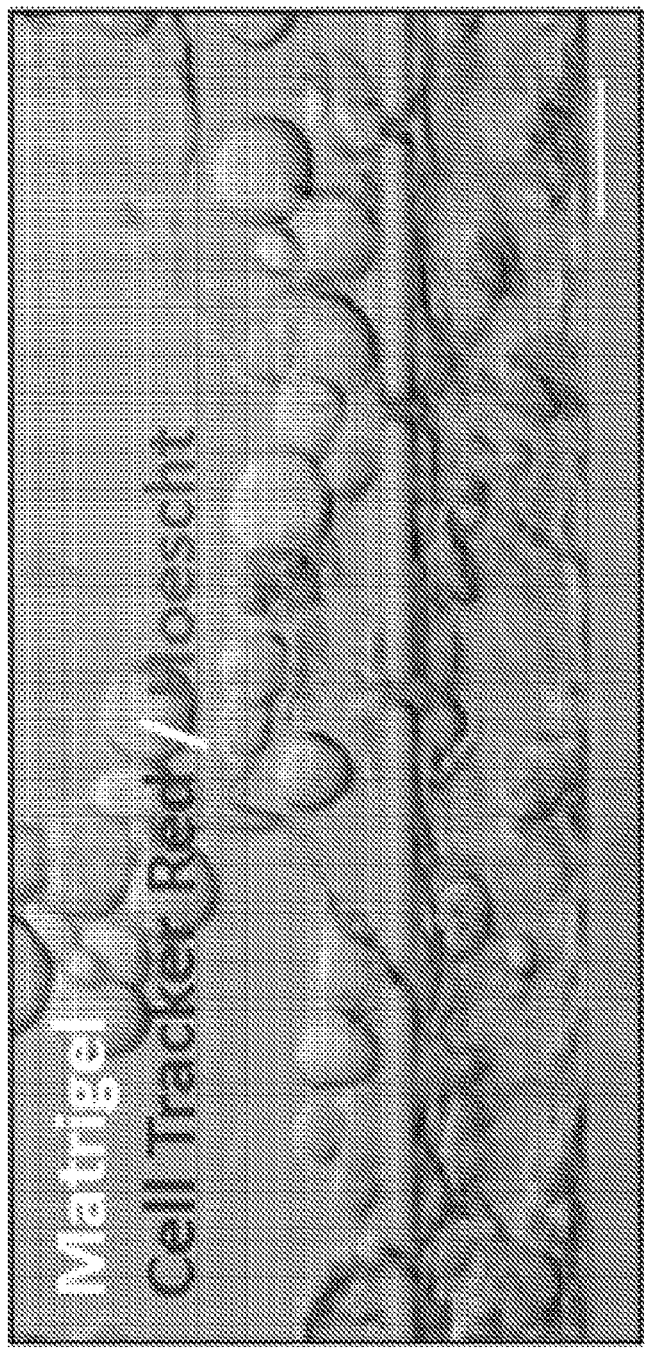
FIG. 2D shows an image of a complete system for producing functional blood platelets (PLTs).
Figure 2E:
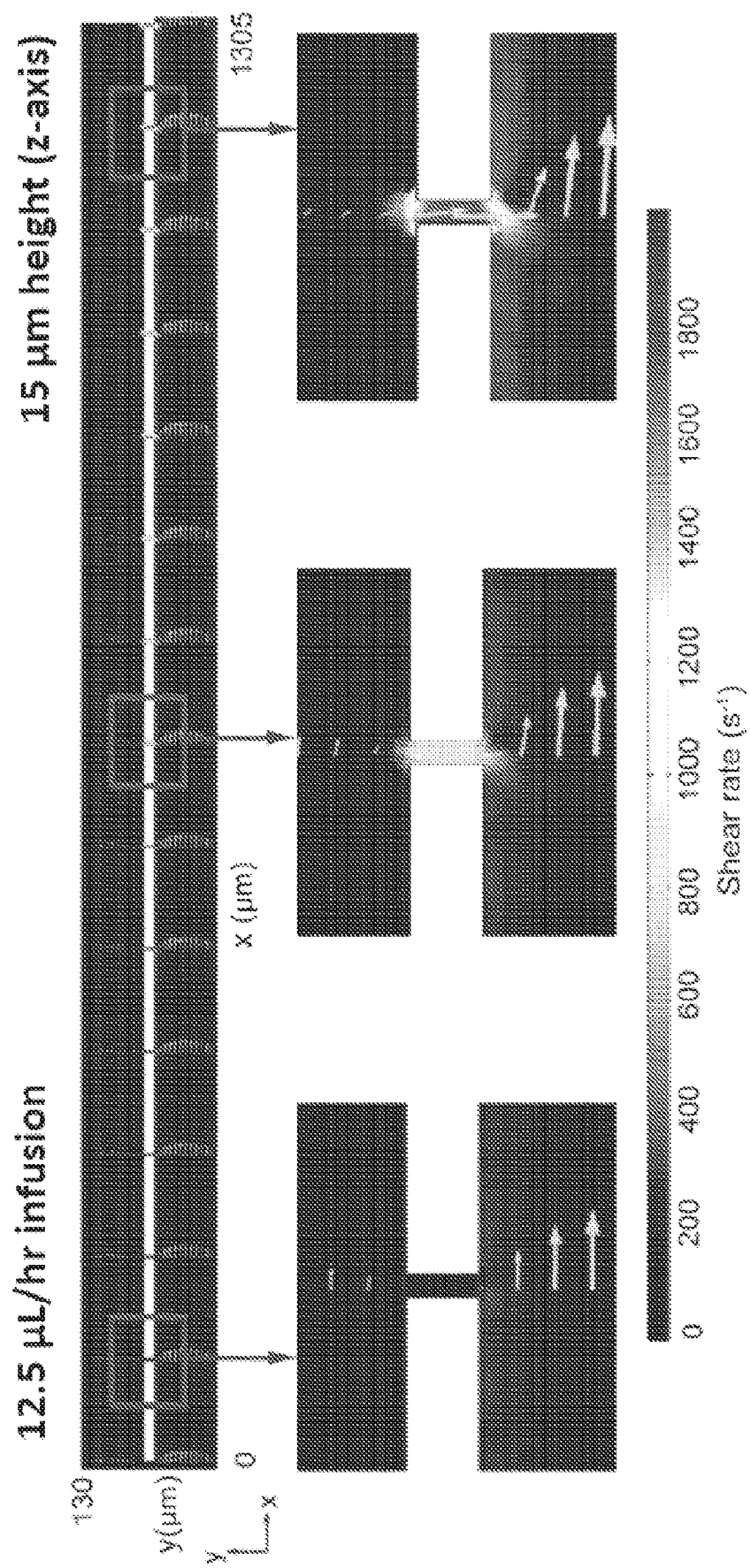
FIG. 2E shows a graphical depiction of a simulated distribution of shear rates within a biomimetic microfluidic system in accordance with aspects the present disclosure.
Figure 2F:
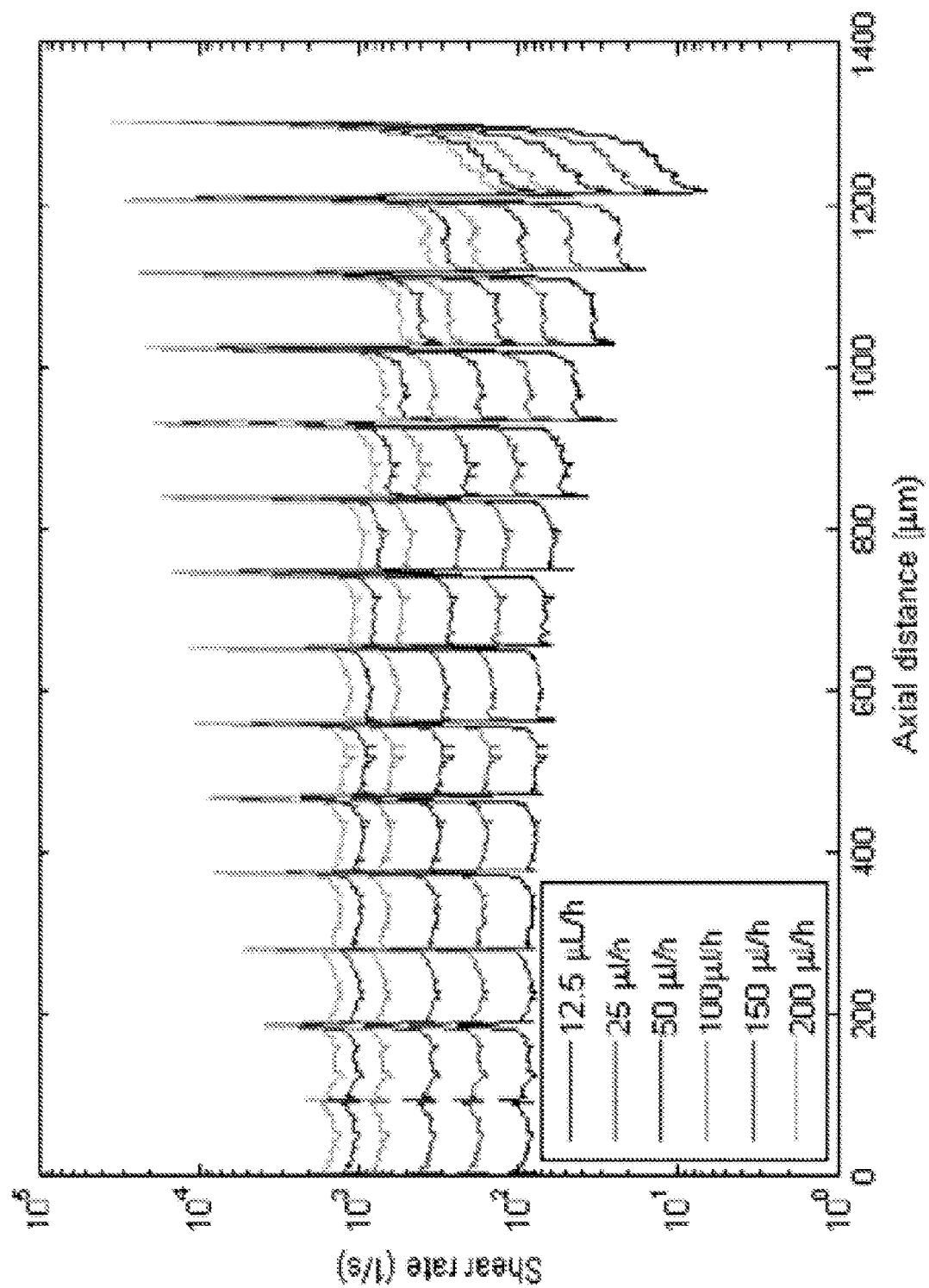
FIG. 2F shows a graph showing shear rates as a function of transverse distance from first channel for several infusion rates.
Figure 2G:
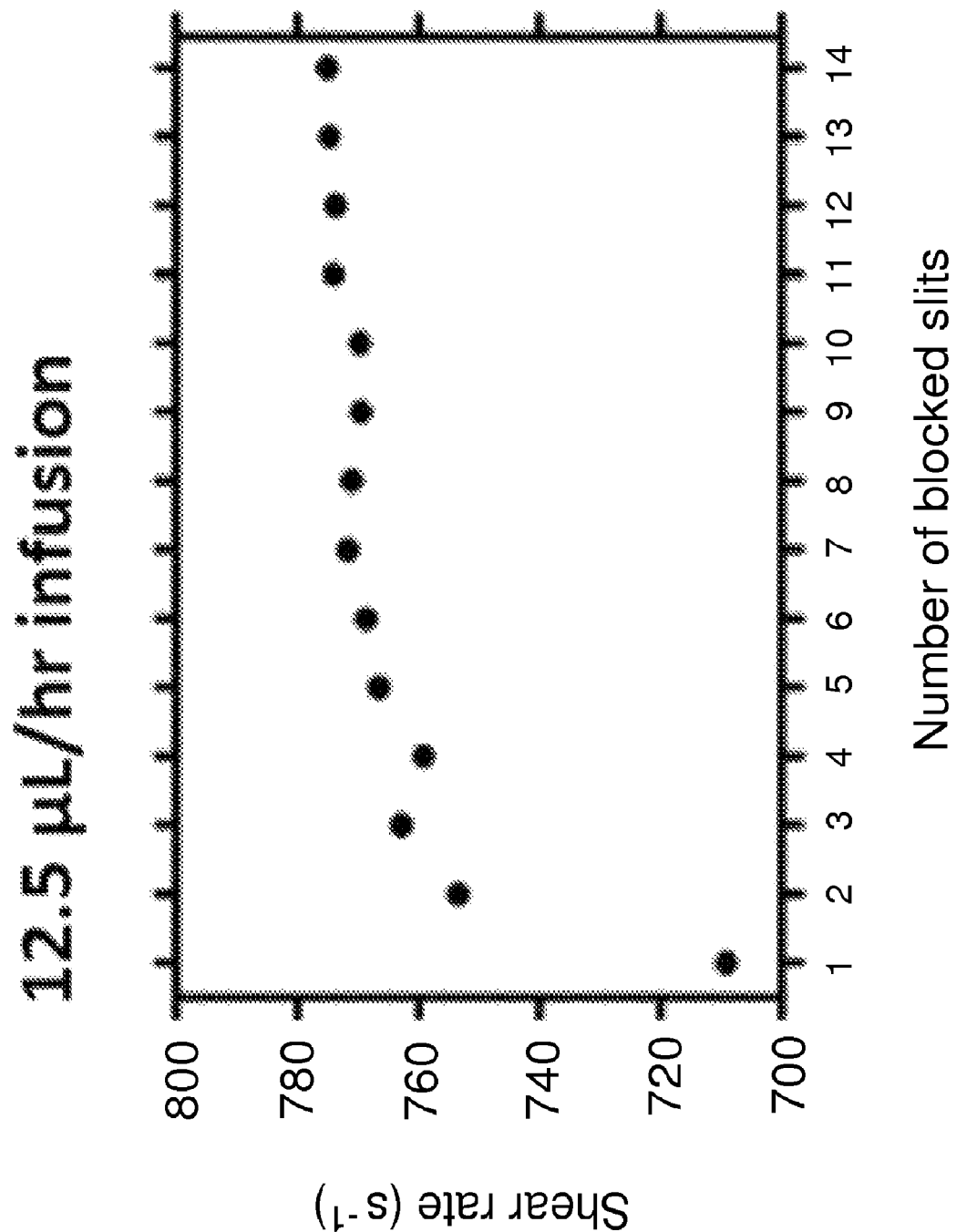
FIG. 2G shows a graph showing shear rates as a function of the number of block microchannels.

Human umbilical vein endothelial cells (HUVECs) were selectively seeded along the second channel, and grown to confluency to produce a functional blood vessel (shown in FIG. 2C). In addition, MK behavior was monitored by 10×-150× magnification, high-resolution live-cell microscopy, and the released PLTs were collected from the effluent. FIG. 2D shows the complete system illustrating operation. Laminar fluid shear rates were characterized (shown in FIG. 2E), and were tightly controlled using two microfluidic pumps (one for the first channel and one for the second channel). Shear rates within the device were linearly proportional to infusion rates and were adjusted to span the physiological range (500-2500 $s^{-1}$). While shear rates at empty microchannel junctions increased with distance from the first channel (shown in FIG. 2F), upon a MK trapping, flow was redirected to the next available gap such that MKs continued to experience physiological (between 760 and 780 $s^{-1}$) shear rates at these sites (shown in FIG. 2G).

Vascular Shear Triggers proPLT Production, Physiological Extension, and Release

Figure 3A:
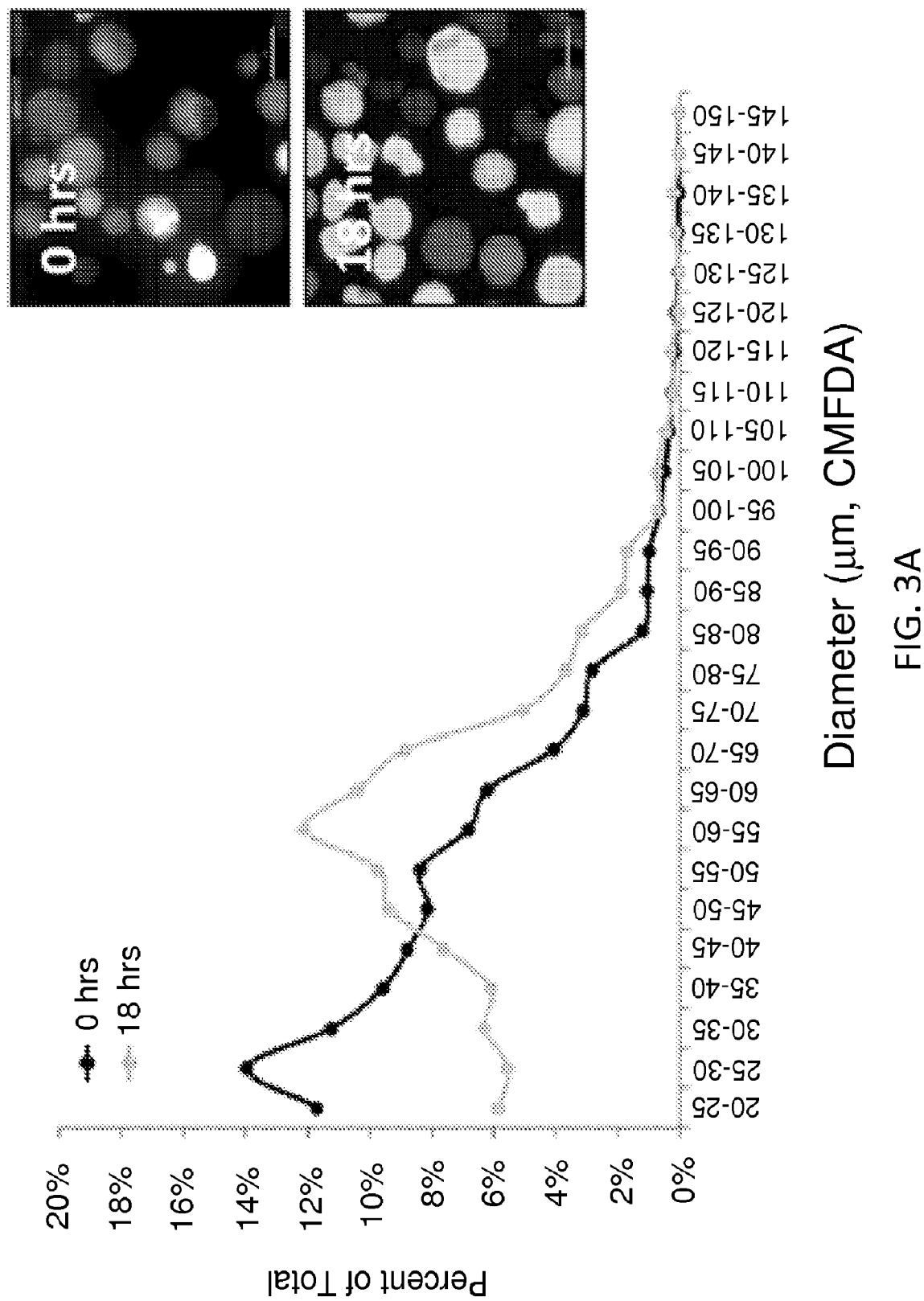
FIG. 3A shows a graph showing diameter distribution of cultured MKs at 0 and 18 hours.

In vivo BM MKs extend proPLTs in the direction of blood flow and release PLTs, proPLTs, large cytoplasmic fragments (prePLTs), and even whole MKs into sinusoidal blood vessels which may be trapping in the pulmonary microvascular bed, or otherwise maturing in the circulation. To determine the effect of physiological shear on PLT production, mouse fetal liver culture-derived (mFLC) MKs were isolated on culture day 4 and characterized by size and ploidy before being infused into the microfluidic device (shown in FIG. 3A).

Figure 3B:
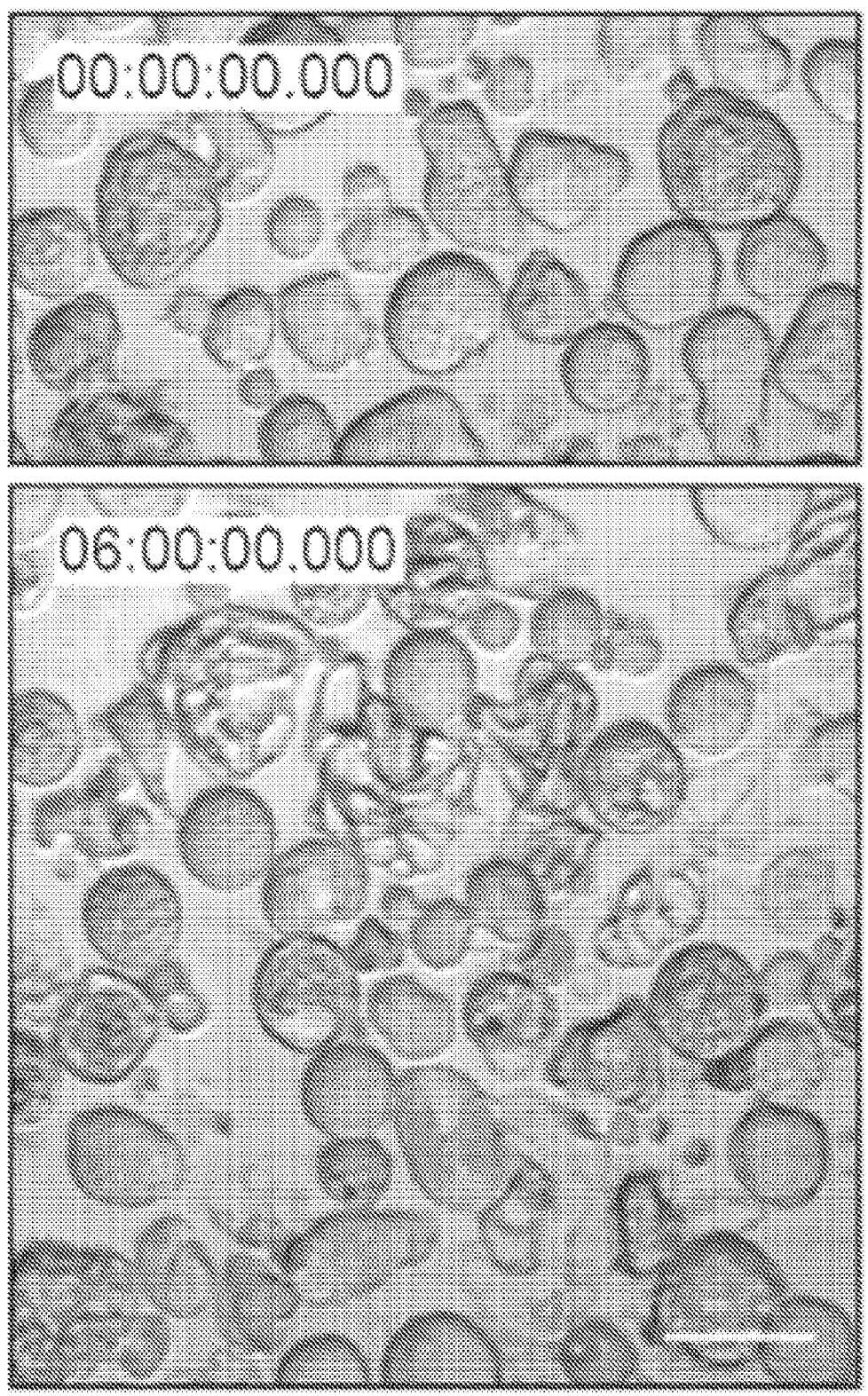
FIG. 3B shows microscopy images of MKs in static culture illustrating production of proPLTs at 6 hours post-purification.
Figure 3C:
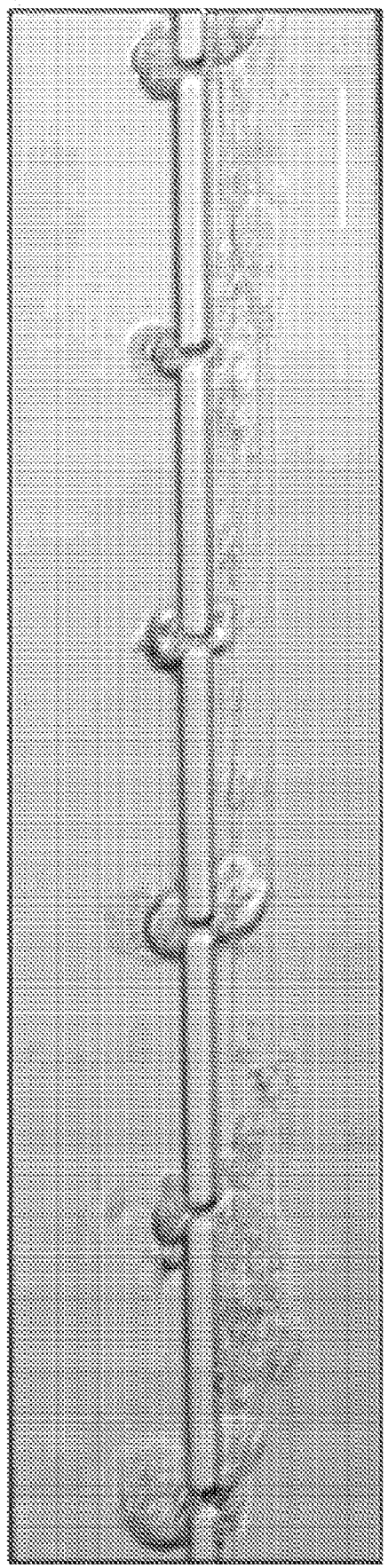
FIG. 3C shows a microscopy image showing the production proPLT under physiological shear immediately upon MK trapping.
Figure 3D:
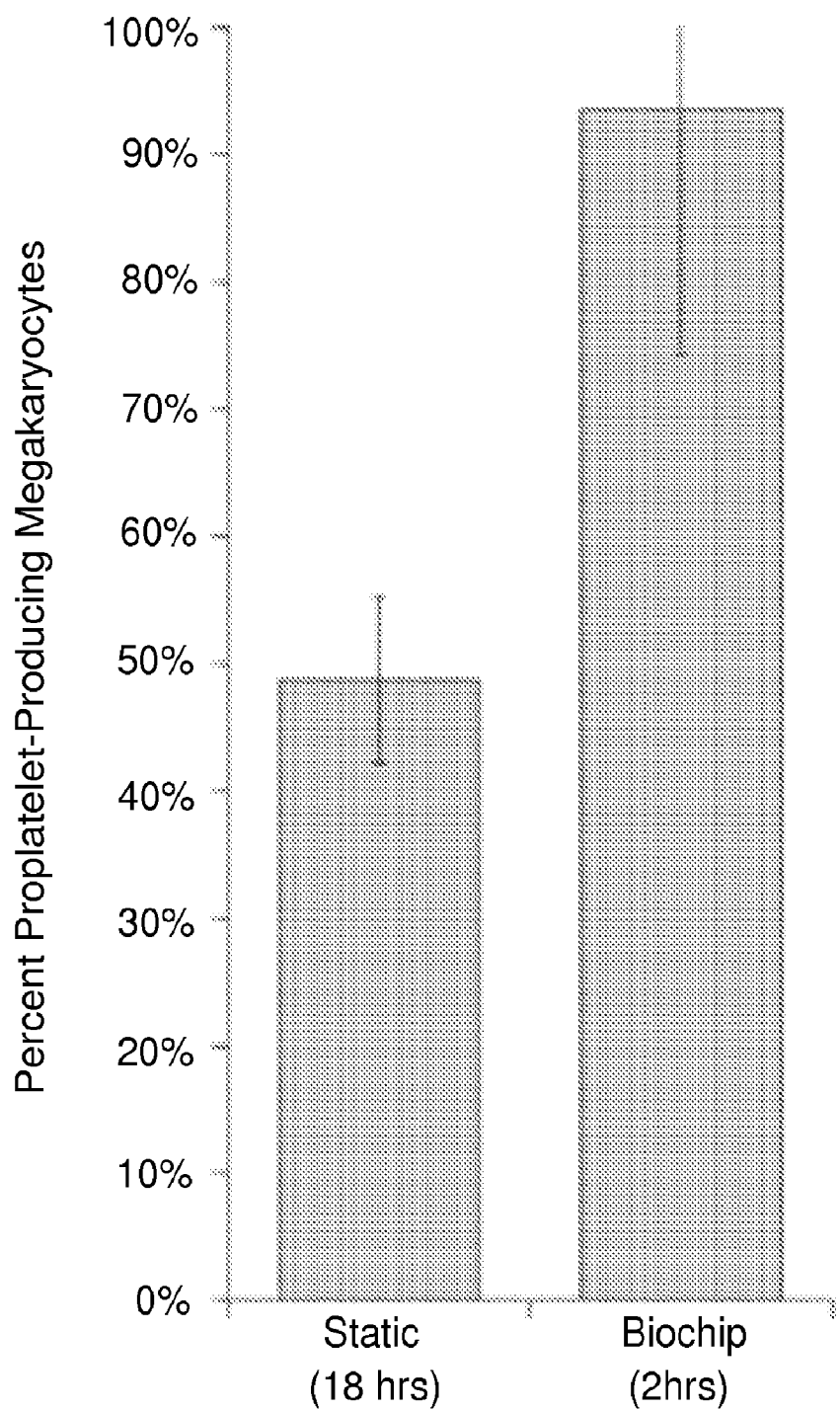
FIG. 3D shows a graph showing increased proPLT-producing MKs obtained under physiological shear versus those from static cultures.

One of the major challenges in producing transfuseable PLTs in vitro has been identifying factors that trigger proPLT production. Under static conditions MKs begin producing proPLTs ~6 hours post-isolation, and reach maximal proPLT production at 18 hours (shown in FIG. 3B). By comparison, MKs under physiological shear (shown in FIG. 3C at roughly 500 $s^{-1}$) began producing proPLTs within seconds of trapping, reaching maximal proPLT production and biochip saturation within the first 2 hours of culture. MKs cultured under physiological shear produced fewer, longer proPLTs that were less highly branched relative to static cultures. ProPLTs in shear cultures were uniformly extended into the lower channel and aligned in the direction of flow against the vascular channel wall, recapitulating physiological proPLT production. The percent of proPLT-producing MKs under physiological shear were doubled over static cultures to roughly 90% (shown in FIG. 3D).

Figure 3E:
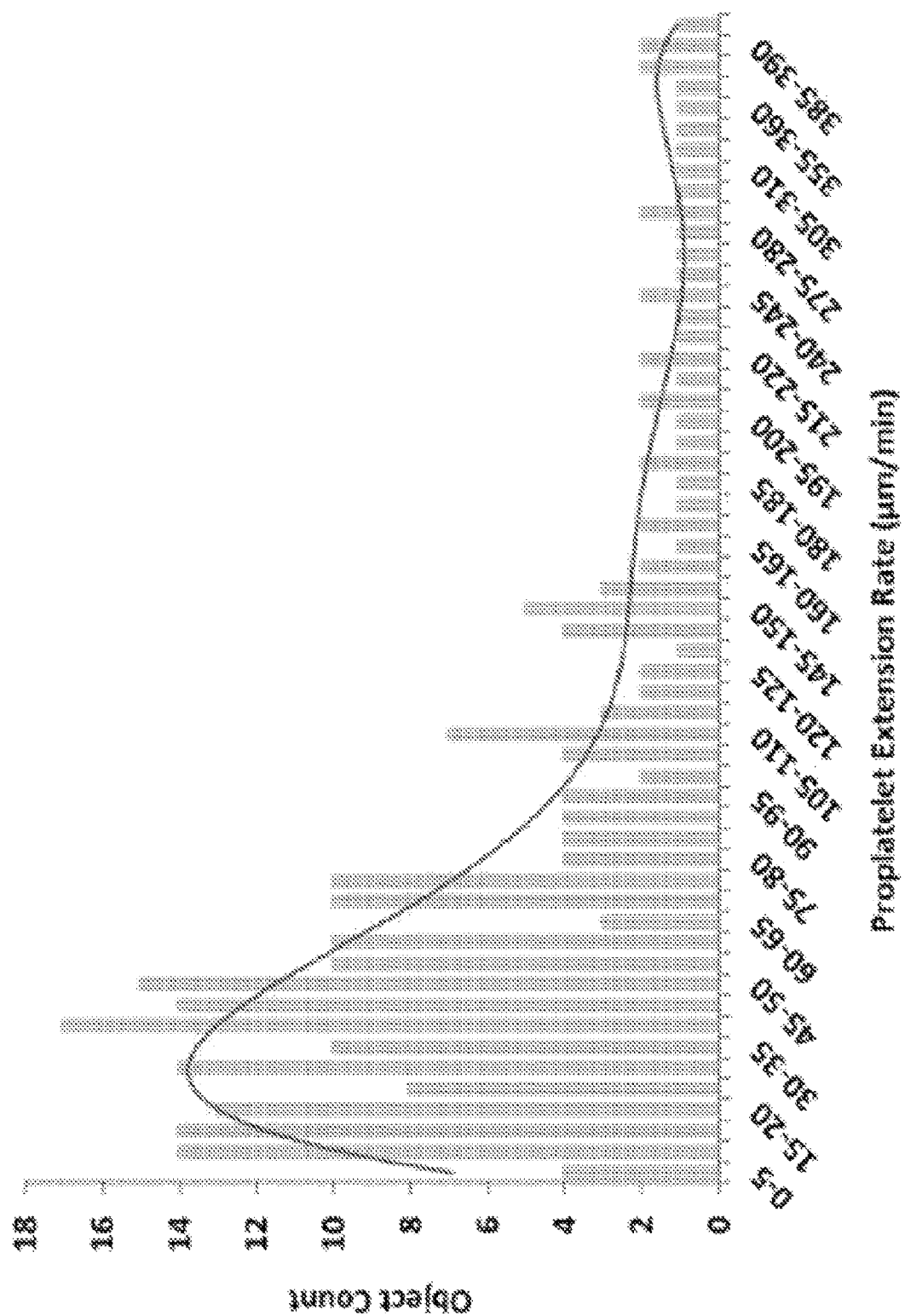
FIG. 3E shows a graph showing proPLT extension rates under physiological shear.

Another major challenge in generating clinical numbers of PLTs for infusion has been that in vitro cultures extend proPLTs at a significantly slower rate than what has been observed in vivo. Application of physiological shear in our microfluidic device increased proPLT extension rate by an order of magnitude above static culture controls to roughly 30 µm/min (shown in FIG. 3E), which agrees with physiological estimates of proPLT extension rate from intravital microscopy studies in living mice and support increased PLT production in vitro.

Figure 4A:
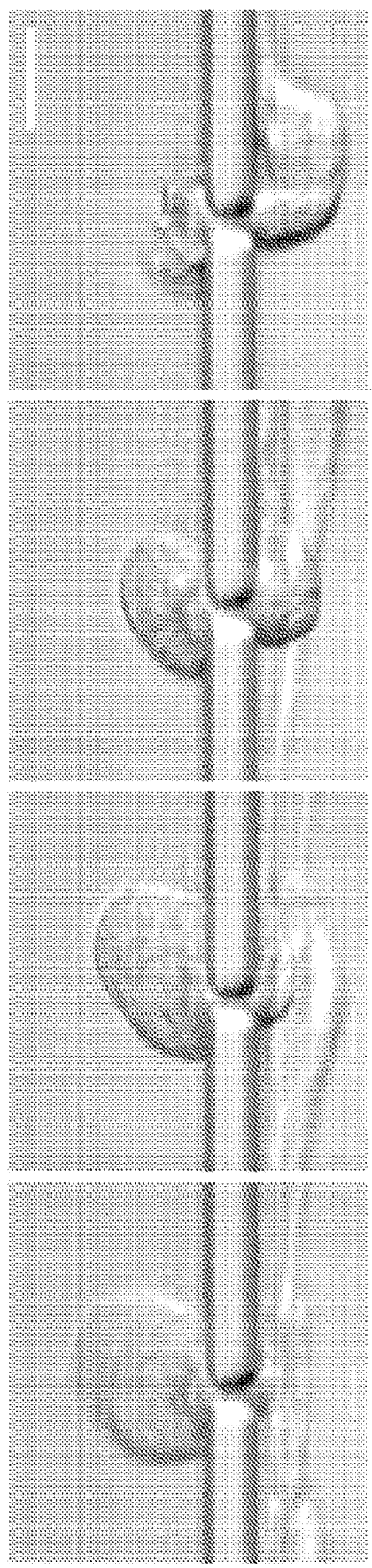
FIG. 4A shows microscopy images that illustrate MKs squeezing through 3 µm-wide microchannels.
Figure 4B:
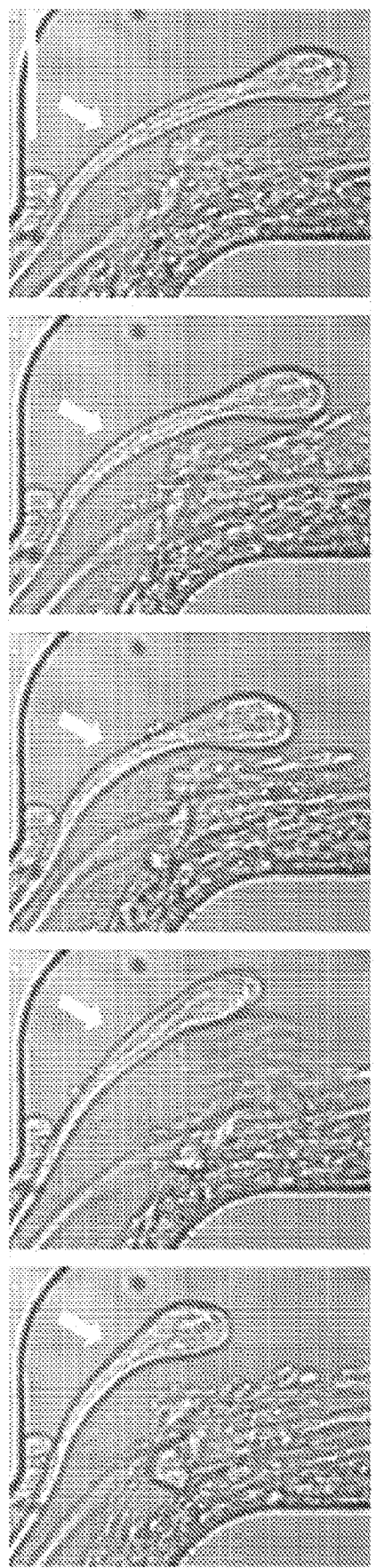
FIG. 4B shows microscopy images that illustrate MKs extending large fragments through 3 µm-wide microchannels.

Early histological studies in both humans and mice have predicted that whole MKs, as well as MK fragments may be squeezing through gaps or fenestrations in the vascular endothelium lining BM blood vessels to trap in the pulmonary circulatory bed. Large PLT intermediates called prePLTs were recently discovered in blood, and venous infusion of mBM- and FLC-derived MKs and prePLTs into mice produced PLTs in vivo. In the present study, 100 µm+diameter MKs were routinely observed squeezing through 3 µm (shown in FIG. 4A) and 1.5 µm gaps, or extending large MK fragments (shown in FIG. 4B), supporting a model of vascular PLT production. In addition, abscission events were routinely captured by high-resolution live-cell microscopy and occurred at variable positions along the proPLT shaft, releasing both prePLT-sized intermediates (3-10 µm diameter) and PLTs (1.5-3 µm diameter) (shown in FIG. 4C and FIG. 4D). Following each abscission, the resulting proPLT end formed a new PLT-sized swelling at the tip, which was subsequently extended and released, repeating the cycle (shown in FIG. 4E).

Figure 4C:
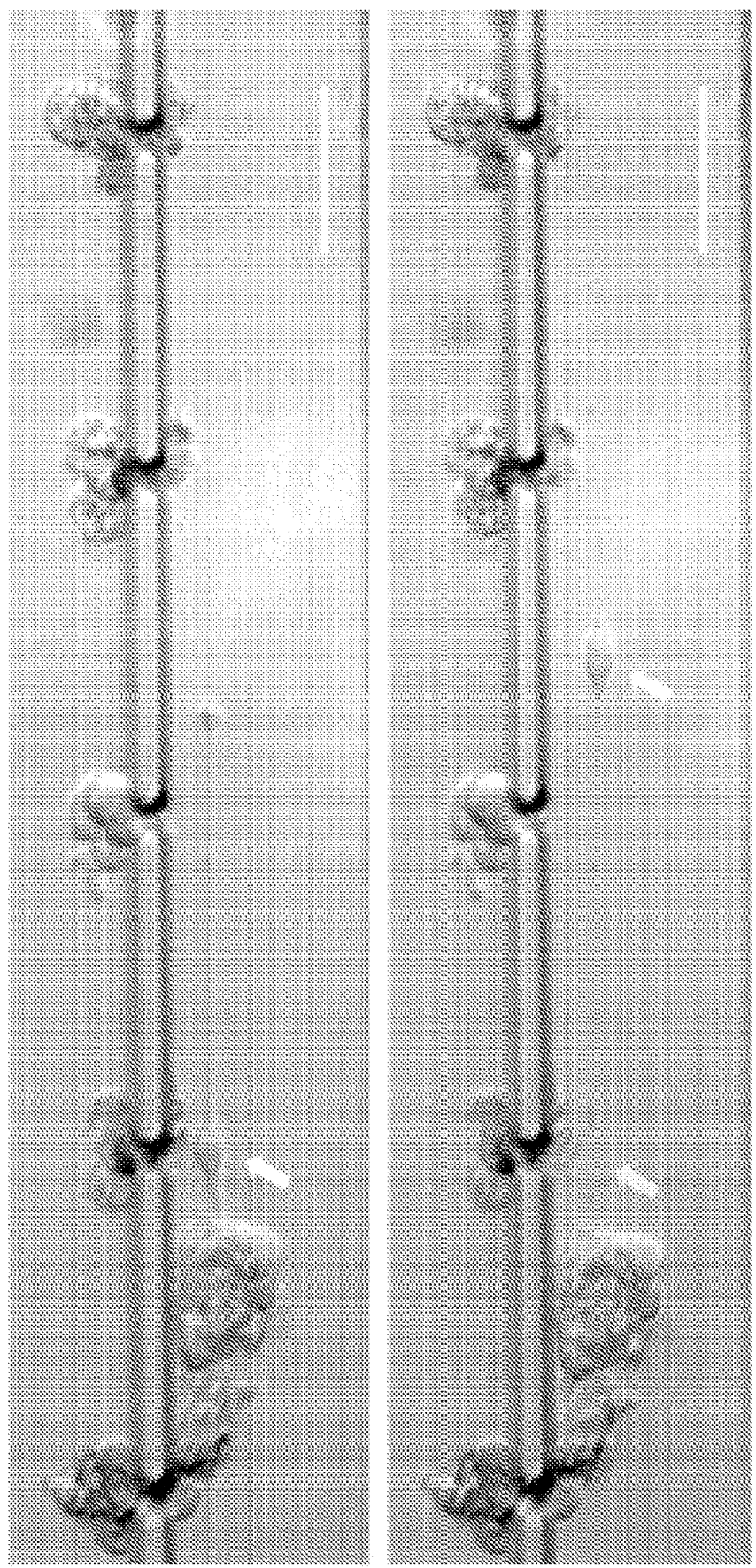
FIG. 4C shows microscopy images that illustrate proPLT extension.
Figure 4D:
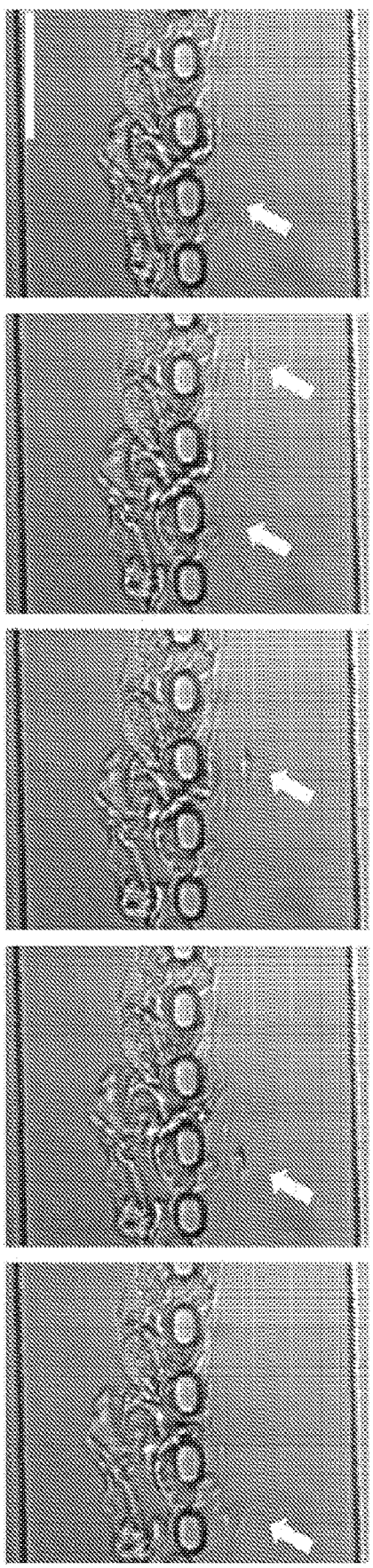
FIG. 4D shows microscopy images that illustrate proPLT extension and abscission events at different positions along the proPLT shaft.
Figure 4E:
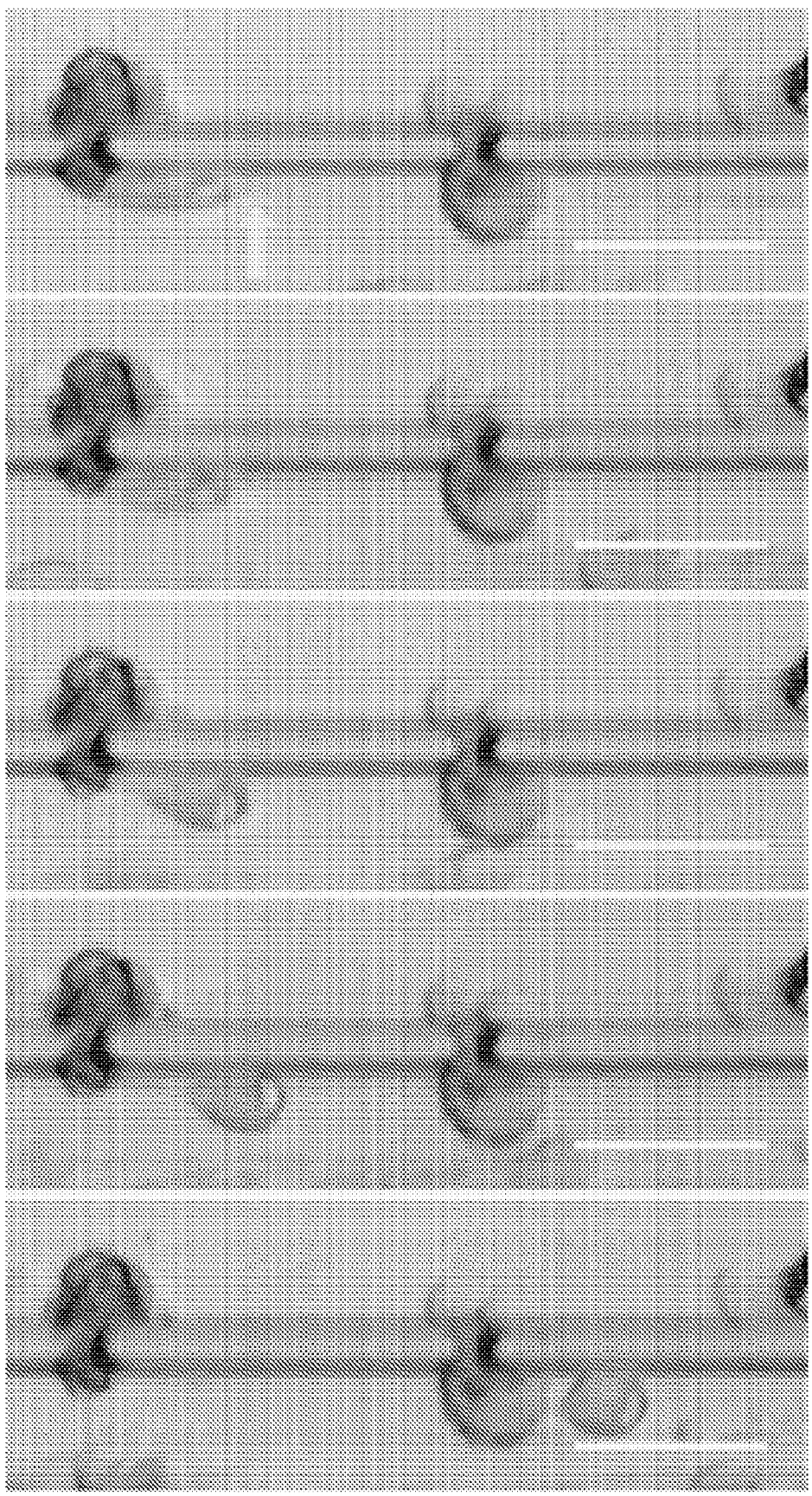
FIG. 4E shows microscopy images that illustrate the cycle of PLT production.
Figure 4F:
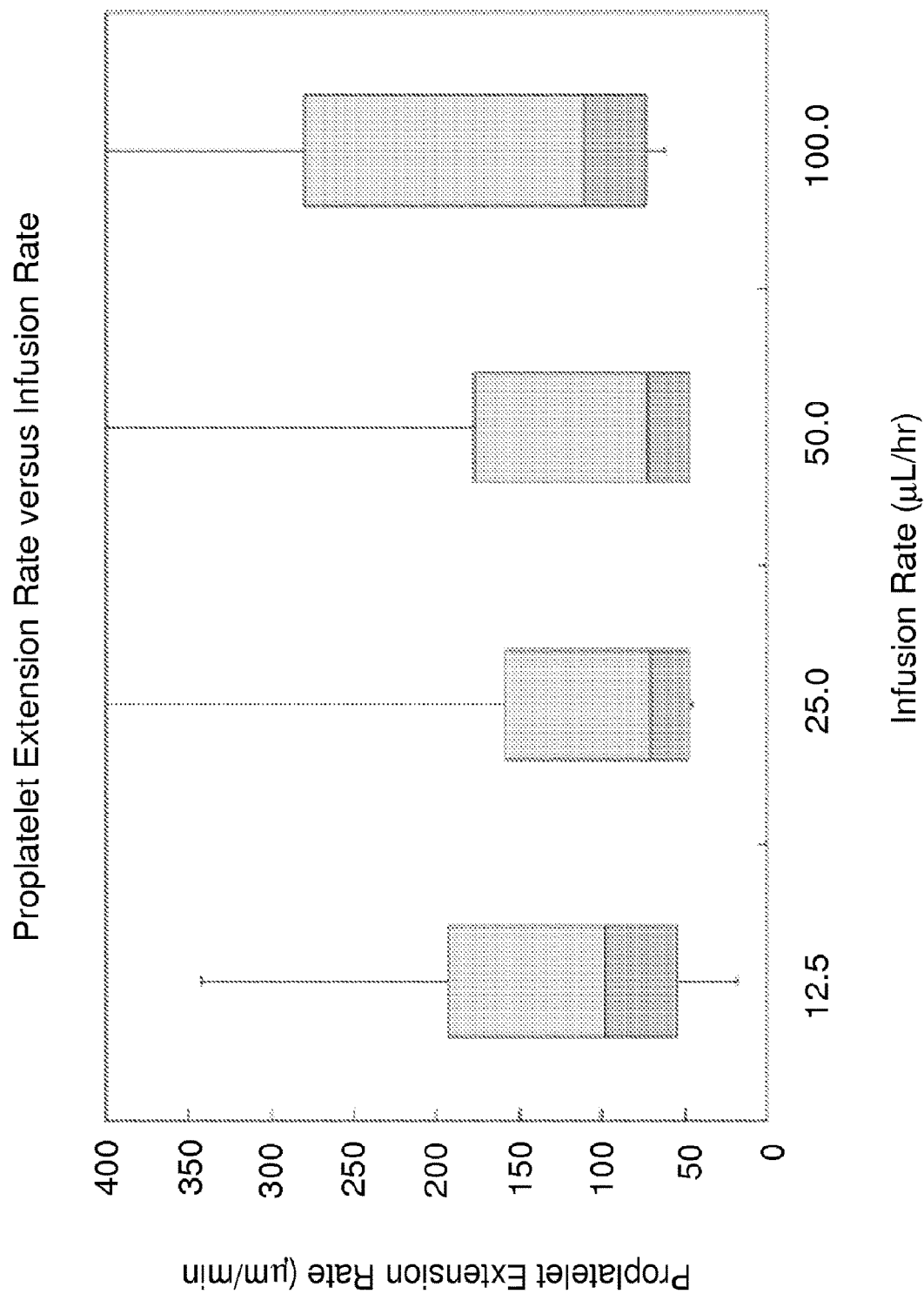
FIG. 4F shows a graph showing that increased shear rates within physiological ranges do not increase proPLT extension rate.
Figure 4G:
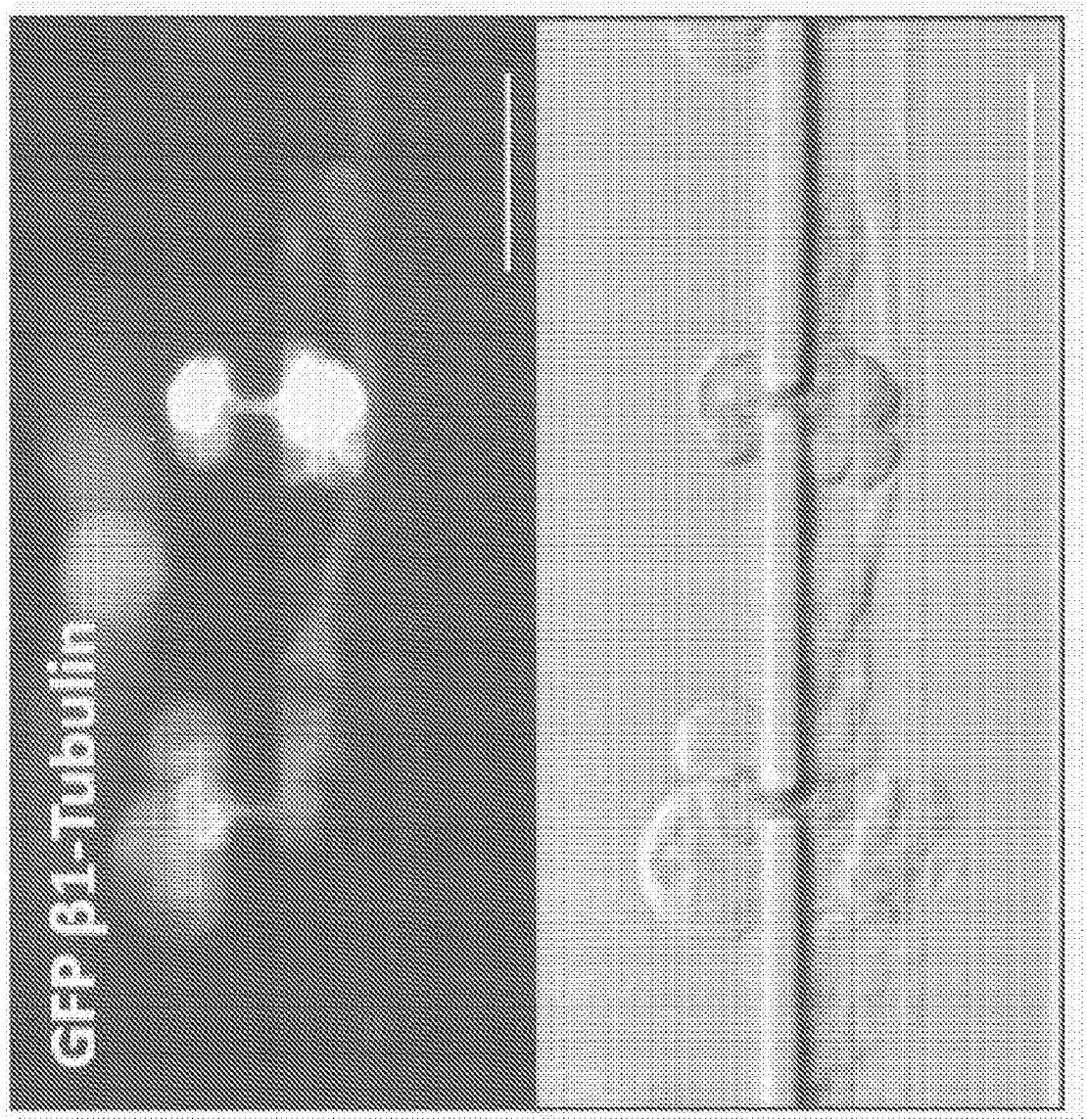
FIG. 4G shows a microscopy image showing that MKs, retrovirally transfected to express GFP-β1 tubulin, showed proPLT extensions and included peripheral microtubules that form coils at the PLT-sized ends.
Figure 4H:
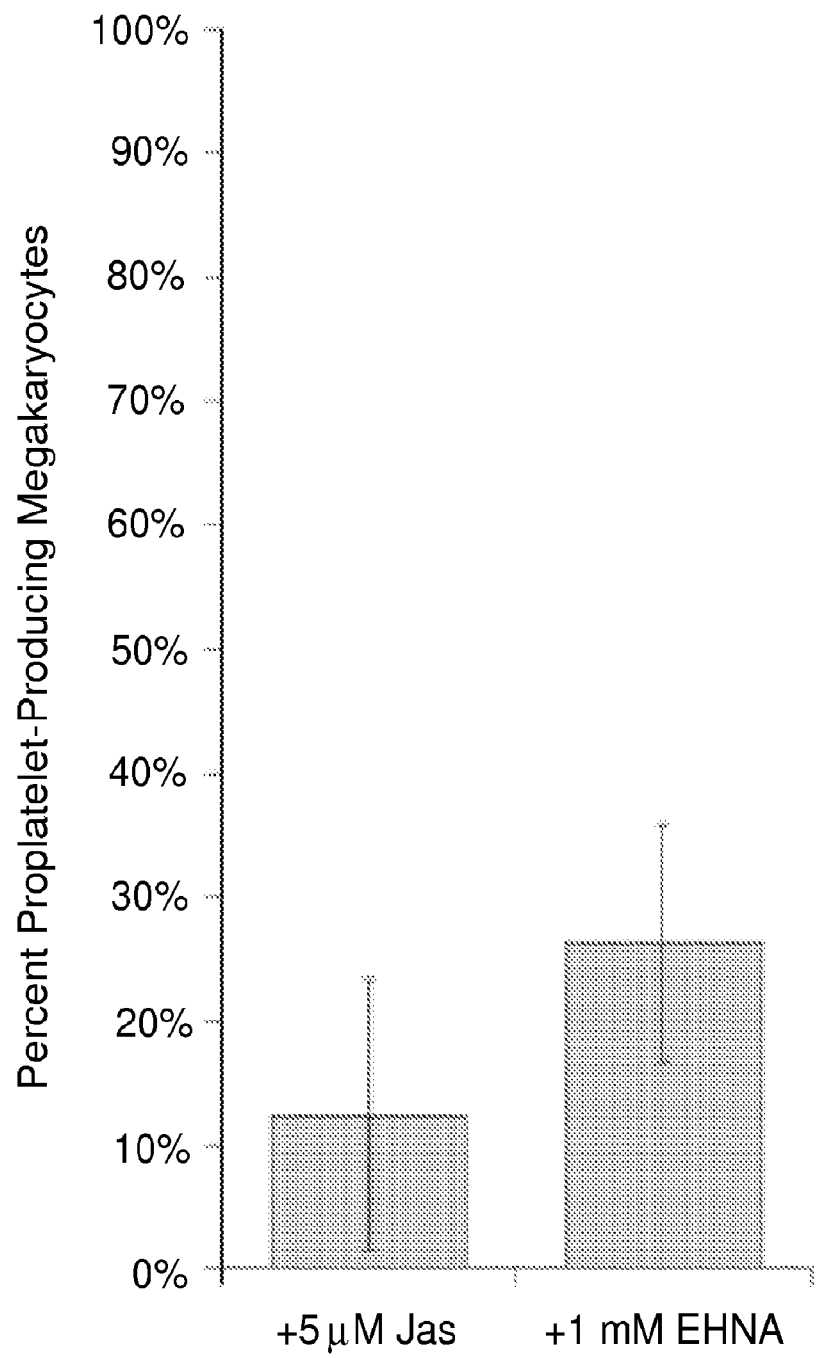
FIG. 4H shows a graph illustrating that 5 µM Jasplankinolide (Jas, actin stabilizer) and 1 mM erythro-9-(3-[2-hydroxynonyl] (EHNA, cytoplasmic dynein inhibitor) inhibit shear-induced proPLT production.
Figure 4I:
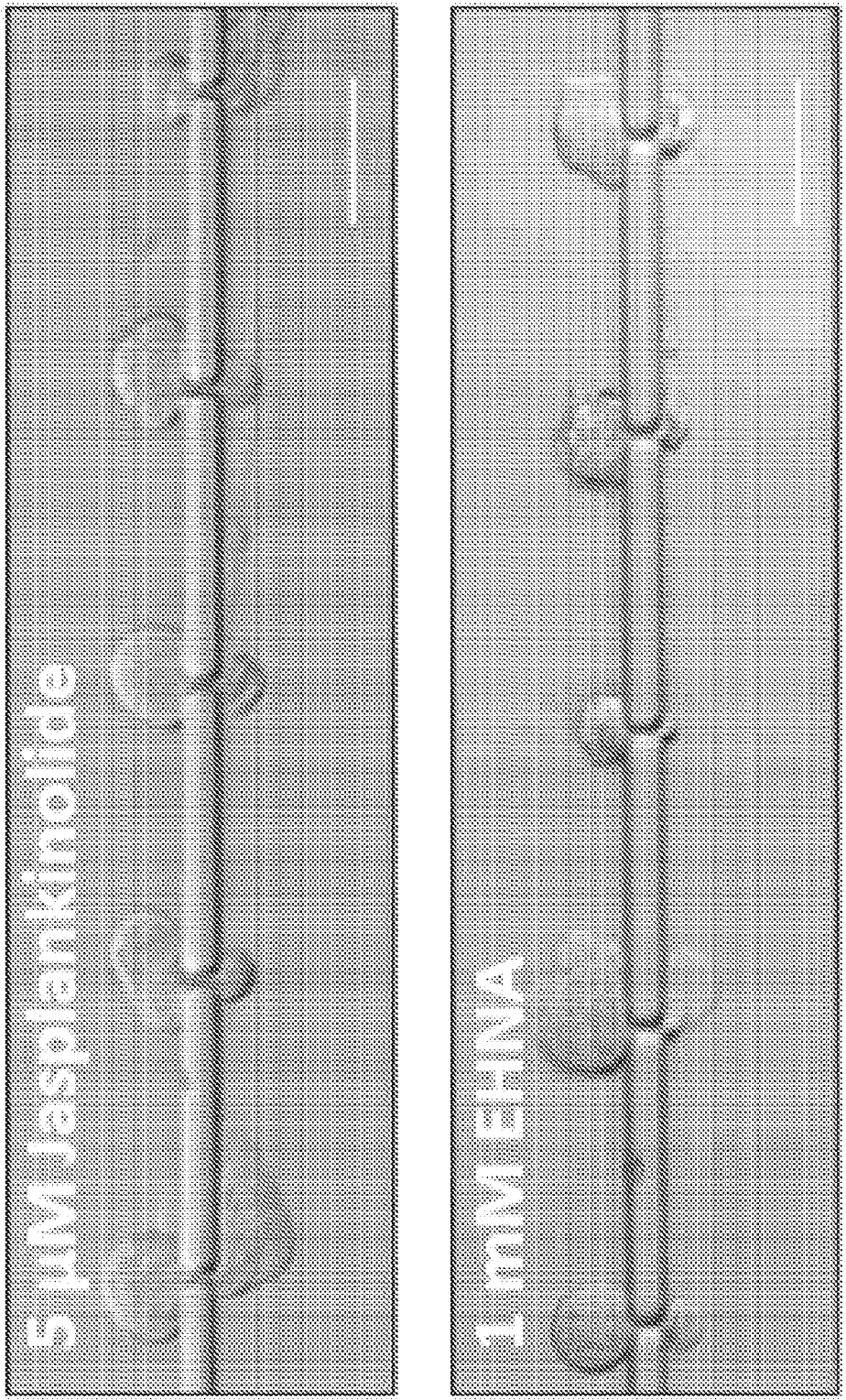
FIG. 4I shows microscopy images that illustrate drug-induced inhibition of proPLT production under physiological shear.

While shear rates were kept constant, proPLT extension rates varied at different positions along the shaft, predictive of a regulated cytoskeletal driven mechanism of proPLT elongation (shown in FIG. 4C). Increasing microfluidic shear rates within the physiological range did not affect the median proPLT extension rate or the distribution of proPLT extension rates in culture (shown in FIG. 4F), and proPLT projections in MKs retrovirally transfected to express GFP-β1 were comprised of peripheral microtubules (MTs) that formed coils at the PLT-sized ends (shown in FIG. 4G). ProPLTs reached lengths exceeding 5 mm, and resisted shear rates up to 1000 $s^{-1}$ in vitro; recapitulating physiological examples of proPLT production from intravital microscopy, and demonstrating that abcission events were not caused by shear. To confirm that shear-induced proPLT extension was cytoskeletal-driven, MKs were incubated with 5 µM Jasplankinolide (Jas, actin stabilizer) or 1 mM erythro-9-(3-[2-hydroxynonyl] (EHNA, cytoplasmic dynein inhibitor) prior to infusion in microfluidic device. Both Jas and EHNA inhibited shear-induced proPLT production (shown in FIG. 4H and FIG. 4I) and PLT release under both static and physiological shear conditions.

Derived PLTs Manifest Structural and Functional Properties of Blood PLTs

Figure 5A:
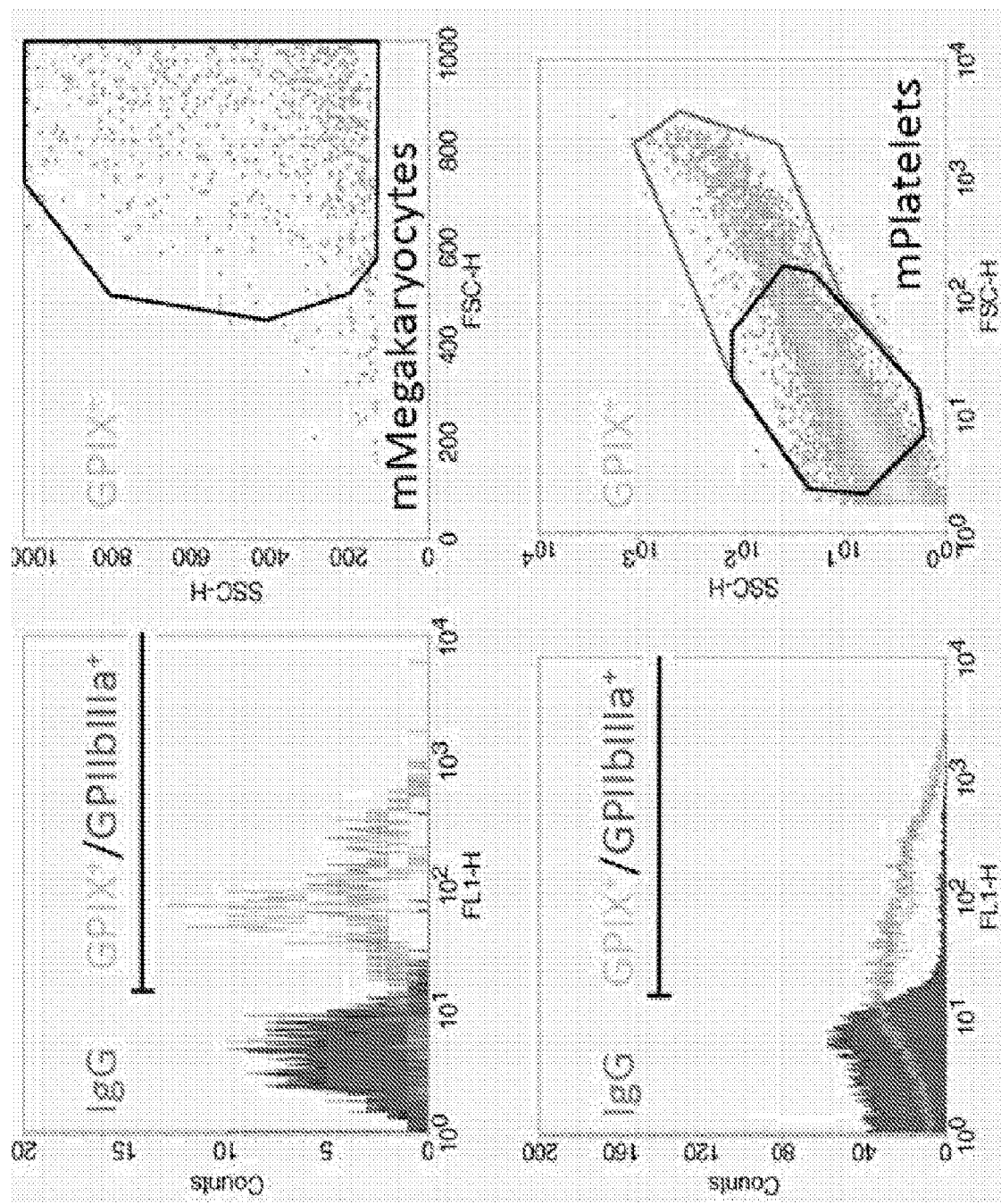
FIG. 5A shows graphs illustrating that PLTs produced in accordance with the present disclosure manifest structural and functional properties of blood PLTs.
Figure 5B:
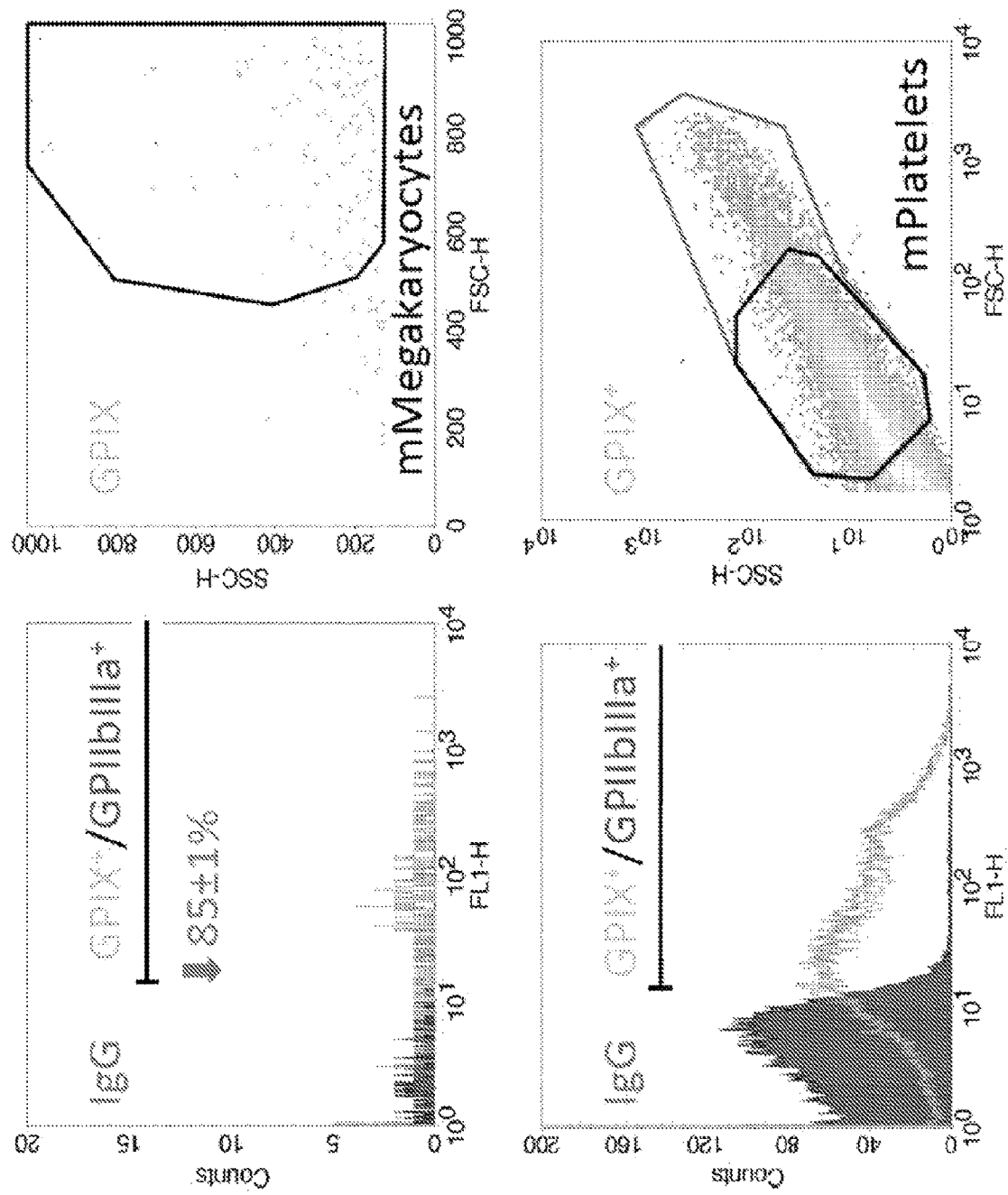
FIG. 5B shows graphs that illustrate biomarker expression, forward/side scatter and relative concentration of GPIX+MKs infused into a system, in accordance with the present disclosure, following isolation from culture on day 4, and collection from effluent 2 hours post infusion.
Figure 5C:
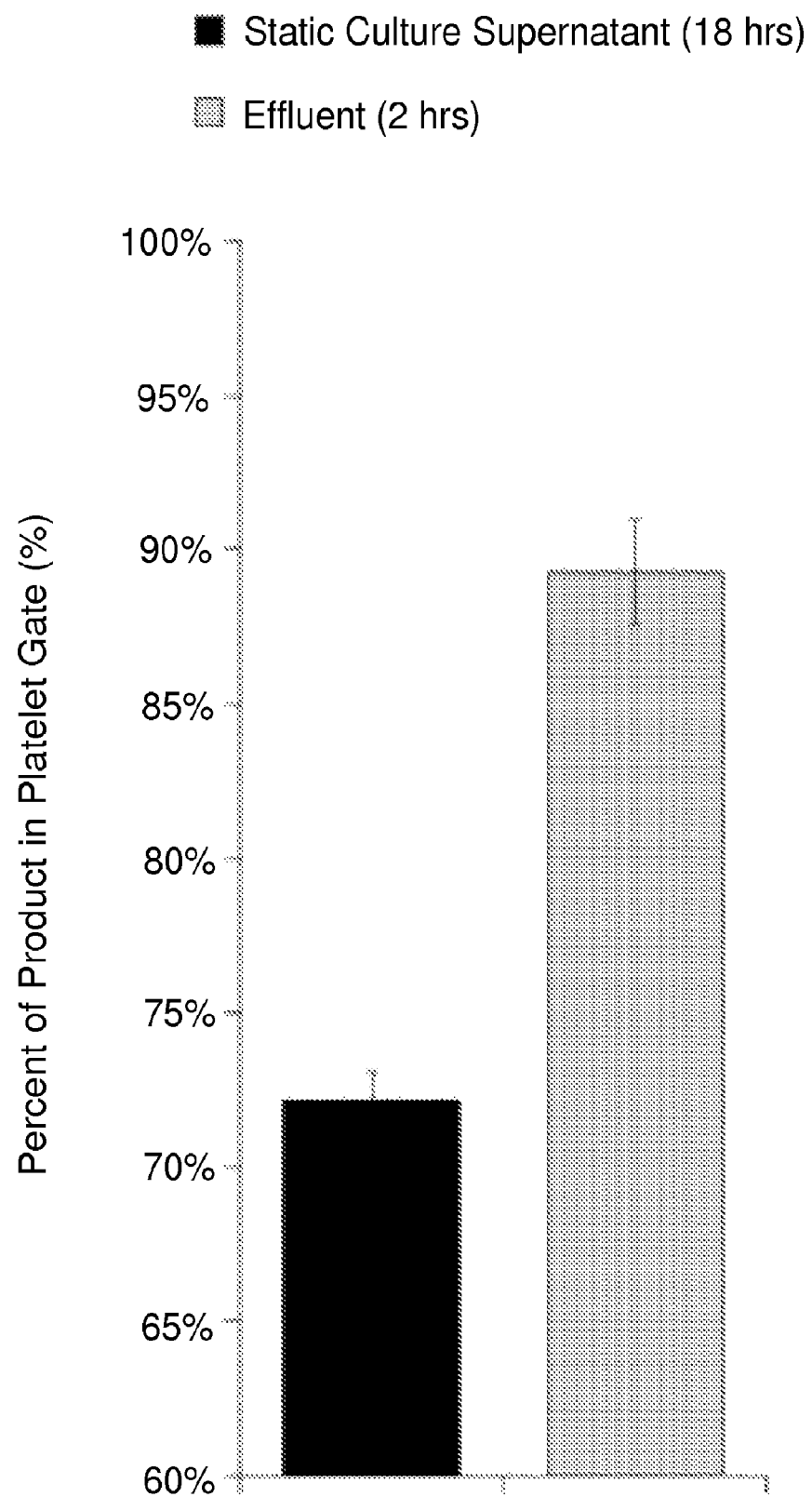
FIG. 5C shows a graph illustrating that the application of shear shifts GPIX+produce more PLT-sized cells relative to static culture supernatant.
Figure 5D:
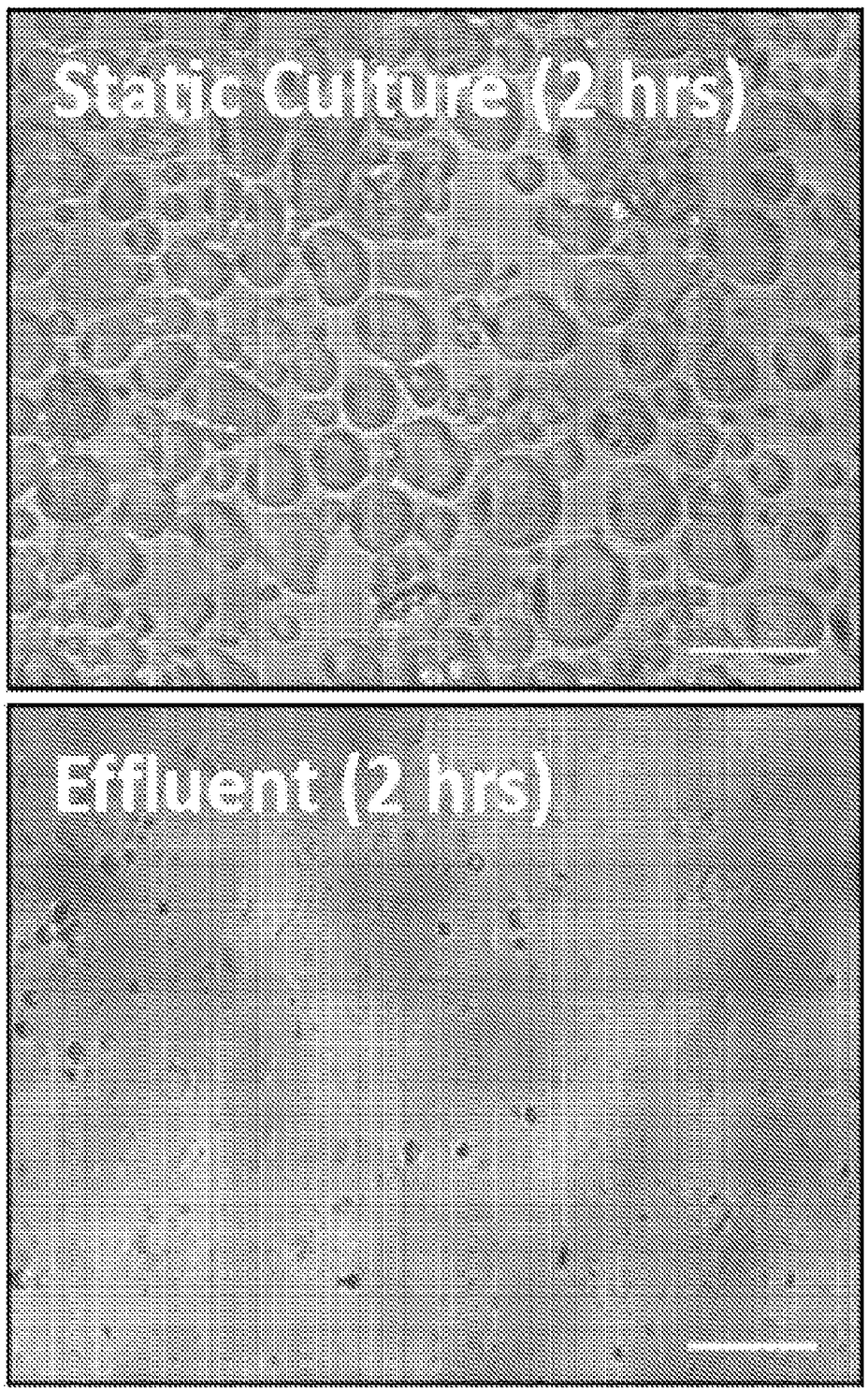
FIG. 5D shows microscopy images illustrating that MKs are converted into PLTs over a period of 2 hours.

PLTs are anucleate discoid cells ~1-3 µm in diameter that express biomarkers GP IX and IIbIIIa on their surface, and are characterized by a cortical MT coil of 6-8 MTs encircling an actin-based cytoskeletal network. To establish PLT yield, biomarker expression, and forward/side scatter and relative concentration of glycoprotein (GP) IX+mFLC-MKs were measured by flow cytometry immediately before infusion in our microfluidic device on culture day 4 (shown in FIG. 5A). Effluent was collected 2 hours post infusion and compared to mFLC-MK input (shown in FIG. 5B). Input MKs and effluent PLTs both expressed GP IX and IIbIIIa on their surface, and displayed characteristic forward/side scatter. The application of shear shifted the cellular composition of the effluent toward more PLT-sized GPIX+ cells relative to static culture supernatant isolated on culture day 5 (shown in FIG. 5C). 85±1% of MKs were converted into PLTs over 2 hours, which agreed with our quantitation of percent proPLT production (FIG. 3D) and constitutes a significant improvement over static cultures (FIG. 5D). Continuous perfusion of roughly 500 $s^{-1}$ shear over 2 hours in our microfluidic device yielded roughly 21 PLTs per MK and constitutes a major advance in PLT production rate over existing culture approaches that generate comparable PLT numbers over a much longer period of time (6-8 days).

Figure 5E:
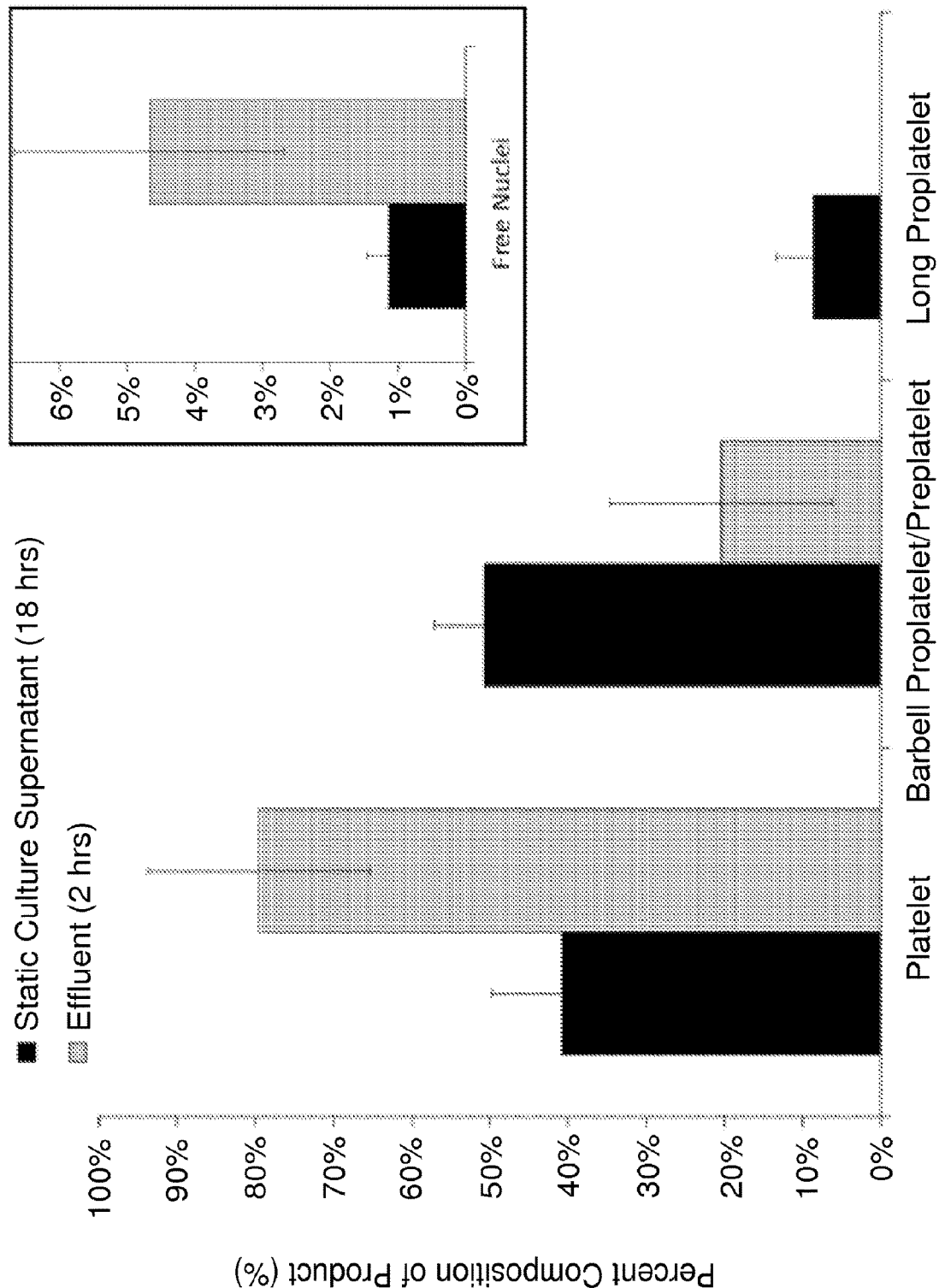
FIG. 5E is a graphical illustration showing that application of shear shifts produce more PLT-sized β1 tubulin+ Hoescht-cells relative to static culture supernatant, with the insert shows quantitation of free nuclei in the effluent.

To quantify the morphological composition of our product, the effluent from our microfluidic device was probed for β1 tubulin (PLT-specific tubulin isoform) and Hoescht (nuclear dye), and analyzed by immunofluorescence microscopy. Cells were binned according to their morphology and size, and compared to static MK culture supernatants. The application of shear shifted the cellular composition of the effluent toward more PLT-sized β1 tubulin+Hoescht-cells (shown in FIG. 5E), which agreed with flow cytometry data (FIG. 5C) and resulted in a product that was more similar in composition to the distribution of PLT intermediates in whole blood. Quantitation of free nuclei in effluent confirmed increased microfluidic device-mediated PLT production relative to static cultures and established PLT yields of roughly 20±12 PLTs per MK, which agree with flow cytometry data.

Figure 5F:
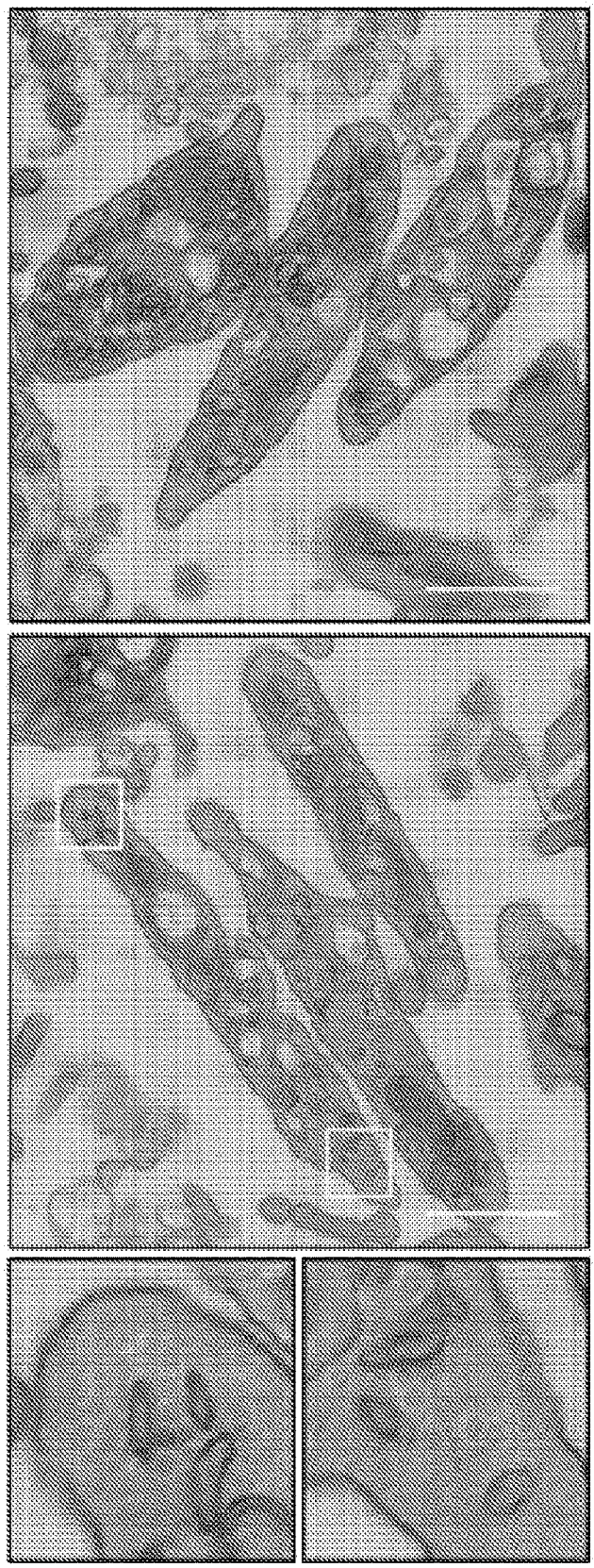
FIG. 5F shows microscopy images illustrating that PLTs, produced in accordance with the present disclosure, are ultrastructurally similar to blood PLTs and contain a cortical MT coil, open canalicular system, dense tubular system, mitochondria, and characteristic secretory granules.
Figure 5G:
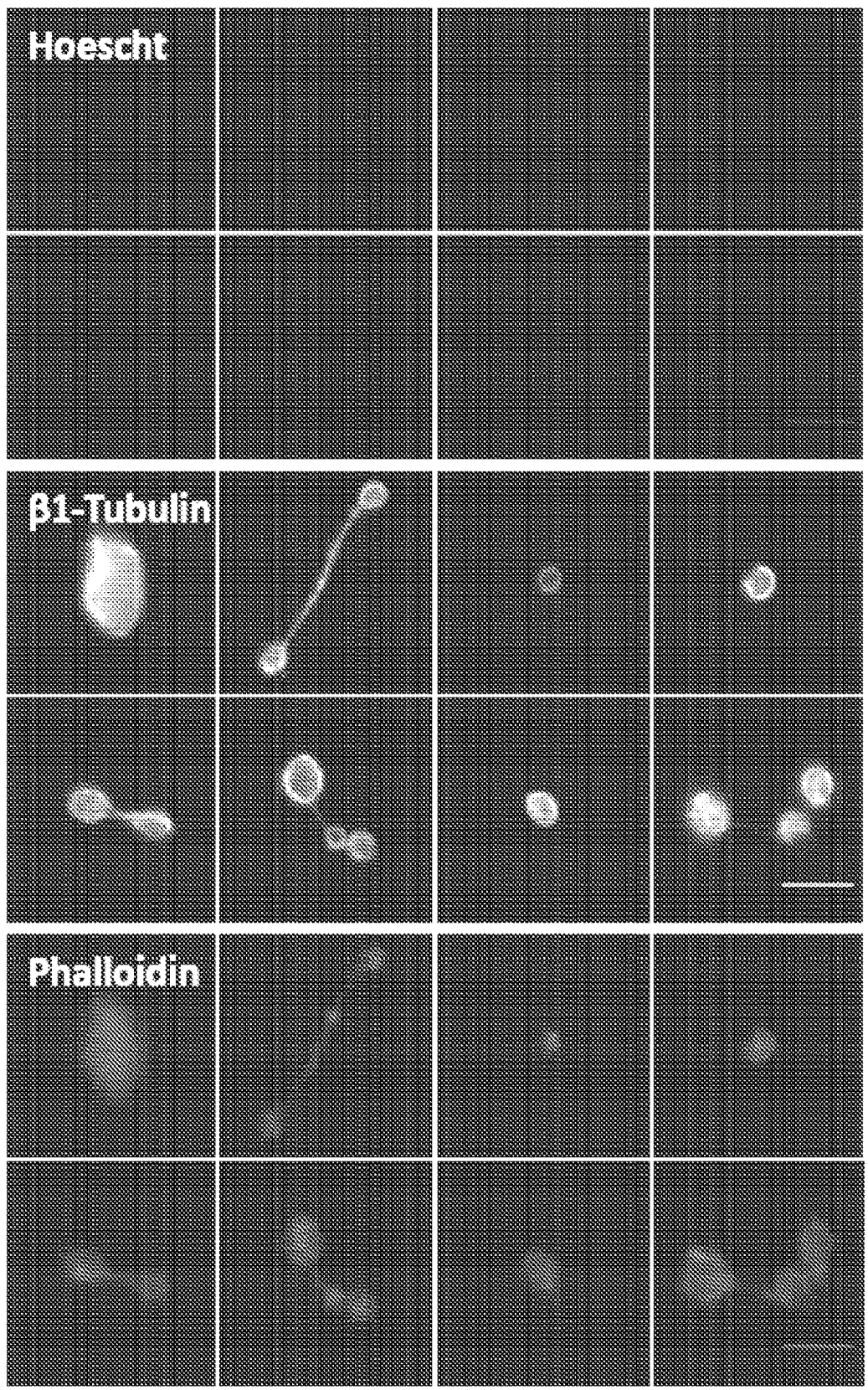
FIG. 5G shows microscopy images that illustrate PLTs and PLT intermediates, produced in accordance with the present disclosure, are morphologically similar to blood PLTs and display comparable MT and actin expression.

Resting PLTs contain characteristic invaginations of the surface membrane that form the open canalicular system, a closed channel network of residual endoplasmic reticulum that form the dense tubular system, organelles, specialized secretory granules, and will flatten/spread on contact activation with glass. Microfluidic device-generated PLTs were ultrastructurally indistinguishable from mouse blood PLTs by thin-section transmission electron; and contained a cortical MT coil, open canalicular system, dense tubular system, mitochondria, alpha- and dense-granules (as shown in FIG. 5F). Microfluidic device-generated PLTs and PLT intermediates displayed comparable MT and actin organization to mouse blood PLTs by immunofluorescence microscopy (as shown in FIG. 5G), and spread normally on contact-activation with glass, forming both filpodia and lamellipodia.

Application of the Microfluidic Device to Human PLT Production

Figure 6A:
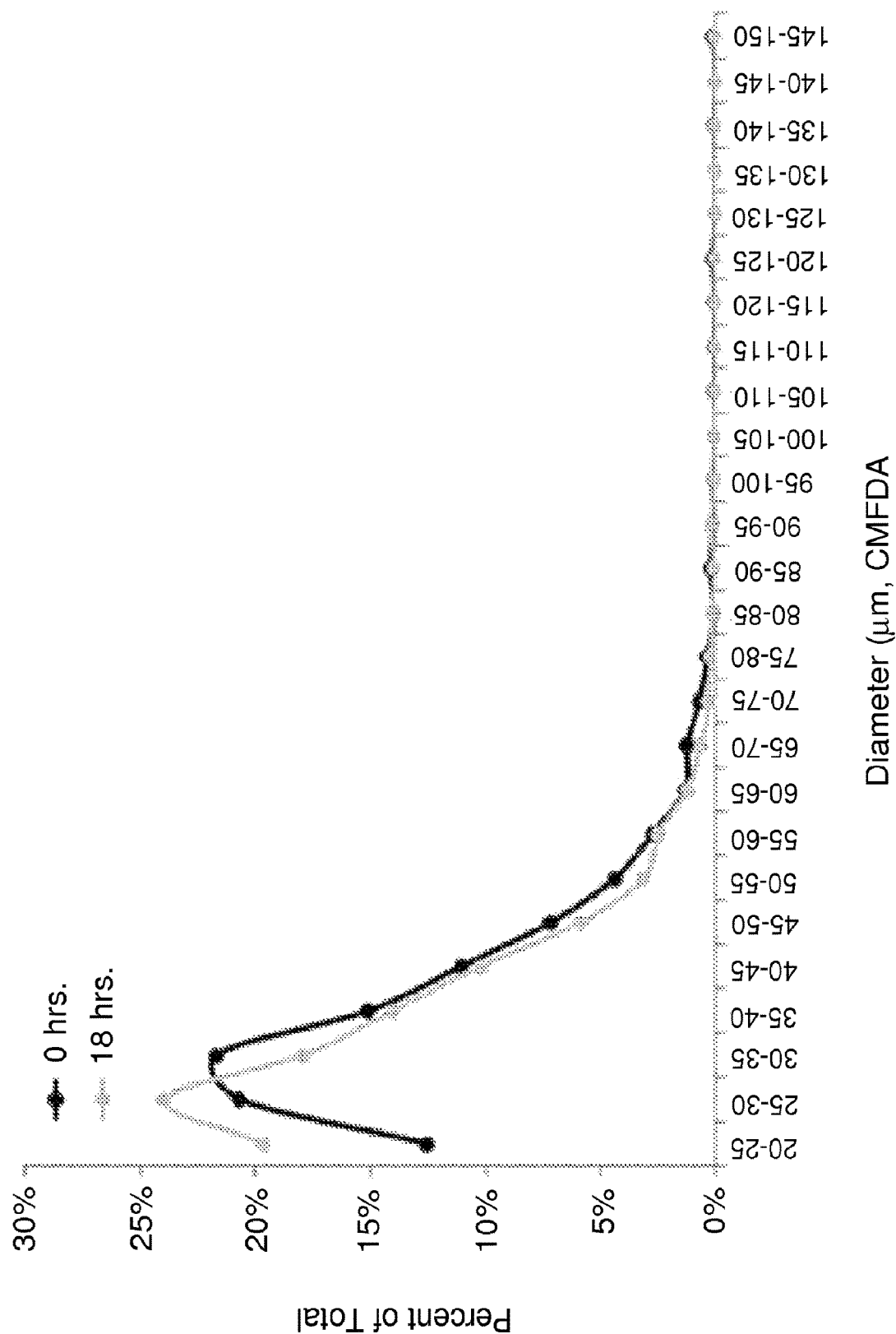
FIG. 6A shows a graph illustrating that hiPSC-PLTs, derived in accordance with the present disclosure, manifest structural and functional properties of blood PLTs.
Figure 6B:
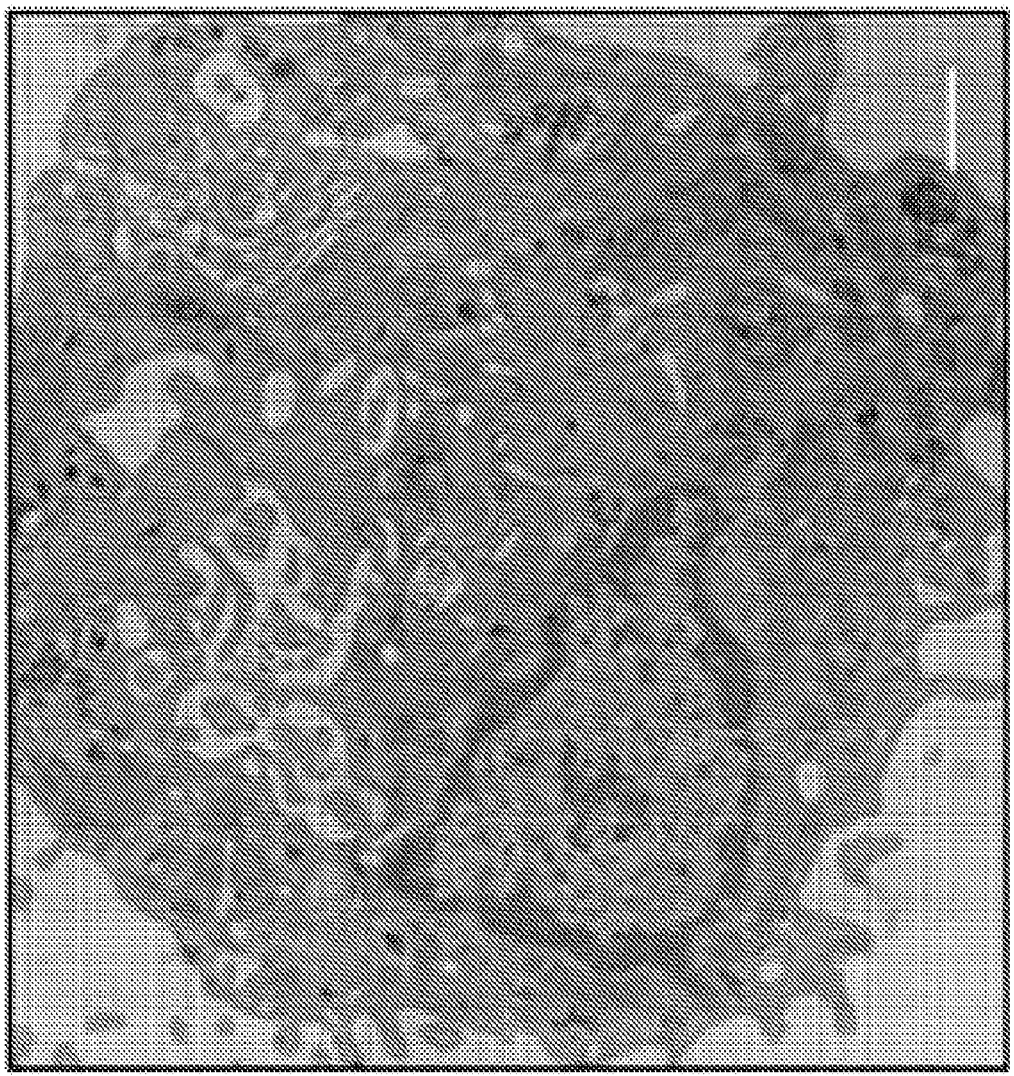
FIG. 6B shows a microscopy image illustrating that hiPSC-MKs, in accordance with the present disclosure, are ultrastructurally similar to primary human MKs and contain a lobulated nuclei, invaginated membrane system, glycogen stores, organelles, and characteristic secretory granules.
Figure 6C:
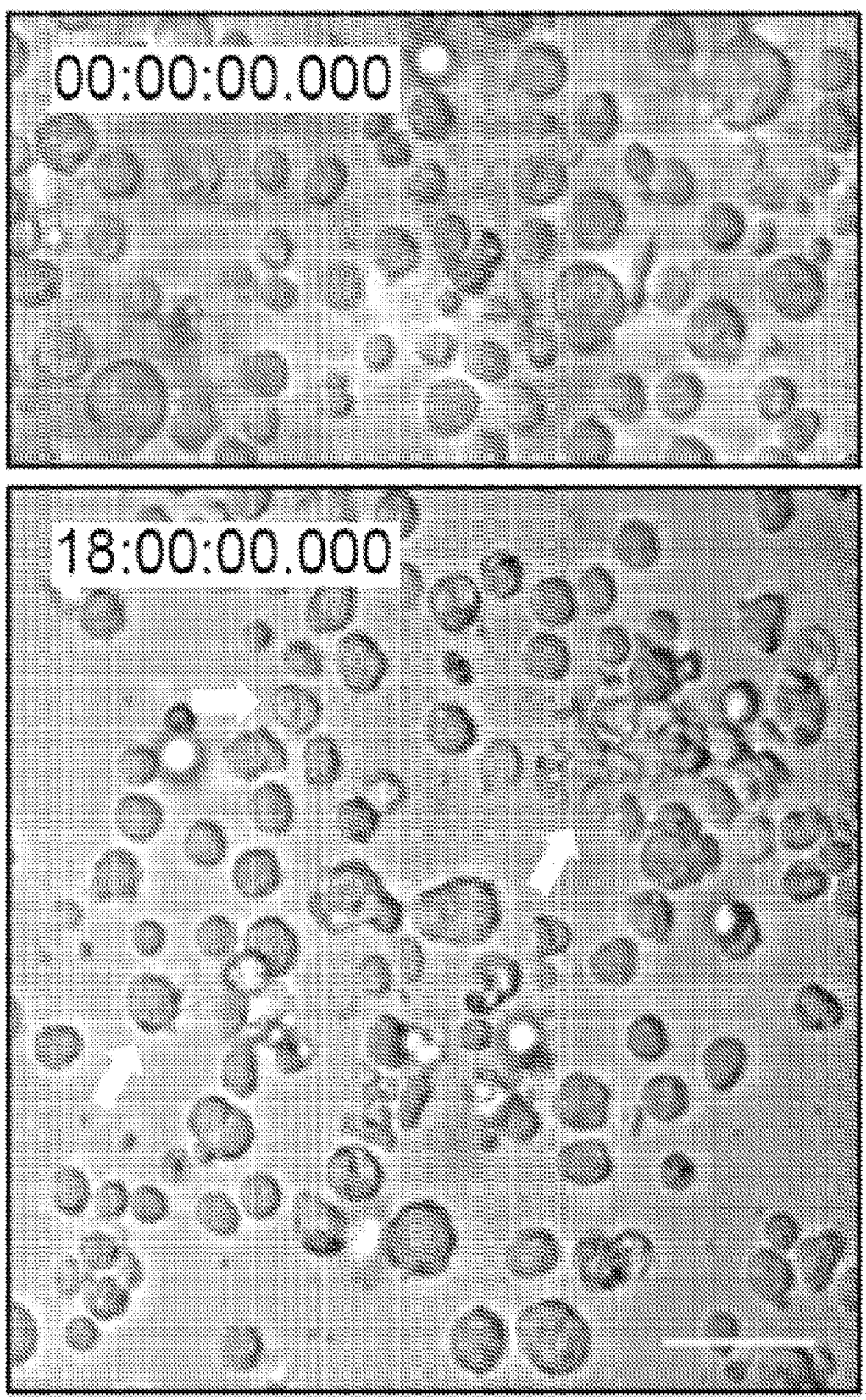
FIG. 6C shows microscopy images illustrating that hiPSC-MKs in static culture begin producing proPLTs at 6 hours post-purification, and reach maximal proPLT production at 18 hours.
Figure 6D:
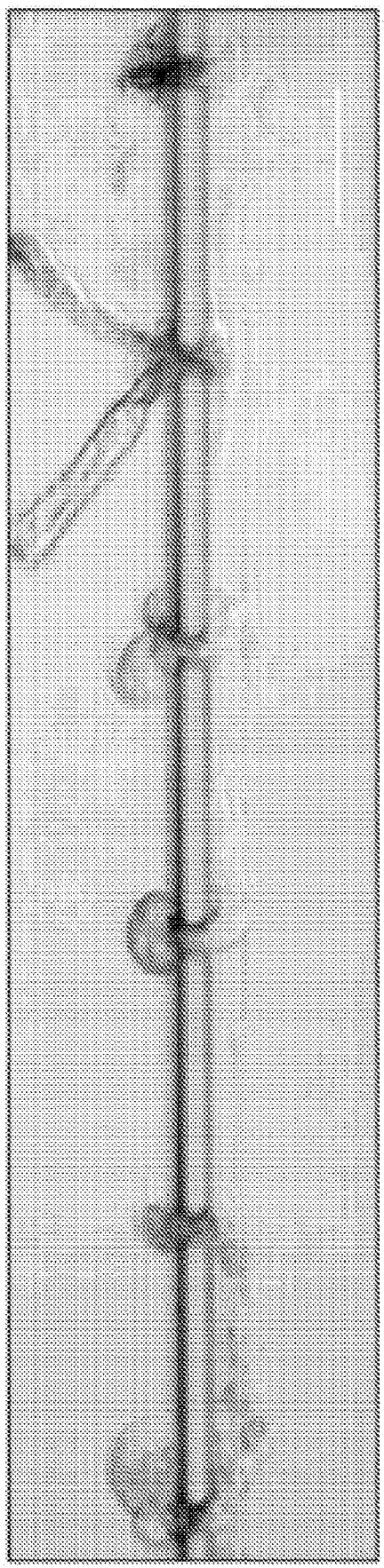
FIG. 6D shows a microscopy image illustrating that hiPSC-MKs under physiological shear (about 500 s$^{-1}$) begin producing proPLTs immediately upon trapping and extend/release proPLTs within the first 2 hours of culture.

To generate human PLTs, mFLC-MK in our microfluidic device were replaced with hiPSC-derived MK, which provide a virtually unlimited source of MKs for infusion. hiPSC-MKs were isolated on culture day 15, once they had reached maximal diameter of 20-60 µm (shown in FIG. 6A), and were ultrastructurally similar to primary human MKs (shown in FIG. 6B). In static culture, hiPSC-MKs began producing proPLTs at 6 hours post-isolation, and reached maximal proPLT production at 18 hours (shown in FIG. 6C). By comparison, hiPSC-MKs under physiological shear (about 500 $s^{-1}$) began producing proPLTs immediately upon trapping, and extended/released proPLTs within the first 2 hours of culture (shown in FIG. 6D). The percent proPLT-producing hiPSC-MKs under shear were increased significantly over static cultures (~10%) to roughly 90% (as shown in FIG. 6E).

Figure 6G:
FIG. 6G shows microscopy images illustrating that hPLTs, derived in accordance with the present disclosure, are ultrastructurally similar to human blood PLTs and contain a cortical MT coil, open canalicular system, dense tubular system, mitochondria, and characteristic secretory granules.
Figure 6H:
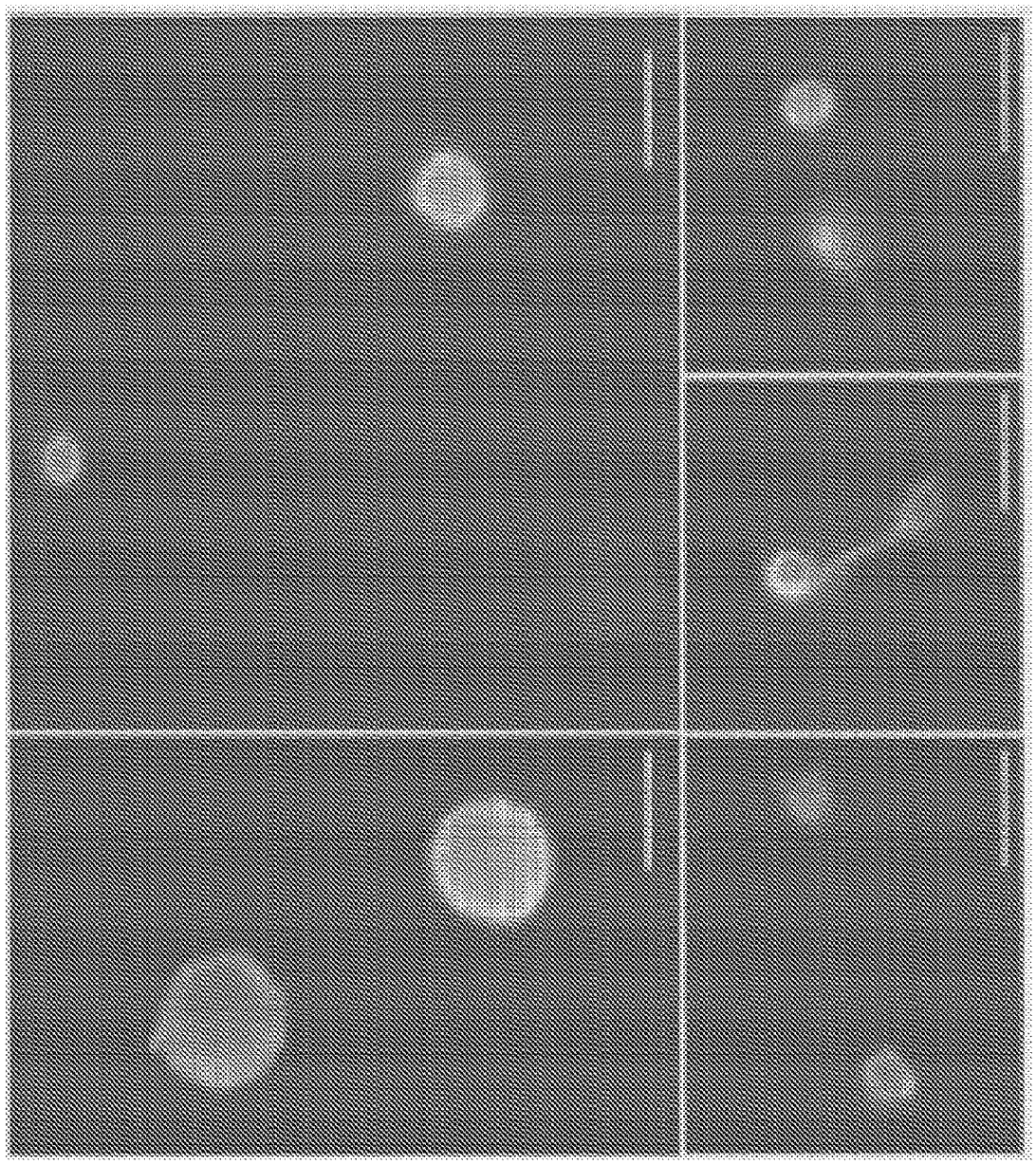
FIG. 6H shows microscopy images illustrating that hPLTs, derived in accordance with the present disclosure, are morphologically similar to human blood PLTs and display comparable MT and actin expression.
Figure 6I:
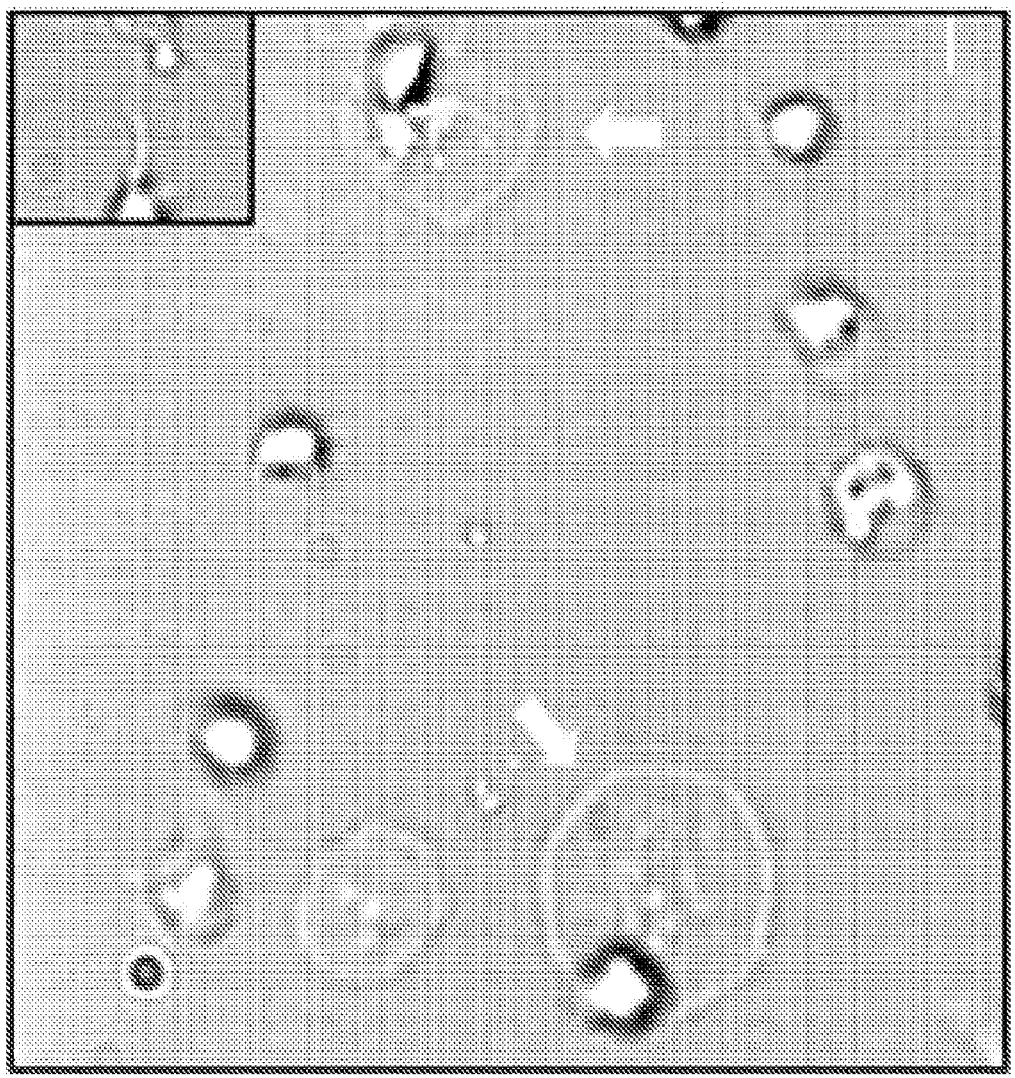
FIG. 6I shows microscopy images illustrating that mPLTs, derived in accordance with the present disclosure, form filpodia/lamellipodia on activation and spread on glass surface.

ProPLT extension rates were slightly lower than mFLC-MK controls (~19 µm/min versus 30 µm/min) (shown in FIG. 6F) and more closely approximated physiological controls. Microfluidic device-generated PLTs displayed forward and side scatter, and surface biomarker expression characteristic of human blood PLTs, were ultrastructurally indistinguishable from human blood PLTs by thin-section transmission electron (shown in FIG. 6G), displaying comparable MT and actin expression to human blood PLTs by immunofluorescence microscopy (shown in FIG. 6H), spreading normally on contact-activation with glass, and forming both filpodia and lamellipodia (shown in FIG. 6I). Taken together these data demonstrate that hiPSC-MKs can be applied to our biomimetic microfluidic device to generate potentially unlimited numbers of functional human PLTs.

Application of the Microfluidic Device to Drug Development

Thrombocytopenia may appear suddenly and often unintentionally, potentially causing major bleeding and death. Antibody and cell-mediated autoimmune responses have been shown to cause thrombocytopenia. In addition, thrombocytopenia may also be triggered by a wide range of medications, including cancer drugs, such as dasatinib. Animal models are generally poor predictors of safety and efficacy of medications in humans, and clinical studies are time-consuming, expensive, and potentially harmful. Microfluidic devices designed to mimic human BM represent an area of innovation of major clinical importance, offering an efficient and realistic platform to investigate the effects of a variety of medications upon BM and MK biology.

PLT survival and clearance rates are usually measured through infusion studies using flow cytometry. Quantification of the rate and extent of proPLT production, however, is not amenable to this approach, and requires direct visualization to establish at what stage thrombocytopoiesis is affected. By contrast, the application of microfluidic systems, in accordance with the present disclosure, offers a great platform to study drug effects on PLT production, one that may facilitate the identification of new regulators of PLT production and elucidate the mechanism of clinically significant drug-induced thrombocytopenias.

Figure 7:
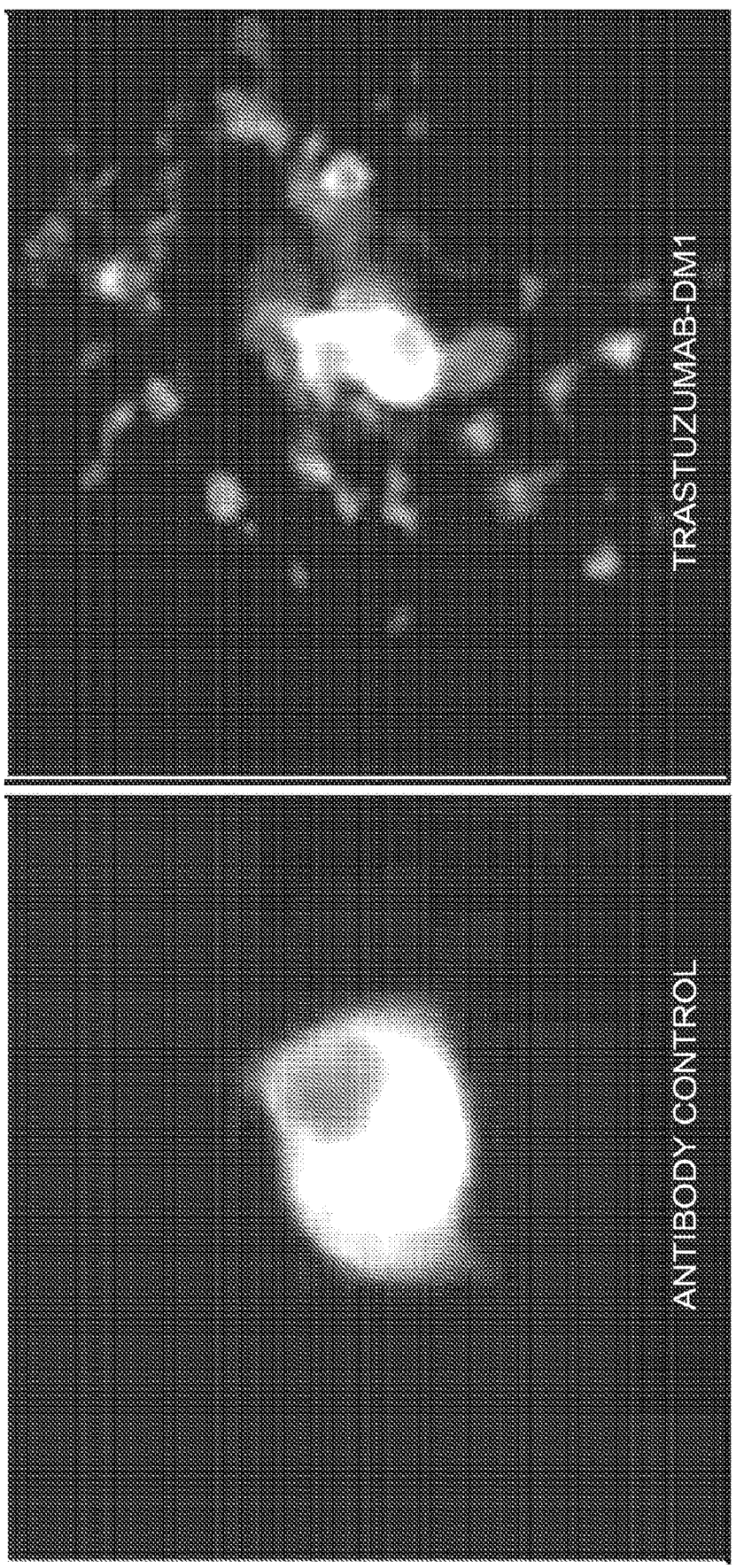
FIG. 7 shows live-cell microscopy images illustrating that T-DM1 inhibits MK differentiation and disrupts proPLT formation by inducing abnormal tubulin organization.

As proof of concept, high-content live-cell microscopy was employed to identify the express GFP•PI tubulin (live-cell microscopy) mechanism by which trastuzumab emtansine (T-DM1), an antibodydrug conjugate currently in clinical development for breast cancer, affects PL T production. These studies revealed that T-DM1 inhibits MK differentiation, and disrupts proPLT formation by inducing abnormal tubulin organization (as shown in FIG. 7). Defining the pathways by which therapeutics such as T-DM1 affect MK maturation and proPLT production may yield strategies to manage drug-induced thrombocytopenias and regulate PLT production in vivo.

The approach of the present disclosure capitalizes on a highly novel microfluidic design to recapitulate human BM and blood vessel physiology ex vivo, and generate an alternative source of functional human PLTs for infusion. While clinically desirable to meet growing transfusion needs and obviate risks currently associated with platelet procurement and storage, 2 major quantitative roadblocks have thus far persisted in the development of donor-independent PLTs for therapeutic use: (1) generating sufficient numbers (~3× $10^8$) of human MKs to support the production of one PLT transfusion unit (~3×$10^{11}$ PLTs), and (2) generating physiological numbers of functional human PLTs (~$10^3$-$10^4$) per MK. The development of human embryonic stem cell cultures (hESC), and more recently, human induced pluripotent stem cell cultures (hiPSC), offer a potentially unlimited source of progenitor cells that can be differentiated into human MKs in vitro to address the first quantitative roadblock. Indeed, because PLTs are anucleate, PLT microfluidic device-derived units could be irradiated prior to infusion, addressing concerns that cellular products derived from hESC or hiPSCs could be oncogenic or teratogenic.

Attempts to study the environmental drivers of PLT production have been constrained by reductionist approaches, and a major limitation of 2D liquid cultures has been their inability to account for 3D BM composition and stiffness, directionality of proPLT extension, and proximity to venous endothelium. Likewise, while proPLT-producing MKs entering sinusoidal blood vessels experience wall shear rates of 500 to 2500 $s^{-1}$, attempts to model vascular flow by perfusing MKs over ECM-coated glass slides have selected for immobilized/adhered MKs, and have been unable to discriminate ECM-contact activation from shear. Alternatively, released proPLTs have been centripetally agitated in an incubator shaker, which does not recapitulate laminar shear flow in BM blood vessels, does not provide precise control of vascular shear rates, and is not amenable to high-resolution live-cell microscopy. Nonetheless, despite these limitations, exposure of MKs to high shear rates (1800 $s^{-1}$) accelerated proPLT production, and proPLTs cultured in the absence of shear released significantly fewer PLTs than those maintained at fluid shear stresses of ~0.5 Pa for 2 hours. Moreover, recent advances in multiphoton intravital microscopy have provided increasing resolution of proPLT production in vivo and confirmed the importance of vascular flow on proPLT extension and PLT release. While these studies have provided physiologically accurate examples of in vivo proPLT production, poor resolution and limited control of the microenvironment has prohibited detailed study of how the BM microenvironment contributes to PLT release.

Mounting evidence that cell-cell contacts, extracellular matrix (ECM) composition and stiffness, vascular shear rates, pO2/pH, soluble factor interactions, and temperature contribute to proPLT formation and PLT release have suggested that recapitulating BM and blood vessel microenvironments within a 3D microfluidic culture system is necessary to achieve clinically significant numbers of functional human PLTs. Indeed, modular 3D knitted polyester scaffolds have been applied under continuous fluid flow to produce up to 6×$10^6$ PLTs/day from 1×$10^6$ CD34+ human cord blood cells in culture. While suggestive that clinically useful numbers of culture-derived human PLTs are attainable, 3D perfusion bioreactors have not accurately reproduced the complex structure and fluid characteristics of the BM microenvironment, and their closed modular design has prevented direct visualization of proPLT production, offering little insight into the mechanism of PLT release. Alternatively, 3D PDMS biochips adjacent ECM-coated silk-based tubes have been proposed to reproduce BM sinusoids and study MK differentiation and PLT production in vitro. While capable of recapitulating MK migration during maturation, this design is not amenable to high resolution live-cell microscopy, and does not reproduce endothelial cell contacts necessary to drive MK differentiation.

By comparison, the microfluidic device design of the present disclosure offers the complete package, allowing significant improvement in time to PLT release and an increased total PLT yield. Also, application of vascular shear rates within the microfluidic device induces proPLT production, and reproduces physiological proPLT extension and release. Furthermore, MKs are capable of squeezing through small gaps to enter the circulation and releasing prePLT intermediates under physiological flow conditions. The product resulting from continuous perfusion of MKs in the microfluidic device of the present disclosure approached physiological PLT concentrations, and manifested both structural and functional properties of blood PLTs. Finally, PLT microfluidic devices could be applied to human MK cultures to produce functional human PLTs. Although PLT yield per MK fell short of theoretical estimates, the observation that MK cultures routinely released large MK fragments (prePLTs, proPLTs) as well as MK themselves into the effluent channel, suggests that actual PLT numbers may depend on the further differentiation of PLT intermediates into PLTs in supportive microenvironments such as the lung or circulating blood. Indeed, when mFLC-derived proPLTs were infused into mice, these were rapidly converted into PLTs over a period of 12-24 hours. Interestingly, while CMFDA-labeled PLTs in this study were readily detected in the blood, larger prePLT intermediates were not, suggesting that they may be trapping in a microcirculation of the lung. Likewise, when mFLC and BM-derived MKs were infused into mice they almost exclusively localized to the lungs and released PLTs within the first two hours. In both cases, it is almost certain that vascular shear rates, soluble factor interactions in the blood, and endothelial cell contacts regulate this process, and examining how local microenvironments in these tissues contribute to terminal PLT production warrant further investigation.

By combining the major elements of BM physiology including 3D ECM composition and stiffness, cell-cell contacts, vascular shear rates, pO2/pH, soluble factor interactions, and temperature within a single microfluidic system, the approach of the present disclosure offers unprecedented control of ex vivo microenvironments and a biomimetic platform for drug development. Moreover, support of high-resolution live-cell microscopy permits direct visualization of cells during culture and provides a window into poorly characterized physiological processes. Lastly, the microfluidic device design can be easily scaled by mirroring effluent channels on either side of a central channel, elongating the device to support greater numbers of columns, and positioning multiple units in parallel within a larger microfluidic device matrix. Continuous harvesting of hiPSC-MKs in longer devices may result in clinically significant numbers of PLTs to perform, for example, traditional aggregometry tests of PLT function, and in vivo xeno-transfusion studies in immune-suppressed mice to measure increases in PLT counts, which require roughly $10^8$ PLTs per study.

In summary, the present disclosure has demonstrated systems and methods for reproducing human BM and sinusoidal blood vessel microenvironments for generating human platelets in an approach amenable to high resolution imaging. Biomimetic microfluidic systems, in accordance with the present disclosure, may be fabricated using PDMS, glass and any other suitable materials, and include several microfluidic channel and chamber configurations designed to simulate realistic physiological conditions, such as flow velocities, shear rates, pressure differentials, and so forth. As such, the channels or chambers of microfluidic systems described herein may be selectively coated with ECM and human endothelial cells, as well as other biological agents or materials consistent with physiological systems. In some forms of operation, as described, round or proPLT-producing MKs, infused along different channels of the microfluidic systems detailed herein, may sequentially become trapped, and extend platelet-producing proPLTs into adjacent channels that subsequently release PLTs for harvest. Such processes may be stimulated or optimized by controllable physiological shear rates and regulated microenvironments, and the released PLTs entering the fluid stream can be collected from the effluent, with the process being capable of visualization using, for example, high-resolution microscopy.

The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:
1. A biomimetic microfluidic system comprising:
a substrate;
a first channel formed in the substrate, the first channel extending from a first input to a first output along a longitudinal direction and extending along a first transverse direction;
a second channel formed in the substrate, the second channel extending from a second input to a second output along the longitudinal direction and extending along the first transverse direction, wherein the first and second channels extend substantially parallel for a longitudinal dimension and are separated by columns extending along a second transverse direction;
a series of apertures formed in between the columns to create a fluid communication path passing between the channels, wherein each of the series of apertures is positioned proximal to a first portion of the substrate, extends along the longitudinal direction further than along the first transverse direction and the second transverse direction, and is configured to selectively capture a biological source material from a fluid passing therethrough;
a first source connected to the first input, the first source being configured to selectively introduce into the first channel at least one first biological composition comprising the biological source material at a first channel flow rate; and a second source connected to the second input, the second source being configured to selectively introduce into the second channel at least one second biological composition at a second channel flow rate, wherein the first source and the second source are configured to control the first channel flow rate and the second channel flow rate, respectively, to create a differential between the channels to generate physiological shear rates in the second channel that are sufficient to induce the captured biological source material to produce a target biological substance, and wherein the system further includes a first flow filter positioned upstream from the first input, and a second flow filter positioned upstream from the second input, wherein upstream is defined relative to a direction of flow for the at least one first biological composition and the at least one second biological composition.

2. The system of claim 1 further comprising a third channel formed in the substrate, wherein the third channel extends from the second input to a third output along the longitudinal direction and extends along the first transverse direction, wherein the first and third channels extend substantially parallel along the longitudinal direction and are separated by columns extending along a second transverse direction.

3. The system of claim 2, wherein the system further comprises an another series of apertures formed in the columns separating the first channel and third channel, wherein each of the another series of apertures is positioned proximal to the first portion of the substrate, extends along the longitudinal direction further than in the first transverse direction and the second transverse direction, and creates a fluid communication path passing between the first channel and third channel.

4. The system of claim 2, wherein the second source is further configured to selectively introduce into the third channel at least one third biological composition at a third channel flow rate, wherein the first channel flow rate and the third channel flow rate create an another differential configured to generate the physiological shear rates.

5. The system of claim 3, wherein the series of apertures and the another series of apertures form microchannels extending between the first channel, the second channel, and the third channel.

6. The system of claim 3, wherein the series of apertures and the another series of apertures are formed by at least one of a film, a membrane, and a mesh.

7. The system of claim 3, wherein at least one of the apertures and the another series of apertures have dimensions between 0.1 micrometers and 20 micrometers.

8. The system of claim 3, wherein at least one of the series of apertures and the another series of apertures are sized smaller than a size of the biological source material to capture the biological source material within the apertures or the another apertures.

9. The system of claim 8, wherein the biological source material includes megakaryocytes.

10. The system of claim 4, wherein at least one of the first, second, and third biological compositions includes at least one of a semi-solid, a solid, a liquid, and a collection of cells, or a combination thereof.

11. The system of claim 1, wherein the physiological shear rates are selected from a predetermined range configured to facilitate a production of platelets in the second channel.

12. The system of claim 11, wherein the predetermined range is between $100 \text{ s}^{-1}$ and $10,000 \text{ s}^{-1}$.

13. The system of claim 1, further comprising a first flow resistor positioned between the first input and the first flow filter, and a second flow resistor positioned between the second input and the second flow filter.

14. The system of claim 13, further comprising a second channel port positioned downstream from the second flow resistor along the second channel, and a third channel port positioned downstream from the second flow resistor along the third channel, wherein downstream is defined relative to a direction of flow for the at least one first biological composition and the at least one second biological composition.

15. The system of claim 1, wherein the longitudinal dimension is between 1000 micrometers and 30,000 micrometers.

16. The system of claim 3, wherein a transverse dimension of the first, second and third channels along the first and second transverse directions is between 10 micrometers and 3,000 micrometers.

17. A biomimetic microfluidic system comprising:
at least one substrate;
a first chamber formed in the at least one substrate, the first chamber extending from a first input to a first output substantially along a longitudinal direction;
a second chamber formed in the at least one substrate, the second chamber extending from a second input to a second output along the longitudinal direction, wherein at least a portion of the first and second chambers extends substantially parallel along the longitudinal direction;
a membrane separating the first and second chamber along a transverse direction, wherein the membrane creates a fluid communication path passing between the first chamber and second chamber, and is configured to capture a biological source material from a fluid passing through the membrane; and
at least one source configured to selectively introduce into the first chamber and the second chamber, using respective inputs, at least one biological composition at flow rates configured to generate physiological shear rates in the second chamber that are sufficient to induce production of platelets from the captured biological source material; and
a first flow filter positioned upstream from the first input; and
a second flow filter positioned upstream from the second input;
wherein upstream is defined relative to a direction of flow for the at least one biological composition.

18. The system of claim 17, wherein the system further comprises:
a first flow resistor positioned between the first input and the first flow filter; and
a second flow resistor positioned between the second input and the second flow filter.

19. The system of claim 17, wherein the membrane includes a plurality of pores sized less than the biological source material to allow capture of the biological source material generally about the pores.

20. The system of claim 19, wherein the biological source material includes megakaryocytes.

21. The system of claim 19, wherein the pores have a diameter in a range between 3 micrometers and 12 micrometers.

22. The system of claim 17, wherein the membrane includes a surface prepared with a material that include Poly-L-lysine, fibrinogen, collagen type IV, fibronectin, vitronectin, laminin, CCL5, S1PR1, SDF-1, or FGF-4.

23. The system of claim 17, wherein a thickness of the membrane is in a range between 1 micrometer and 20 micrometers.

24. The system of claim 17, wherein the at least one biological composition includes at least one of a semi-solid, a solid, a liquid, and a collection of cells, or a combination thereof.

25. The system of claim 17, wherein the physiological shear rates are in a range between 100 s-1 and 10,000 s-1.

* * * * *